(12) United States Patent
Nishimura et al.

(10) Patent No.: US 8,932,592 B2
(45) Date of Patent: Jan. 13, 2015

(54) COMPOSITIONS AND METHODS FOR TREATING INFLAMMATORY DISORDERS

(75) Inventors: Miyuki Nishimura, Kobe (JP); Yoshimasa Sakamoto, Kobe (JP); Tetsu Kawano, Kobe (JP); Toshio Imai, Kobe (JP)

(73) Assignee: Eisai R&D Management Co., Ltd., Tokyo (JP)

( * ) Notice: Subject to any disclaimer, the term of this patent is extended or adjusted under 35 U.S.C. 154(b) by 0 days.

(21) Appl. No.: 13/504,742

(22) PCT Filed: Oct. 28, 2010

(86) PCT No.: PCT/JP2010/069653
§ 371 (c)(1),
(2), (4) Date: Apr. 27, 2012

(87) PCT Pub. No.: WO2011/052799
PCT Pub. Date: May 5, 2011

(65) Prior Publication Data
US 2012/0213799 A1    Aug. 23, 2012

Related U.S. Application Data

(60) Provisional application No. 61/256,521, filed on Oct. 30, 2009.

(51) Int. Cl.
*A61K 39/395* (2006.01)
*C07K 16/24* (2006.01)
*C12N 15/13* (2006.01)
*C12N 5/10* (2006.01)
*C12P 21/02* (2006.01)

(52) U.S. Cl.
CPC ............ C07K 16/24 (2013.01); *C07K 2317/24* (2013.01); *C07K 2317/34* (2013.01); *C07K 2317/76* (2013.01); *Y10S 514/894* (2013.01)
USPC .................. 424/158.1; 530/387.3; 530/389.2; 435/243; 435/320.1; 435/335; 435/69.6; 536/23.53; 514/12.2; 514/16.6; 514/17.9; 514/18.7; 514/894

(58) Field of Classification Search
None
See application file for complete search history.

(56) References Cited

U.S. PATENT DOCUMENTS

| | | |
|---|---|---|
| 6,013,257 A | 1/2000 | Pan |
| 6,096,312 A | 8/2000 | Nakamura et al. |
| 6,114,507 A | 9/2000 | Shirakawa et al. |
| 6,180,377 B1 | 1/2001 | Morgan et al. |
| 6,420,121 B1 | 7/2002 | Nelson et al. |
| 6,548,654 B1 | 4/2003 | Hardiman et al. |
| 6,566,503 B2 | 5/2003 | Hardiman et al. |
| 7,115,379 B1 | 10/2006 | Hardiman et al. |
| 7,390,490 B1 | 6/2008 | Imai et al. |
| 7,431,924 B2 | 10/2008 | Hardiman et al. |
| 7,585,502 B2 | 9/2009 | Hardiman et al. |
| 7,785,804 B2 | 8/2010 | Hardiman et al. |
| 8,518,401 B1 | 8/2013 | Kuboi et al. |
| 2002/0055456 A1 | 5/2002 | Koch |
| 2002/0192212 A1 | 12/2002 | Imai et al. |
| 2003/0027990 A1 | 2/2003 | Hardiman et al. |
| 2005/0118651 A1 | 6/2005 | Basi et al. |
| 2006/0233710 A1 | 10/2006 | Matsushima et al. |
| 2006/0275297 A1 | 12/2006 | Hardiman et al. |
| 2008/0063635 A1 | 3/2008 | Takahashi et al. |
| 2009/0017032 A1 | 1/2009 | Hardiman et al. |
| 2009/0192212 A1 | 7/2009 | Garner et al. |
| 2009/0317398 A1 | 12/2009 | Hardiman et al. |

FOREIGN PATENT DOCUMENTS

| | | |
|---|---|---|
| EP | 1520586 A1 | 4/2005 |
| EP | 1671648 A1 | 6/2006 |
| EP | 1806145 A1 | 7/2007 |
| JP | 7-509359 A | 10/1995 |
| JP | 8-511420 | 12/1996 |
| JP | 2001218581 A | 8/2001 |
| JP | 2002-345454 A | 12/2002 |
| JP | 2008278889 A | 11/2008 |
| JP | 2012041359 A | 3/2012 |
| JP | 4979388 B2 | 7/2012 |
| WO | WO-94/01547 A2 | 1/1994 |
| WO | WO-97/02290 | 1/1997 |
| WO | WO-00/09511 A1 | 2/2000 |
| WO | WO-01/60406 A1 | 8/2001 |
| WO | WO-02/076990 A1 | 10/2002 |
| WO | WO-03/018549 A2 | 3/2003 |
| WO | WO-2004/108895 A2 | 12/2004 |
| WO | WO-2005/032589 A1 | 4/2005 |
| WO | WO-2005033115 A1 | 4/2005 |
| WO | WO-2006/033386 A1 | 3/2006 |
| WO | WO-2006/046739 A1 | 5/2006 |
| WO | WO-2006107257 A1 | 10/2006 |
| WO | WO-2006107258 A1 | 10/2006 |
| WO | WO-2008/052108 A2 | 5/2008 |

OTHER PUBLICATIONS

Nanki et al, The Journal of Immunology, 2004, 173: 7010-7016.*
Lucas et al, American Journal of Pathology, 2001, vol. 158, No. 3, pp. 855-866.*
http://www.mayoclinic.com/health/bells-palsy/DS00168.*
http://www.mayoclinic.com/health/stroke/DS00150.*
http://www.mayoclinic.com/health/parkinsons-disease/DS00295.*
http://www.mayoclinic.com/health/multiple-sclerosis/DS00188.*
Bazan et al., "A new class of membrane-bound chemokine with a $CX_3C$ motif," *Nature* 385: 640-644 (1997).
Clark et al., "Inhibition of spinal microglial cathepsin S for the reversal of neuropathic pain," *PNAS* 104(25): 10655-10660 (2007).
Goda et al., "$CX_3C$-Chemokine, Fractalkine-Enhanced Adhesion of THP-1 Cells to Endothelial Cells Through Integrin-Dependent and -Independent Mechanisms," *J. Immunol.* 164: 4313-4320 (2000).

(Continued)

*Primary Examiner* — Bridget E Bunner
*Assistant Examiner* — Fozia Hamud
(74) *Attorney, Agent, or Firm* — Clark & Elbing LLP

(57) ABSTRACT

The present invention features compositions and methods related to humanized antibodies and FKN-binding fragments thereof that bind fractalkine.

62 Claims, 14 Drawing Sheets

(56) References Cited

OTHER PUBLICATIONS

Fraticelli et al., "Fractalkine (CX3CL1) as an amplification circuit of polarized Th1 responses," *The Journal of Clinical Investigation* 107(9): 1173-1181 (2001).
Suzuki et al., "Inhibition of CX3CL1 (Fractalkine) Improves Experimental Autoimmune Myositis in SJL/J Mice," *J. Immunol.* 175: 6987-6996 (2005).
First Examination Report for New Zealand Patent Application IP No. 599779, dated Jan. 25, 2013 (2 pages).
Further Examination Report for New Zealand Patent Application IP No. 599779, dated May 1, 2013 (2 pages).
Office Action for Pakistani Patent Application No. 908/2010, dated Jan. 24, 2012, English language translation provided (4 pages).
Office Action for Taiwanese Patent Application No. 099137131, dated Dec. 25, 2012, English language translation provided (4 pages).
Office Action for Vietnamese Patent Application No. 1-2012-01320, dated Jun. 29, 2012, English language translation provided (2 pages).
International Preliminary Report on Patentability for PCT/JP2010/069653, issued May 1, 2012 (7 pages).
International Search Report for PCT/JP2010/069653, mailed Mar. 8, 2011 (6 pages).
Office Action for Chilean Patent Application No. 1143-2012, dated Aug. 1, 2013 (7 pages).
Office Action for Chinese Patent Application No. 201080049138.0, dated Jul. 2, 2013 (15 pages). English language translation provided.
Reply to Office Action for New Zealand Patent Application No. 599779, filed Apr. 18, 2013 (14 pages).
Reply to Office Action for Taiwanese Patent Application No. 099137131, filed Mar. 27, 2013 (21 pages). English language translation provided.
Reply to Office Action for Vietnamese Patent Application No. 1-2012-01320, filed Jul. 25, 2013 (12 pages). English language translation provided.
Umehara et al., "Fractalkine in rheumatoid arthritis and allied conditions," Mod Rheumatol. 16(3):124-30 (2006).
Saederup et al., "Fractalkine deficiency markedly reduces macrophage accumulation and atherosclerotic lesion formation in CCR2-/- mice: evidence for independent chemokine functions in atherogenesis," Circulation. 117(1):1642-8 (2008).
Inoue et al., "Antagonist of fractalkine (CX3CL1) delays the initiation and ameliorates the progression of lupus nephritis in MRL/Ipr mice," Arthritis Rheum. 52(5):1522-33 (2005).
Extended European Search Report and Written Opinion for European Patent Application No. 10826929.1, dated Nov. 7, 2013 (7 pages).
Hotta, "An actual case of measurement of candidate antibody drug compound in serum using LC-MS/MS," The 8th Short Course of the Japanese Society for Study of Xenobiotics (presented on May 8, 2014) (63 pages). English language translation provided. Abstract issue date: Apr. 20, 2014 (sending date) or Apr. 21, 2014 (arrival date).
Hotta, "Bioanalysis of antibody drug with LC-MS/MS," The 41st Biological Mass Spectometry Conference (BMS2014) (presented on Jul. 7, 2014) (73 pages). English language translation provided. Abstract issue date: Jul. 7, 2014.
Imai, "Role of FKN-CX3CR1 system on inflammatory immune disease," The 79th Annual Meeting of the Japanese Society of Interferon & Cytokine Research (presented on Jun. 20, 2014) (67 pages). English language translation provided. Abstract issue date: Jun. 7, 2014.
Imai, "Therapy of inflammatory immune diseases targeting for cell infiltration regulation molecule," The 35th Japanese Society of Inflammation and Regeneration (presented on Jul. 4, 2014) (92 pages). English language translation provided. Abstract issue date: Jun. 10, 2014.
PR Leaflet of Kobe Biomedical Innovation Cluster, <http://kansai-tokku.jp/about/kob_web_0718.pdf>, first uploaded on Jul. 11, 2014, revised on Jul. 22, 2014, and retrieved on Sep. 8, 2014 (9 pages). English language translation provided.

Shimbun, "1/30,000 Chance of Commercialization of New Drug," KOBE Biomedical Innovation Cluster (published on Aug. 27, 2014) (2 pages). English language translation provided.
Examiner's Report Issued on Patent of Invention Application for Chilean Application No. 1143-2012, dated Jul. 1, 2014 (6 pages).
First Stage Substantive Examination Result and English translation for Indonesian Application No. W-00-2012-02106, dated Jul. 16, 2014 (5 pages).
Notice of Reasons for Rejection and English translation for Japanese Application No. 2012-520621, dated Aug. 26, 2014 (7 pages).
Abo, "Connections between physical conditions and immune system: the mechanism of the onset of autoimmune diseases," Chiryo (The Journal of Therapy) 80(12):92-98 (1998).
Aida S., Hisanori Umehara, Hiroshi Inoue, Osamu Yoneda, Toshio Imai, Naochika Domae, "Adhesion of Thp-1 cell and vascular endothelial cell via CX3C-chemokine, fractalkine," The 21st Annual Meeting of the Japanese Society of Inflammation, Tokyo, Jul. 4, 2000, 2 pages. Abstract No. 141.
Aida S., Hisanori Umehara, Osamu Yoneda, Hitoshi Inoue, Toshio Imai, Osamu Yoshie, Hisao Imai, Naochika Domae., The 29th Annual Meeting of The Japanese Society for Immunology, Kyoto, Dec. 3, 1999, 4 pages. Abstract No. Op-3-C2-090-I.
Ancuta et al., "Fractalkine preferentially mediates arrest and migration of $CD16^+$ monocytes," J. Exp. Med. 197(12):1701-1707 (2003).
Anonymous, "Handling of Immune Animal," Sin-Seikagaku Jikken Koza 12 (Molecular Immunology III—antigen, antibody, complement):3-6 (1992).
Arita Y, Mizuno K, Nishimura M, Ogasawara H, Muramoto K, Imai T. "Identification of a novel activating receptor on dendritic cells and its role in mouse collagen-induced arthritis." Autoimmunity congress 2008, Porto, Portugal, Sep. 10-14, 2008, 2 pages. Abstract No. 513.
Arita Y, Nishimura M, Kawano T, Kuboi Y, Muramoto K, Imai T. "Antibody blockade of TARM abrogates intestinal inflammation in experimental T cell-induced colitis." 14th International Congress of Immunology, Kobe, Aug. 23-27, 2010, 17 pages. Abstract No. PP-065-34.
Auffray et al., "Monitoring of blood vessels and tissues by a population of monocytes with patrolling behavior," Science. 317:666-70 (2007).
Baba et al., "Constitutive expression of various chemokine genes in human T-cell lines infected with human T-cell leukemia virus type 1: role of the viral transactivator Tax," Int J Cancer. 66(1):124-9 (1996).
Baba et al., "Identification of CCR6, the specific receptor for a novel lymphocyte-directed CC chemokine LARC," J Biol Chem. 272(23):14893-8 (1997).
Baba M., Toshio Imai, Shin Takagi, Osamu Yoshie., "Cloning of novel human CC type chemokine LARC and identification of its receptor CCR6.", The 27th Annual Meeting of the Japanese Society for Immunology, Tokyo, Oct. 30, 1997, 2 pages. Abstract No. 2P234.
Bauer et al., "Perforin deficiency attenuates collagen-induced arthritis," Arthritis Res. Ther. 7(4): R877-R884 (2005).
Beck et al., "Release of CXC-chemokines by human lung microvascular endothelial cells (LMVEC) compared with macrovascular umbilical vein endothelial cells," Clin. Exp. Immunol. 118(2):298-303 (1999).
Belke-Louis et al., "µ-Opioid receptor expression in High Five™ insect cells is regulated by 5' untranslated region (5'UTR)," Life Science. 64(11):913-21 (1999).
Birrell et al., "Pharmacological Assessment of the Nitric-Oxide Synthase Isoform Involved in Eosinophilic Inflammation in a Rat Model of Sephadex-Induced Airway Inflammation," Journal of Pharmacology and Experimental Therapeutics. 304(3):1285-91 (2003).
Bérangère et al., "Fractalkine: moving from chemotaxis to neuroprotection," Nature Neuroscience. 9(7):859-61 (2006).
Campbell, General properties and applications of monoclonal antibodies. *Monoclonal Antibody Technology*. Elsevier Science Publishers B.V., 1-32 (1958).
Cardona et al., "Control of microglial neurotoxicity by the fractalkine receptor," Nature Neuroscience. 9:917-24 (2006).
Chen et al., "In vivo inhibition of CC and $CX_3C$ chemokine-induced leukocyte infiltration and attenuation of glomerulonephritis in wistar-kyoto (WKY) rats by vMIP-II," J. Exp. Med. 188(1):193-198 (1998).

(56) References Cited

OTHER PUBLICATIONS

Chen et al., "Overstaying their welcome: defective CX3CR1 mircoglia eyed in macular degeneration," J. Clin. Invest. 117(10):2758-2762 (2007).
Chisari, "Cytotoxic T cells and viral hepatitis," J. Clin. Invest. 99(7):1472-1477 (1997).
Chuntharapai et al., "Generation of monoclonal antibodies to chemokine receptors," Methods in Enzymology. 288:15-27 (1997).
Combadière et al., "CX3CR1-dependent subretinal microglia cell accumulation is associated with cardinal features of age-related macular degeneration," J. Clin. Invest. 117(10):2920-2928 (2007).
Combadière et al., "Decreased atherosclerotic lesion formation in CX3CR1/apolipoprotein E double knockout mice," Circulation 107(7): 1009-1016 (2003).
Cuzzocrea et al., "Beneficial effects of GW274150, a novel, potent and selective inhibitor in iNOS activity, in a rodent model of collagen-induced arthritis," Eur. J. Pharmacol. 453(1):119-129 (2002).
D'Ambrosio et al., "Chemokine receptors in inflammation: an overview," J Immunol Methods. 273:3-13 (2003).
Dagkalis et al., "CX3CR1-deficiency is associated with increased severity of disease in experimental autoimmune uveitis," Immunology 128:25-33 (2009).
Dorland's Illustrated Medical Dictionary, 27th Edition, pp. 1089 and 1460 (1998).
Echigo et al., "Expression of fractalkine and its receptor, $CX_3CR1$, in atopic dermatitis: Possible contribution to skin inflammation," Journal of Allergy and Clinical Immunology. 113(5):940-8 (2004).
Feng et al., "Prevention of crescentic glumerulonephritis by immunoneutralization of the fractalkine receptor $CX_3CR1$ *Rapid Communication*," Kidney International. 56:612-20 (1999).
Fischer et al., "Modulation of experimental autoimmune encephalomyelitis: effect of altered peptide ligand on chemokine and chemokine receptor expression," J. Neuroimmunol. 110:195-208 (2000).
Fong et al., "$CX_3CR1$ tyrosine sulfation enhances fractalkine-induced cell adhesion," J Biol Chem. 277(22):19418-23 (2002).
Fong et al., "Fractalkine and $CX_3CR1$ mediate a novel mechanism of leukocyte capture, firm adhesion, and activation under physiologic flow," J Exp Med. 188(8):1413-9 (1998).
Fong et al., "Ultrastructure and function of the fractalkine mucin domain in $CX_3C$ chemokine domain presentation," J Biol Chem. 275(6):3781-6 (2000).
Ford et al., "Fusion tails for the recovery and purification of recombinant proteins," Protein Expression and Purification. 2:95-107 (1991).
Fort et al., "A role for NK cells as regulators of $CD4^+$ T cells in a transfer model of colitis," J. Immunol. 161:3256-3261 (1998).
Foussar et al., Fractalkine receptor expressions by T lymphocyte subpopulations in vivo producing of fractalkine in human, Interferon Cytokine Res. 19(Suppl. 1):S139. Abstract No. P164. 1999.
Fujito T., Wataru Ikeda, Shigeki Kakunaga, Tatsushi Shingai, Akio Yamada, Yukiko Minami, Toshio Imai, Yoshimi Takai., Nectin-like molecule (NecI)-5/Tage4/PVR/CD155: Regulation of proliferation through Ras-Raf-MEK-ERK signaling., The 63rd Annual Meeting of the Japanese Cancer Association., Fukuoka, Sep. 29, 2004, 4 pages. Abstract No. W-92.
Fukudome et al., "Identification of membrane antigen C33 recognized by monoclonal antibodies inhibitory to human T-cell leukemia virus type 1 (HTLV-1)-induced syncytium formation: altered glycosylation of C33 antigen in HTLV-1-positive T cells," J Virol. 66(3): 1394-401 (1992).
Fukudome et al., "Strong induction of Icam-1 in human T cells transformed by human T-cell-leukemia virus type 1 and depression of ICAM-1 or LFA-1 in adult T-cell-leukemia-derived cell lines," Int J Cancer. 52(3): 418-27 (1992).
Fukudome K., Toshio Imai, Shin Takagi, Yorio Hinuma, Osamu Yoshie., Expression induction of ICAM-1, and ICAM-1 or LFA-1 expression inhibition in ATL cell line by HTLV-1., The 22nd Annual Meeting of The Japanese Society for Immunology, Nagoya, Nov. 27, 1992. 2 pages. Abstract No. 3A7-9.

Furuse et al., "Induction of strong homotypic adhesion in human T cell lines positive with human T-cell leukemia virus type 1 by monoclonal antibodies to MHC class I and beta 2-microglobulin," Cell Immunol. 143(2): 298-309 (1992).
Fusaoka E., Etsuko Rikitsu, Keiko Yamaguchi, Yoko Inoue, Miyuki Nishimura, Toshio Imai. AMICA-CAR interaction stimulates the transmigration of Th1 cells by forming a migratory ringlike structure. The 59th Annual Meeting of the Japan Society for Cell Biology, Fukuoka. May 28, 2007, 18 pages. Abstract No. 2P-033.
Fusaoka-Nishioka et al "Differential effects of laminin isoforms on axon and dendrite development in hippocampal neurons," Neurosci Res. 71(4):421-6 (2011).
Geissmann et al., "Blood monocytes consist of two principal subsets with distinct migratory properties," Immunity 19(1):71-82 (2003).
Godeny et al., "Involvement of natural killer cells in coxsackievirus B3-induced murine myocarditis," J. Immunol. 137(5):1695-1702 (1986).
Goker et al., "Acute graft-vs-host disease: pathobiology and management," Exp. Hematol. 29:259-277 (2001).
Gouda S., Hisanori Umehara, Osamu Yoneda, Hiroshi Inoue, Toshio Imai, Osamu Yoshie, Hisao Imai, Naochika Doumae., "Effect of CX3C-chemokine, Fractalkine on adhesion of THP-1 cell to extracellular matrix protein.", The 26th Annual Meeting of the Japanese Society for Clinical Immunology, Oct. 1998, 3 pages. Abstract No. 3-B2-300.
Gouda S., Hisanori Umehara, Osamu Yoneda, Hiroshi Inoue, Toshio Imai, Osamu Yoshie, Hisao Imai, Naochika Doumae., "Effect of CX3C-chemokine, Fractalkine on adhesion of THP-1 cell to extracellular matrix protein.", The 63rd Annual Meeting of the Japanese Society for Interferon & Cytokine Research, Tokyo, Jul. 31, 1998, 2 pages. Abstract No. 48.
Graubert et al., "Perforin/granzyme-dependent and independent mechanisms are both important for the development of graft-versus-host disease after murine bone marrow transplantation," J. Clin. Invest. 100(4):904-11 (1997).
Greaves et al., "Inflammation and immune responses in atherosclerosis," Trends in Immunology. 23(11):535-541 (2002).
Grewal et al., "CD40 and CD154 in cell-mediated immunity," Annu. Rev. Immunol. 16:111-135 (1998).
Griffiths et al., "Perforin and granzyme A expression indentifying cytolytic lymphocytes in rheumatoid arthritis," Proc Natl Acad Sci USA. 89:549-53 (1992).
H. Umehara, M. Miyaji, E.T. Bloom, T. Imai. A role of fractalkine as the vascular gateway for cytotoxic lymphocytes. FASEB meeting, Washington D.C., (2004), 1 page. Abstract No. 332.8.
Harrison et al., "Mutational analysis of the fractalkine chemokine domain. Basic amino acid residues differentially contribute to CX3CR1 binding, signaling, and cell adhesion," J Biol Chem. 276(24):21632-41 (2001).
Harrison et al., "Role for neuronally derived fractalkin in mediating interactions between neurons and CX3R1-expressing microglia," Proc Natl Acad Sci USA. 95:10896-901(1998).
Hashida et al., "The novel monoclonal antibody MH8-4 inhibiting cell motility recognizes integrin alpha 3: inverse of its expression with metastases in colon cancer," Int J Oncol. 18(1):89-95 (2001).
Haskell et al., "Targeted deletion of $CX_3CR1$ reveals a role for fractalkine in cardiac allograft rejection," J. Clin. Invest. 108(5):679-688 (2001).
Henke et al., "The role of $CD8^+$ T lymphocytes in coxsackievirus b3-induced myocarditis," J. Virol. 69(11):6720-6728 (1995).
Hieshima et al., "Molecular cloning of a novel human CC chemokine liver and activation-regulated chemokine (LARC) expressed in liver. Chemotactic activity for lymphocytes and gene localization on chromosome 2," J Biol Chem. 272(9):5846-53 (1997).
Hieshima K., Naoyuki Nomiyama, Toshio Imai, Jun Kusuda, Hajime Tei, Osamu Yoshie, Yoshiyuki Sakaki, Kiyoshi Takatsuki, Kiyoshi Miura., "Novel human chemokine gene found from EST data base.", The 19th Annual Meeting of the Molecular Biology Society of Japan, Sapporo, Aug. 27, 1994, 3 pages. Abstract No. 2-P-1068.
Hieshima K., Toshio Imai, Masataka Baba, Retsu Miura, Osamu Yoshie, and Hisayuki. Nomiyama., "Characterization of Human CC

(56) References Cited

OTHER PUBLICATIONS chemokine PARC." The 20th Annual Meeting of The Molecular Biology Society of Japan, Kyoto, Dec. 17, 1997, 3 pages. Abstract No. 2-157P-328.
Hieshima et al., "A novel human CC chemokine PARC that is most homologous to macrophage-inflammatory protein-1 alpha/LD78 alpha and chemotactic for T lymphocytes, but not for monocytes," J Immunol. 159(3):1140-9 (1997).
Holmes et al., "Intra-neural administration of fractalkine attenuates neuropathic pain-related behaviour, " J Neurochem. 106(2):640-9 (2008).
Hoover et al., "The crystal structure of the chemokine domain of fractalkine shows a novel quarternary arrangement," J. Biol. Chem. 275(30):23187-23193 (2000).
Hoshino et al., "Deficiency of chemokine receptor CCR1 causes osteopenia due to impaired functions of osteoclasts and osteoblasts." J Biol Chem. 285(37):28826-37 (2010).
Hoshino et al., "Roles of chemokine receptor CX3CR1 in maintaining murine bone homeostasis through the regulation of both osteoblasts and osteoclasts," J Cell Sci. 126(Pt 4):1032-45 (2013).
Ide M., Manae Kurokawa, Ritsuko Ikeda, Hideshi Yoshikawa, Toshio lmai, Takuo Hashimoto, Noboru Suzuki., Clarification of transplantation treatment of damaged brain and of the migration mechanism of transplanted cells to the damaged part by nerve precursor cells derived from mice embryonic stem cells., The 4th Congress of the Japanese Society for Regenerative Medicine., Osaka, Mar. 2, 2005, 4 pages. Abstract No. P2-190.
Ikeda et al., " Nectin-like molecule-5/Tage4 enhances cell migration in an integrin-dependent, Nectin-3-independent manner," J Biol Chem. 279(17):18015-25 (2004).
Ikeda et al., "Tage4/Nectin-like molecule-5 heterophilically trans-interacts with cell adhesion molecule Nectin-3 and enhances cell migration," J Biol Chem. 278(30):28167-72 (2003).
Ikeda W., Shigeki Kadonaga, Shinpei Itoh, Kyoji Takekuni, Koji Morimoto, Keiko Satoh, Shoichi Takeuchi, Toshio Imai, Yoshimi Takai. Characterization of Nectin-like protein-1, -2, -3. The 25th Annual Meeting of The Molecular Biology Society of Japan, Yokohama, Dec.13-14, 2002, 25 pages.
Imai "Chemokine Receptor," Igaku No Ayumi additional volume, Novel Development of the study of seven-transmembrane receptor. 90-95 (2001). English language translation provided.
Imai et al., "C33 antigen and M38 antigen recognized by monoclonal antibodies inhibitory to syncytium formation by human T cell leukemia virus type 1 are both members of the transmembrane 4 superfamily and associate with each other and with CD4 or CD8 in T cells," J Immunol. 151(1 1):6470-81 (1993).
Imai et al., "C33 antigen recognized by monoclonal antibodies inhibitory to human T cell leukemia virus type 1-induced syncytium formation is a member of a new family of transmembrane proteins including CD9, CD37, CD53, and CD63," J Immunol. 149(9):2879-86 (1992).
Imai et al., "Chemokine receptors as drug targets," Pharmacia. 37(4):302-306 (2001). English language translation.
Imai et al., "Enhanced expression of LFA-3 on human T-cell lines and leukemic cells carrying human T-cell-leukemia virus type 1," Int J Cancer. 55(5):811-6 (1993).
Imai et al., "Expression of CX3CR1 on cytotoxic lymphocytes in acute GVHD mice," FASEB J. 16(4):A691 (2002) (Abstract only).
Imai et al., "Fractalkine and inflammatory diseases," Nihon Rinsho Meneki Gakkai Kaishi 28(3):131-9 (Review) (2005). English translation provided.
Imai et al., "Identification and molecular characterization of fractalkine receptor CX₃CR1, which mediates both leukocyte migration and adhesion," Cell. 91(4):521-530 (1997).
Imai et al., "Leukocyte trafficking mediated by fractalkine," Meneki/Immunology Frontier. 11(1):30-35 (2001). English language translation provided.
Imai et al., "Macrophage-derived chemokine is a functional ligand for the CC chemokine receptor 4," J Biol Chem. 273(3):1764-8 (1998).

Imai et al., "Molecular analyses of the association of CD4 with two members of the transmembrane 4 superfamily, CD81 and CD82," J Immunol. 155(3):1229-39 (1995).
Imai et al., "Molecular cloning of a novel T cell-directed CC chemokine expressed in thymus by signal sequence trap using Epstein-Barr virus vector," J Biol Chem. 271(35):21514-21 (1996).
Imai et al., "Selective recruitment of CCR4-bearing Th2 cells toward antigen-presenting cells by the CC chemokines thymus and activation-regulated chemokine and macrophage-derived chemokine," Int Immunol. 11(1):81-8 (1999).
Imai et al., "The T cell-directed CC chemokine TARC is a highly specific biological ligand for CC chemokine receptor 4," J Biol Chem. 272(23):15036-42 (1997).
Imai T. "Adhesion molecules that regulate the cell trafficking of immune cells and cancer cells." 69th Annual Meeting of the Japanese Cancer Association, Osaka, Sep. 22-24, 2010, 29 pages. Abstract No. s3-5.
Imai T., "Regulation of inflammatory diseases by inhibiting cell infiltration."?Kobe University Global COE Program on Signal Transduction Medicine in the Coming Generation 4th Workshop, Awaji Island, Jul. 9-10, 2012, 21 pages.
Imai T., Chemokine and cell adhesion molecule which regulate Transmigration. The 1st Blood Immunity Network in Kanazawa, Oct. 1-2, 2005, 36 pages.
Imai T., "The role of fractalkine in inflammatory diseases," Experimental Medicine. 23(20):78-83 (2005). English language translation provided.
Imai T., Application of chemokine from basic research to drug development. Incorporated foundation, Suntory Institute for Bioorganic Research, Seminor. Osaka, Oct. 26, 2004, 106 pages.
Imai T., Diversities of chemokine and its receptor., The 28th Annual Meeting of the Japanese Society for Clinical Immunology., Workshop, Tokyo, Sep. 28-30, 2000, 2 pages. Abstract No. 11-6.
Imai T., Effort for Integrative Cell Biology for Medicine, Symposium for Biomedical Academic exchange in Kobe, Periodical 6th, Kobe, Feb. 20, 2007, 82 pages.
Imai T., Fractalkine and Inflammation, the 25th Annual Meeting of the Japanese Society of Inflammation and Regeneration, Workshop, Tokyo, Jul. 13, 2004, 4 pages. Abstract No. W-6-4.
Imai T., K. Hieshima, M. Baba, G. Opdenakker, J. Van Damme, H. Nomiyama, O. Yoshie. Molecular cloning of a novel human CC chemokine LARC expressed in Liver. Keystone Symposia: The role of chemokines in leukocyte trafficking and disease, Colorado, Apr. 2, 1997, 2 pages. Abstract No. 210.
Imai T., Kenji Fukudome, Yorio Hinuma, Osamu Yoshie., C33 antigen recognized by monoclonal antibodies inhibitory to HTLV-1-induced syncytium formation is a member of newly defined tetra spans trans membrane protein superfamily., The 22nd Annual Meeting of The Japanese Society for Immunology, Nagoya, Nov. 25, 1992, 2 pages. Abstract No. 1A1-5.
Imai T., Masataka Baba, Morio Yagira, Shin Takagi, Osamu Yoshie. ,Identification and molecular function analysis of membrane-bound CX3C chemokine (fractalkine) receptor, CX3CR1 which induces migration and cell adhesion of leucocyte., The 27th Annual Meeting of the Japanese Society for Immunology, Tokyo, Oct. 30, 1997, 2 pages. Abstract No. 2j16.
Imai T., Miyuki Nishimura, the CX3CR1 expression and its role in donor derived T cell in the case of mouse acute GVHD model.The 67th Annual Meeting of the Japanese Society for Interferon & Cytokine Research, Tokyo (2002), 16 pages. Abstract No. B-6.
Imai T., Miyuki Nishimura, Yoshikazu Kuboi, Keiko Mizuno, Kenzo Muramoto., Role of the fractalkine-CX3CR1 system in ConA hepatitis., The 34th Annual Meeting of the Japanese Society for Immunology, Sapporo, Dec. 1, 2004, 4 pages. Abstract No. 1-B-W1-04-P.
Imai T., Miyuki Nishimura, Yoshikazu Kuboi, Keiko Mizuno, Kenzo Muramoto., Treatment and action mechanism by anti-fractalkine/CX3CL1 antibody in autoimmune disorder models., The 71st Annual Meeting of the Japanese Society for Interferon & Cytokine Research, Kyoto, Jul. 20-21, 2005, 40 pages. Abstract No. P-1/W4-4.
Imai T., Nishimura M. Expression of CX3CR1 on cytotoxic lymphocytes in acute GVHD mice. Experimental Biology 2002, FASEB Meeting, New Orleans, LA (2002), 16 pages. Abstract 514.8.

(56) References Cited

OTHER PUBLICATIONS

Imai T., Osamu Yoshie. Lymphocyte subsets and chemokine receptors. The 30th Annual Meeting of the Japanese Society for Immunology, Symposium, Sendai, Nov. 16, 2000, 24 pages. Abstract No. s12-3.
Imai T., Osamu Yoshie., Fractalkine., The 28th Annual Meeting of The Japanese Society for Immunology, Symposium, Kobe, Dec. 1998, 1 page. Abstract No. Si-4.
Imai T., Shin Takagi, Osamu Yoshie., Identification novel T cell-specific CC type chemokine TARC expressed in thymus., The 26th Annual Meeting of the Japanese Society for Immunology, Yokohama, Nov. 26, 1994, 3 pages. Abstract No. 1P3-33.
Imai T., Toward to Cellular Biology leading to Drug Development., The Society for the Pursuit of Novel Bioactive Resources, Yokohama, Jun. 13, 2004, 86 pages.
Imai T., Yoshikazu Kuboi, Miyuki Nishimura, Keiko Mizuno, Hideaki Ogasawara, Kenzo Muramoto. Treatment and action mechanism of inflammatory bowel disease (IBD) model by anti-fractalkine/CX3CL1 antibody. The 71st Annual Meeting of the Japanese Society for Interferon & Cytokine Research, Nishinomiya, Jul. 7-8, 2006, 24 pages. Abstract No. P-3.
Imai T.,Cellular infiltration and inflammatory disorder. Lecture in Kobe University Graduate School of Medicine, Kobe, Jul. 31, 2007, 129 pages.
Imai, " Fractalkine, hybrid molecule of chemokine and adhesion molecule," Annual Review Meneki. 2000:186-192 (1999). English language translation provided.
Imai, "CCR4," Chemokine Handbook, Cell Technology additional volume. 185-188 (2000). English language translation provided.
Imai, "Cell Adhesion and Migration Regulated by Chemokines," Cell Technology. 19(5):717-722 (2000). English language translation provided.
Imai, "Chemokine expression in insect cells," Methods Mol Biol. 138:23-32 (2000).
Imai, "Cloning of novel chemokines using a signal sequence trap method," Methods Mol Biol. 138:11-21 (2000).
Imai, "CX3CL1/Fractalkine," Rinsho Meneki/Allergology. 57(21):483-490 (2012). English language translation provided.
Imai, "Cx3cr/xcr (fractalkine/neurotactin, lymphotactin)," All of cytokines and chemokines. 459-470 (2004). English language translation provided.
Imai, "CX3CR1," Chemokine Handbook, Cell Technology additional volume. 215-219 (2000). English language translation provided.
Imai, "Fractalkine," Chemokine Handbook, Cell Technology additional volume. 142-145 (2000). English language translation provided.
Imai, "Fractalkine: a Novel Type of Hybrid Molecule That Mediates both Cell Adhesion and Migration," Cell Technology. 17(7):1046-1053 (1998). English language translation provided.
Imai, "Interaction between Immune Cells and Vascular Endothelial Cells in Cell Infiltration," Vascular Endothelial Cell Research Frontier. 69-82 (2004). English Language Translation Provided.
Imai, "MDC," Chemokine Handbook, Cell Technology additional volume. 117-120 (2000). English language translation provided.
Imai, "Novel chemokines/chemokine receptors and immune system," Soshiki Baiyo Kougaku. 24(12):457-460 (1998). English language translation provided.
Imai, "Pathophysiological Roles of Fractalkine," Igaku No Ayumi additional volume, Cytokine-state of arts. Ishiyaku Shuppan:190-193 (2004). English language translation provided.
Imai, "TARC," Chemokine Handbook, Cell Technology additional volume. 114-116 (2000). English language translation provided.
Imai, "Temporal and spacial regulation of signaling in migration of inflammatory cell," Saibou. 31(13):525-529 (1999). English language translation provided.
Imai, "Th1/Th2 and Fractalkine," Igaku No Ayumi. 190(9):817 (1999). English language translation provided.

Imai, "The Function of Fractalkine and its Involvement in Pathology," Rinsho Meneki. 45(4):411-417 (2006). English language translation provided.
Imamura et al., "Pharmacological preconditioning with resveratrol: an insight with iNOS knockout mice," Am. J. Physiol. Heart Circ. Physiol. 282(6):H1996-H2003 (2002).
Inoue H., Hisanori Umehara, Seiji Aida, Osamu Yoneda, Toshio Imai, Naochika Domae., Costimulatory signal by IL-2 and CD2-mediated stimulation on NK cell proliferation., The 21st Annual Meeting of the Japanese Society of Inflammation, Tokyo, Jul. 4, 2000, 2 pages. Abstract No. 120.
Ishikawa-Mochizuki et al., "Molecular cloning of a novel CC chemokine, interleukin-11 receptor alpha-locus chemokine (ILC), which is located on chromosome 9p13 and a potential homologue of a CC chemokine encoded by molluscum contagiosum virus," FEBS Lett. 460(3):544-8 (1999).
Ishizaki et al., "Defective chemokine-directed lymphocyte migration and development in the absence of Rho guanosine diphosphate-dissociation inhibitors alpha and beta," J Immunol. 177(12):8512-21 (2006).
Ishizaki H., Atsushi Togawa, Miki Okamoto, Akiko Hamaguchi, Koji Morimoto, Minehisa Ootsuka, Toshio Imai, Yoshimi Takai, Jun Miyoshi. Phenotypic analysis of Rho GDI α/β double knockout mouse (DKO) mouse.The 25th Annual Meeting of The Molecular Biology Society of Japan, Yokohama, Dec. 13-14, 2002, 35 pages.
Ishizaki H., Miki Okamoto, Keiko Hori, Yu Itoh, Miyuki Nishimura, Toshio Imai. Yoshimi Takai, Jun Miyoshi., Defective chemokine-directed lymphocyte migration and development in the absence of Tho GDP-dissociation inhibitor alpha/beta., The 28th Annual Meeting of the Molecular Biology Society of Japan., Fukuoka, Dec. 7-10, 2005, 27 pages. Abstract No. 1 P-0928.
Iwatani H., Takahito Ito, Masaya Yamato, Akira Suzuki, Naohiko Ueda, Enyu Imai, Seiji Hori1, Toshio Imai4, Wataru Ikeda2, Yoshimi Takai.Involvement of NECL2/TSLC1 in nephrogenesis. The 45th Annual Meeting of the Japanese Society of Nephrology .Apr. 25, 2003, 3 pages. Abstract No. P-S120.
Johnston et al., "A role for proinflammatory cytokines and fractalkine in analgesia, tolerance, and subsequent pain facilitation induced by chronic intrathecal morphine," J. Neurosci. 24(33):7353-65 (2004).
Kakunaga et al., "Enhancement of serum-and platelet-derived growth factor-induced cell proliferation by Necl-5/Tage4/poliovirus receptor/CD155 through the Ras-Raf-MEK-ERK signaling," J Biol Chem. 279(35):36419-25 (2004).
Kakunaga S., Wataru Ikeda, Kyoji Takekuni, Koji Morimoto, Keiko Satoh, Masakazu Takeuchi, Toshio Imai, Yoshimi Takai., Nectin-like molecule (Necl)-5/Tage4 (2): nectin-independent, integrin-dependent cancer cell migration-enhancing activity, The 62nd Annual Meeting of the Japanese Cancer Association, Nagoya, Sep. 25, 2003, 12 pages. Abstract No. 1097-OA.
Kammer et al., "Molecular mimicry of human cytochrome P450 by hepatitis C virus at the level of cytotoxic T cell recognition," J. Exp. Med. 190(2):169-176 (1999).
KAN Research Institute, Inc., "Knowledge, Action and Network" NatureJobs (2004). doi:10.1038/nj0417, published online Jan. 8, 2014.
Kaneko et al., "Chemerin activates fibroblast-like synoviocytes in patients with rheumatoid arthritis," Arthritis Res Ther. 13(5):R158 (2011).
Kaneko K., Yoshishige Miyabe, Aiko Takayasu, Shin Fukuda, Chie Miyabe, Masashi Ebisawa, Waka Yokoyama, Kaori Watanabe, Toshio Imai, Kenzo Muramoto, Yuya Terashima, Takahiko Sugihara, Kouji Matsushima, Nobuyuki Miyasaka, and Toshihiro Nanki. "Chemerin Activates Fibroblast-like Synoviocytes in Patients with Rheumatoid Arthritis." The 75th annual meeting of the American College of RheumatologyWashington, D.C Nov. 9-14, 2011, 2 pages. Abstract No. 376.
Kankuri et al., "Suppression of Acute Experimental Colitis by a Highly Selective Inducible Nitric-Oxide Synthase Inhibitor, $N$-[3-(Aminomethyl)(benzyl]acetamidline," Journal of Pharmacology and Experimental Therapeutics. 298(3):I128-32 (2001).
Kawana et al., "Location of KAI1 on the short arm of human chromosome 11 and frequency of allelic loss in advanced human prostate cancer," Prostate. 32(3):205-13 (1997).

(56) References Cited

OTHER PUBLICATIONS

Kawasaki et al., "Intervention of Thymus and Activation-Regulated Chemokine Attenuates the Development of Allergic Airway Inflammation and Hyperresponsiveness in Mice," J Immunol. 166(3):2055-62 (2001).

Kawasaki S., Hiroyuki Yoneyama, Hajime Takizawa, Toshio Imai, Osamu Yoshie, Tsunaharu Matsushima., Roles of TARC for mouse asthma model.The 29th Annual Meeting of The Japanese Society for Immunology, Kyoto, Dec. 1, 1999, 3 pages. Abstract P-1-D-645-II.

Khan et al., "IP-10 is critical for effector T cell trafficking and host survival in toxoplasma gondii infection," Immunity 12:483-494 (2000).

Kitagawa et al., "Inhibition of CCL20 increases mortality in models of mouse sepsis with intestinal apoptosis," Surgery. 154(1):78-88 (2013).

Kitaura et al., "Molecular Cloning of a Novel Human CC Chemokine (Eotaxin-3) That Is a Functional Ligand of CC Chemokine Receptor 3," J Biol Chem. 274(39):27975-80 (1999).

Kitaura et al., "Molecular cloning of human eotaxin, an eosinophil-selective CC chemokine, and identification of a specific eosinophil eotaxin receptor, CC chemokine receptor 3," J Biol Chem. 271(13):7725-30 (1996).

Kiyozumi et al., "Identification of a novel cell-adhesive protein spatiotemporally expressed in the basement membrane of mouse developing hair follicle," Exp Cell Res. 306(1):9-23 (2005).

Kiyozumi et al., "Identification of genes expressed during hair follicle induction." J Dermatol 38(7):674-9 (2011).

Kobayashi et al., "Exclusive increase of $CX3CR1^+CD28^-CD4^+$ T cells in inflammatory bowel disease and their recruitment as intraepithelial lymphocytes," Inflamm. Bowel. Dis. 13:837-846 (2007).

Kobayashi T., Yuko Iwakami, Tadakazu Hisamatsu, Susumu Okamoto, Toshio lmai, and Toshifumi Hibi. Role of Fractalkine/CX3CR1 in Inflammatory Bowel Disease. The 91st General Meeting of the Japanese Society of Gastroenterology Tokyo, Apr. 14-16, 2005, 37 pages. Abstract No. 250.

Koizumi et al., "Role of CX3CL1/fractalkine in osteoclast differentiation and bone resorption," J Immunol. 183(12):7825-31 (2009).

Kuboi et al., "Chemokine and Inflammatory Bowel Disease," The Medical Frontline. 60(10):134-138 (2005). English language translation provided.

Kuboi Y., Kenzo Muramoto, Uziharu Hishinuma, Miyuki Nishimura, Toshio lmai. Function analysis of fractalkine in concanavalin A-induced hepatitis (ConA hepatitis), The 31st Annual Meeting of the Japanese Society for Immunology, Kobe, Dec. 13, 2001, 25 pages. Abstract No. 3-H-W23-28-O/P.

Kuboi Y., Miyuki Nishimura, Keiko Mizuno, Kouji Morimoto, Kenzo Muramoto, Toshio Imai.Involvement of Fractalkine-CX3CR1 pathway in the development of concanavalin A-induced hepatitis in mice.FOCIS 2004. Canada, Jul. 18-23, 2004, 1 page. Abstract No. W9-16.

Kuboi Y., Miyuki Nishimura, Keiko Mizuno, Toshio lmai, Kenzo Muramoto., Therapeutic effect of anti-Fractalkine/CX3CL1 antibody in mouse inflammatory bowel disease (IBD) model., The 35th Annual Meeting of the Japanese Society for Immunology, Yokohama , Dec. 13, 2005, 26 pages. Abstract No. 1-A-W1-15-P.

Kuboi Y., Nishimura M., Hishinuma I., Imai T., Muramoto K. Involvement of fractalkine-CX3CR1 pathway in the development of concanavalin A-induced hepatitis in mice. Experimental Biology 2002, FASEB Meeting, New Orleans, LA, (2002), 13 pages. Abstract No. 520.3.

Kuboi Y., Nishimura M., Mizuno K., Imai T., Muramoto K. Involvment of fractalkine (FKN)/CX3CL1-CX3CR1 Pathway in the Development of murine experimental colitis model. The 19th Naito Conference, Syonan, Oct. 27, 2005, 18 pages.

Lee et al., "Regulation of autoimmune diabetes by complete freund's adjuvant is mediated by NK cells," J. Immunol. 172:937-942 (2004).

Lirk et al., "Inducible nitric oxide synthase—time for reappraisal," Current Drug Targets—Inflammation & Allergy 1(1):89-108 (2002).

Lo et al., "Natural killer cell degeneration exacerbates experimental arthritis in mice via enhanced interleukin-17 production," Arthritis Rheum. 58(9): 2700-2711 (2008).

Luo et al., "Serologic analysis of the mouse β chemokine JE/monocyte chemoattractant protein-1," J. Immunol. 153:3708-3716 (1994).

Matsui et al., "Identification of novel keratinocyte-secreted peptides dermokine-alpha/-beta and a new stratified epithelium-secreted protein gene complex on human chromosome 19q13.1," Genomics. 84(2):384-97 (2004).

Matsui T, Hayashi-Kisumi F, Kinoshita Y, Katahira S, Morita K, Miyachi Y, Ono Y, Imai T, Tanigawa Y, Komiya T, Tsukita S. Identification of Novel Keratinocyte-secreted Peptides, Dermokine-a/-b, and a New Stratified Epithelium-secreting Protein Gene Complex on Human Chromosome 19q13.1. The Society for Investigative Dermatology Annual meeting , ST. Louis, USA, May 4-7, 2005, 26 pages. Abstract No. 531.

Matsumoto et al., "Role of natural killer cells and TCRγδ T cells in acute autoimmune encephalomyelitis," Eur. J. Immunol. 28: 1681-1688 (1998).

McDermott et al., "Chemokine receptor mutant CX3CR1-M280 has impaired adhesive function and correlates with protection from cardiovascular disease in humans," J. Clin. Invest. 111(8):1241-1250 (2003).

Mikawa et al., "ONO-1714, a nitric oxide synthase inhibitor, attenuates endotoxin-induced acute lung injury in rabbits," Anesth. Analg. 97(6):1751-1755 (2003).

Minaki, "Migrating postmitotic neural precursor cells in the ventricular zone extend apical processes and form adherens junctions near the ventricle in the developing spinal cord," Neurosci Res. 52(3):250-62 (2005).

Miyuki et al., "Fractalkine," Inflammation and Immunity. 11(4):435-442 (2003). English language translation provided.

Mizuno et al., "Production and neuroprotective functions of fractalkine in the central nervous system," Brain Res. 979(1-2):65-70 (2003).

Mizuno K, Ogasawara H, Inoue Y, Nishimura M, Imai T. Identification of a novel Fc receptor gamma-chain-associated receptor, TARM (T Cell-interacting Activating Receptor on Myeloid Cells), expressed on dendritic cells. The 18th Naito Conference "Medicine and Biology of Innate Immunity, II", Shonan, Oct. 27, 2005, 17 pages. Abstract No. PS [II]-37.

Mizuno K., Hideaki Ogasawara, Yoko Inoue, Miyuki Nishimura, Toshio lmai., Identification and function analysis of the new activating receptor TARM expressed in dendritic cells., The 35th Annual Meeting of the Japanese Society for Immunology, Yokohama, Dec. 13-15, 2005, 4 pages. Abstract No. 2-B-W21-17-P.

Mizutani et al., "Dose-dependent differential regulation of cytokine secretion from macrophages by fractalkine," J Immunol. 179(11):7478-87 (2007).

Mizutani N, Kawashima R, Kawamura Y, lmai T, Toyama-Sorimachi N, Dohi T. Fractalkine negatively regulates macrophage function. The 36th Annual Meeting of The Japanese Society for Immunology, Osaka, Dec. 11-13. 2006, 2 pages. Abstract No. 3-H-W44-15-OP.

Morimoto et al., "Interaction of cancer cells with platelets mediated by Necl-5/poliovirus receptor enhances cancer cell metastasis to the lungs," Oncogene. 27(3):264-73 (2008).

Morimoto K., Keiko Satoh, Yoko Inoue, Akiko Hamaguchi, Masakazu Takeuchi, Wataru Ikeda, Yoshimi Takai, Toshio Imai. Necl-5 Role of Nectin-like molecule-5/Poriovirus repeptor/CD155 on tumor metastasis into the lung. The 57th Japan Society for Cell Biology, Osaka, May 26, 2004, 22 pages. Abstract No. 1 P-107.

Morimoto K., Keiko Yamaguchi, Akiko Hamaguchi, Yoko Inoue, Masayuki Okada, Toshio Imai. Involvement of the binding of Necl-5/CD155 and DNAM-1/CD226 in the cellular adhesion of cancer cell and platelet, and lung metastasis. The 35th Annual Meeting of The Japanese Society for Immunology, Yokohama, Dec. 13-15, 2005, 39 pages. Abstract No. 1-I-W16-25-P.

Morimoto K., Masayuki Okada, Wataru Ikeda, Yoshimi Takai, Toshio Imai. Role of Nectine-like molecule-5/Tage4/PVR/CD155 in lung metastatis of colon adenocarcinoma The 64th Annual Meeting of the Japanese Cancer Association, Sapporo, Jul. 14-16, 2005, 37 pages. Abstract No. PA1-0152.

(56) References Cited

OTHER PUBLICATIONS

Morimoto K., Shoichi Takeuchi, Miyuki Nishimura, Yoko Inoue, Yuichi Ono, Toshio Imai, Yoshimi Takai. Analysis of tight junction constituent molecules by pre-embedding immunoelectron microscope method. The 19th Annual Meeting of Japanese Society of Electron Microscopy Technology for Medicine and Biology, Tokyo, Apr. 26-27, 2003, 3 pages. Abstract No. 14.

Morimoto K., Shoichi Takeuchi, Miyuki Nishimura, Yoko Inoue, Yuichi Ono, Toshio Imai, Yoshimi Takai.Characterization analysis of JEAP2, a TJ molecule specific for exocrine gland. The 25th Annual Meeting of The Molecular Biology Society of Japan, Yokohama, Dec. 13-14, 2002, 2 pages. Abstract No. 2P-0752.

Muehlhoefer et al., "Fractalkine is an epithelial and endothelial cell-derived chemoattractant for intraepithelial lymphocytes in the small intestinal mucosa," J. Immunol. 164:3368-3376 (2000).

Murai et al., "Active participation of $CCR5^+CD8^+$ T lymphocytes in the pathogenesis of liver injury in graft-versus-host disease," J. Clin. Invest. 104(1):49-57 (1999).

Murai et al., "Peyer's patch is the essential site in initiating murine acute and lethal graft-*versus*-host reaction," Nature Immunol. 4(2):154-60 (2003).

Muramoto K, Kuboi Y, Nishimura M, Ogasawara H, Mizuno K, ImaiT."The pathway of CX3CR1 and fractalkine interaction is involved in the leukocytes infiltration on experimental autoimmune encephalomyelitis in mice." International Congress of Neuroimmunology, Oct. 26, 2008, 2 pages.

Muramoto K, Kuboi Y, Ogasawara H, Inoue Y, Mizuno K, Rikitsu E, Nishimura M, Imai T. Blockade of CX3CR1 and fractalkine interaction ameliorates experimental autoimmune encephalomyelitis in mice. The 13th International Congress of Immunology, Rio de Janeiro, Brazil, Aug. 21-25, 2007, 10 pages.

Muramoto, "Pharmacological action of Iguratimod, a novel antirheumatic drug, Crosstalk between nervous system and immunological system", National Meeting for Directors of Pharmacy, Jun. 14, 2013, 90 pages.

Muramoto K., "Drug development in autoimmune disorder field (mainly preclinical development)", Lecture Meeting of Raqualia, Autoimmne Disease Symposium, Jun. 21, 2013, 108 pages.

Muramoto K., "Recent topics of autoimmune disorder, and crosstalk with nervous system (Cause and treatment)", Lecture in Kitazato University, May. 19, 2012, 65 pages.

Muramoto K., Kenichi Tanaka EP4 and CX3CR1 regulate both immune and pain responses in mice-Immunoregulatory moleclules reveal crosstalk between immune and pain responses-, Annual Meeting of The Japanese Pharmacological Society, (2012), 23 pages.

Muramoto K., Kenichi Tanaka., Pharmacological and Clinical Effect of Iguratimod (T-614), an Anti-rheumatic Drug., Annual Meeting of The Japanese Pharmacological Society, Mar. 2013, 22 pages.

Müller-Ladner et al., "Demonstration of granzyme A and perforin messenger RNA in the synovium of patients with rheumatoid arthritis," Arthritis Rheum. 38(4): 477-484 (1995).

Nagamoto et al., "OPC-6535 inhibits human and porcine monocyte tumor necrosis factor-alpha production in vitro and in invo," Gastroenterology. 126(4):A512-585 (2004). Abstract No. W1090.

Nagata et al., "Evidence for the role of $CD8^+$ cytotoxic T cells in the destruction of pancreatic β-cells in nonobese diabetic mice," J. Immunol. 152:2042-2050 (1994).

Nagata et al., "Selective Expression of a Novel Surface Molecule by Human Th2 Cells In Vivo," J Immunol. 162(3):1278-86 (1999).

Nagi T., Toshio lmai, Kenji Nagasaka, Miki Nonomura, Akira Taniguchi, Kenji Hayashida, Jun Hasegawa, Osamu Yoshie, Nobuyuki Miyasaka. T cell infiltration into synovial tissue of chronic rheumatoid arthritis (RA) by CX3CL1/CX3CR1 interaction. The 67th Annual Meeting of the Japanese Society for Interferon & Cytokine Research, Tokyo (2002), 14 pages. Abstract No. B-6.

Nagi T., Toshio lmai, Peter E. Lipsky, Nobuyuki Miyasaka.Analysis of chemokine involved in infiltration of T cell into synovial tissue of chronic rheumatoid arthritis. The 23rd Annual Meeting of the Japanese Society of Inflammation and Regeneration, Tokyo, Jul. 2-3, 2002, 21 pages. Abstract No. W6-3.

Nagira et al., "A lymphocyte-specific CC chemokine, secondary lymphoid-tissue chemokine (SLC) is a highly efficient chemoattractant for B cells and activated T cells," Eur J Immunol. 28(5):1516-23 (1998).

Nagira et al., "Enhanced HIV-1 replication by chemokines constitutively expressed in secondary lymphoid tissues," Virology. 264(2):422-6 (1999).

Nagira et al., "Molecular cloning of a novel human CC chemokine secondary lymphoid-tissue chemokine that is a potent chemoattractant for lymphocytes and mapped to chromosome 9p13," J Biol Chem. 272(31):19518-24 (1997).

Nagira et al., "Mouse homologue of C33 antigen (CD82), a member of the transmembrane 4 superfamily: complementary DNA, genomic structure, and expression," Cell Immunol. 157(1): 144-57 (1994).

Naito et al., "A novel potent inhibitor of inducible nitric oxide inhibitor, ONO-1714, reduces intestinal ischemia-reperfusion injury in rats," Nitric Oxide. 0(3):170-7 (2004).

Naito et al., "The inducible nitric oxide synthase inhibitor ONO-1714 blunts dextran sulfate sodium colitis in mice," Eur. J. Pharmacol. 412:91-99 (2001).

Nakai K., Yutaka Nagano, Hisanori Umehara, Toshio lmai, Hideto Sano, Masayuki Yokoide, Michiharu Daito, Nao Okubo, Naochika Domae.lnvolvement of fractalkine in formation of atherosclerotic lesions. The 33rd Annual Scientific Meeting of the Japanese Atherosclerosis Society, Tokyo, Jun. 7-8, 2001, 2 pages. Abstract No. P009.

Nakajima et al., "Intracellular localization and release of eotaxin from normal eosinophils," FEBS Lett. 434(3):226-30 (1998).

Nakajima T., Shin Takagi, Toshio Imai, Osamu Yoshie., Cloning of human eotaxin gene and identification of its receptor CC CKR3., The 26th Annual Meeting of The Japanese Society for Immunology, Yokohama, Nov. 27, 1996, 2 pages. Abstract No. 2P4-23.

Nakatani K., Hiroshi Fujii, Miho Terada, Norimasa Arita, Toshio lmai, Hideo Shiiki, Kazuhiro Doi, Masato Nose. Involvements of fractalkine in lupus nephritis model mouse MRL/lpr., The 43rd Annual Meeting of the Japanese Society of Nephrology, May 2000, 2 pages. Abstract No. O-341.

Nakatani K., Hiroshi Fujii, Miho Terada, Norimasa Arita, Toshio lmai, Masato Nose., Analysis of adhesion molecules of glomerular vascular endothelial cell in lupus nephritis model mouse by microdissection., The 73rd Annual Meeting of The Japanese Pharmacological Society, Mar. 10, 2000, 3 pages. Abstract No. 3-am-m13.

Nakatani K., Hiroshi Fujii, Miho Terada, Norimasa Arita, Toshio lmai, Masato., Nose.lnvolvements of adhesion molecule and fractalkine in lupus nephritis model mouse., The 21st Annual Meeting of the Japanese Society of Inflammation, Tokyo, Jul. 4, 2000, 2 pages.

Namekawa et al., "Functional subsets of CD4 T cells in rheumatoid synovitis," Arthritis Rheum. 41(12): 2108-2116 (1998).

Nanki et al., "Migration of CX3CR1-positive T cells producing type 1 cytokines and cytotoxic molecules into the synovium of patients with rheumatoid arthritis," Arthritis Rheum. 46(11):2878-83 (2002).

Nanki T., Toshio lmai, Kenji Nagasaka, Miki Nonomura, Akira Taniguchi, Kenji Hayashida, Jun Hasegawa, Nobuyuki Miyasaka. Infiltration of T cell into synovial tissue of chronic rheumatoid arthritits (RA) by CX3CL1/CX3CR1 interaction, The 46th Annual General Assembly and Scientific Meeting of the Japan College of Rheumatology, Apr. 2002, 22 pages. Abstract No. 49-3.

Nanki T., Toshio Imai, Kenji Nagasaka, Yoshinori Nonomura, Ken Taniguchi, and Nobuyuki Miyasaka. Migration of CX3CR1+ T cells producing Th1- or Tc1-type cytokines and granzyme A, into the synovium of patients with rheumatoid arthritis: Lymphocyte subsets and chemokine receptors. The 31st Annual Meeting of The Japanese Society for Immunology, Kobe, Dec. 11, 2001, 18 pages. Abstract No. 1-D-W3-10-P.

Nanki T., Yasuyo Urasaki, Toshio Imai, Kenzo Muramoto, Tetsuo Kubota, Nobuyuki Miyasaki., Analysis of the arthritis-suppressing effect by anti-fractalkine (FKN: CX3CL1) antibody., the 33th Annual Meeting of The Japanese Society for Immunology, Fukuoka, Dec. 9, 2003, 4 pages. Abstract No. 2-I-W28-46-P.

Niess et al., "$CX_3CR1$-Mediated Dendritic Cell Access to the Intestinal Lumen and Bacterial Clearance" Science. 307:254-8 (2005).

(56) References Cited

OTHER PUBLICATIONS

Nishimura et al., "Chemokines as Novel Therapeutic Targets for Inflammatory Bowel Disease," Contemporary Challenges in Autoimmunity: Ann NY Aced Sci. 1173:350-6 (Review) (2009).
Nishimura et al., "Dual functions of fractalkine/CX3C ligand 1 in trafficking of perforin+/granzyme B+ cytotoxic effector lymphocytes that are defined by CX3CR1 expression," J Immunol. 168(12):6173-80 (2002).
Nishimura et al., "JEAP: A novel component of tight junctions in exocrine cells," J Biot Chem. 277(7):5583-7 (2002).
Nishimura M, Kuboi Y, Muramoto K, Mizuno K, Imai T. Involvement of Fractalkine-CX3CR1 pathway in the development of concanavalin A-induced hepatitis in mice. The 13th International Congress of Immunology, Rio de Janeiro, Brazil, Aug. 21-25, 2007, 18 pages.
Nishimura M, Kuboi Y, Muramoto K, Mizuno K, Ogasawara H, Imai T. "Blockade of CX3CR1 and fractalkine interaction ameliorates inflammatory bowel diseases in mice." Autoimmunity congress 2008, Porto, Portugal, Sep. 10-14, 2008 (Oral presentation), 2 pages. Abstract No. 517.
Nishimura M, Mizuno K, Hamaguchi a, Imai T. Selective expression of CX3CR1 on donor cytotoxic effector T cells in acute GVHD mice. FOCIS 2004. Canada, Jul. 18-23, 2004, 17 pages. Abstract No. W9-24.
Nishimura M, Umehara H, Nakayama T, Yoneda O, Hieshima K, Kakizaki M, Dohmae N, Yoshie O, lmai T. "Role of fractalkine/ CX3CL1 in trafficking of circulating cytotoxic effector lymphocytes that are defined by CX3CR1 expression." Experimental Biology 2002, FASEB Meeting, New Orleans, LA (2002), 21 pages. Abstract No. 924.14.
Nishimura M., Akiko Hamaguchi, Koji Morimoto, Keiko Mizuno, Toshio Imai."The CX3CR1 expression in donor derived CD8$_+$ T cell in the case of mouse acute GVHD model." The 32nd Annual Meeting of The Japanese Society for Immunology, Tokyo, Dec. 5, 2002, 32 pages. Abstract No. 2-D-W23-22-O/P.
Nishimura M., Kenzo Muramoto, Toshio Imai. "Analysis of fractalkine/CX3CR1 in mouse lymphocyte." The 31st Annual Meeting of The Japanese Society for Immunology, Kobe, Dec. 13, 2001, 33 pages. Abstract No. 3-H-W23-15-P.
Nishimura M., Mayumi Asano(Kakizaki), Yuichi Ono, Koji Morimoto, Shoichi Takeuchi, Yoko Inoue, Toshio Imai, Yoshimi Takai. "Identification of novel tight junction protein JEPA by localization of GFP fusion protein as an indicator." The 25th Annual Meeting of The Molecular Biology Society of Japan, Yokohama, Dec. 13-14, 2002, 22 pages. Abstract No. 2P-0751.
Nishimura M., Osamu Yoneda, Hisanori Umehara, Naochika Domae, Toshio Imai, Osamu Yoshie., "Analysis of CX3CR1, a fractalkine receptor selectively expressed in effector killer lymphocyte." The 30th Annual Meeting of The Japanese Society for Immunology, Symposium, Sendai, Nov. 15, 2000, 23 pages. Abstract No. 2-F-270-P/O.
Nishimura M., Yoshikazu Kuboi, Keiko Mizuno, Kenzo Muramoto, Toshio Imai., "Analysis of the concanavalin A-induced hepatitis (ConA hepatitis) suppression mechanism by anti-fractalkine antibody." The 33th Annual Meeting of The Japanese Society for Immunology, Fukuoka, Dec. 9, 2003, 29 pages. Abstract No. 2-J-W29-3-O/P.
Nishimura M., Yoshikazu Kuboi, Keiko Mizuno, Koji Morimoto, Kenzo Muramoto, Toshio Imai. "Roles of CX3CR1 positive macrophage in ConA hepatitis." The 35th Annual Meeting of The Japanese Society for Immunology, Yokohama, Dec. 13-15, 2005, 18 pages. Abstract No. 2C-W22-18-P.
Nishioka (Fusaoka) E., Tomohiro Yamada, Eriko Rikitsu, Miyuki Nishimura, Akiko Katagiri, Tatsuo Kinashi, Toshio lmai. "AMICA, and adhesion molecule interacting with CAR, enhances lymphocyte transmigration by activating LFA-1." The 38th Annual Meeting of The Japanese Society for Immunology, Kyoto, Dec. 1-3, 2008, 19 pages. Abstract No. 1-A-W2-3-O/P.
Nishioka (Fusaoka) R., Etsuko Chikaratsu (Takao), Kenzo Muramoto, Tomohiro Yamada, Yoko Inoue, Miyuki Nishimura, Toshio Imai., "Cell adhesion molecule AMICA induces cell infiltration via the PI 3-kinase binding region." The 33rd Annual Meeting of the Japanese Society of Inflammation and Regeneration, Fukuoka, Jul. 5-6, 2012, 19 pages. Abstract No. P6-6.
Nishioka E, Nishimura M, Katagiri K, Kinashi T, Imai T. "Cell adhesion molecule AMICA enhances transendothelial migration of human activated T cells." 14th International Congress of Immunology, Kobe, Aug. 23-27, 2010, 13 pages. Abstract No. PP-028-20.
Nomiyama et al., "Assignment of the human CC chemokine gene TARC (SCYA17) to chromosome 16q13," Genomics. 40(1):211-3 (1997).
Nomiyama et al., "Assignment of the human CC chemokine MPIF-2/eotaxin-2 (SCYA24) to chromosome 7q11.23," Genomics. 49(2):339-40 (1998).
Nomiyama et al., "Human chemokines fractalkine (SCYD1), MDC (SCYA22) and TARC (SCYA17) are clustered on chromosome 16q13," Cytogenet Cell Genet. 81(1): 10-1 (1998).
Nomiyama et al., "The human CC chemokine TECK (SCYA25) maps to chromosome 19p13.2," Genomics. 51(2):311-2 (1998).
Oda K., Hirofumi Utsu, Kaori Ohno, IkkoTabunoki, Akihiko Ohshige, Dai Imanaka, Kotaro Kumagai, Seiichi Mawatari, Tsutomu Tamai, Akihiro Moriuchi, Shin Oketani, Akio Ido, Takashi Ohara, Tetsu Kawano, Hirohiro Tsubouchi., Serum Fractalkine concentration in autoimmune disorder patients., The 49th General Meeting of the Japan Society of Hepatology., Shinjuku, Jun. 2013, 4 pages. Abstract No. O-118.
Ohmori et al., "Identification of cutaneous lymphocyte-associated antigen as sialyl 6-sulfo Lewis X, a selectin ligand expressed on a subset of skin-homing helper memory T cells," Blood. 107(8):3197-204 (2006).
Ohtani et al., "Infiltration of CD8$_+$ T-cells containing RANTES/ CCL5$_+$ cytoplasmic granules in actively inflammatory lesions of human chronic gastritis," Lab Invest. 84(3):368-375 (2004).
Omori K., Chikako Mitsuoka, Mineko Izawa, Akiko Kanamori, Toshio Imai, Osamu Yoshie, Hitoshi Hasegawa, Tsunaharu Matsushima, Reiji Kanagi., "Sialyl 6-Sulfo Lex, a selectin ligand acting specifically for T-lymphocyte routine homing in normal subject." The 30th Annual Meeting of The Japanese Society for Immunology, Symposium, Sendai, Nov. 15, 2000, 3 pages. Abstract No. 2-F-285-P.
Omori K., Toshio lmai, Osamu Yoshie, Tsunaharu Matsushima, Mineko Izawa, Shinko Kanamori, Reiji Kanaki. "Sialyl 6-Sulfo Lewis x as biochemical substance of specific marker cutaneous lymphocyte antigen of skin-homing helper-memory T cell subset." The 32nd Annual Meeting of The Japanese Society for Immunology, Tokyo, Dec. 5, 2002, 2 pages. Abstract No. 2-D-W24-7-O/P.
Ono et al., "Differences in neurogenic potential in floor plate cells along an anteroposterior location: midbrain dopaminergic neurons originate from mesencephalic floor plate cells," Development. 134(17):3213-25 (2007).
Ooshio et al., "Involvement of LMO7 in the association of two cell-cell adhesion molecules, nectin and E-cadherin, through afadin and alpha-actinin in epithelial cells," J Biol Chem. 279(30):31365-73 (2004).
Osada et al., "Expression of MAEG, a novel basement membrane protein, in mouse hair follicle morphogenesis," Exp Cell Res. 303(1):148-159 (2005).
Parmentier et al., "Selective inhibition of inducible nitric oxide synthase prevents ischaemic brain injury," British Journal of Pharmacology 127(2):546-552 (1999).
Patel et al., "Chemokines have diverse abilities to form solid phase gradients," Clin Immunol. 99(1):43-52 (2001).
Pelletier et al., "Reduced progression of experimental osteoarthritis in vivo by selective inhibition of inductible nitric oxide synthase," Arthritis Rheum. 41(7): 1275-1286 (1998).
Poon et al., "Complexity of inducible nitric oxide synthase cellular source determines benefit versus toxicity," Circulation 108(9):1107-1112 (2003).
Proceedings of the Japanese Society for Immunology, 30:192 (2000). Abstract 2-F-270-P/O. English language translation provided.
Proceedings of the Japanese Society for Immunology, 33 (2003). Abstract No. 2-I-W28-46-P. Concise explanation in English language provided.

(56) References Cited

OTHER PUBLICATIONS

Rafi-Janajreh et al., "Role of CD44 in CTL and NK cell activity," Front. Biosci. 3:665-671 (1998).
Raport et al., "The orphan G-protein-coupled receptor-encoding gene V28 is closely related to genes for chemokine receptors and is expressed in lymphoid and neural tissues," Gene 163:295-299 (1995).
Rimaniol et al., "The $CX_3C$ chemokine fractalkine in allergic asthma and rhinitis," Journal of Allergy and Clinical Immunology. 112(6):1139-46 (2003).
Robinson et al., "A role for fractalkine and its receptor ($CX_3CR1$) in cardiac allograft rejection," J. Immunol. 165:6067-6072 (2000).
Ruth et al., "Fractalkine, a novel chemokine in rheumatoid arthritis and in rat adjuvant-induced arthritis," Arthritis Rheum. 44(7): 1568-1581 (2001).
Sakurai et al., "Nitric oxide production and inducible nitric oxide synthase expression in inflammatory arthritides," J. Clin. Invest. 96:2357-2363 (1995).
Sallusto et al., "Two subsets of memory T lymphocytes with distinct homing potentials and effector functions," Nature. 401(6754):708-12 (1999).
Sans et al., "Enhanced recruitment of $CX3CR1_+$ T cells by mucosal endothelial cell-derived fractalkine in inflammatory bowel disease," Gastroenterology 132(1):139-153 (2007).
Santos et al., "Suppression of adjuvant arthritis and synovial macrophage inducible nitric oxide by n-iminoethyl-l-ornithine, a nitric oxide synthase inhibitor," Inflammation. 21(3):299-311 (1997).
Sasai K., Machiko Itoh, Tomoo Itoh, Toshio Imai, Tsuyoshi Akagi. "DeltaNp63 is one of the determinant factors in the histology of Lung Cancer." The 71st Annual meeting of the Japanese Cancer Association Sapporo, Sep. 19-21, 2012, 10 pages. Abstract No. J-2088.
Sass et al., "Inducible nitric oxide synthase is critical for immune-mediated liver injury in mice," J. Clin. Invest. 107(4):439-447 (2001).
Satoh K., Miyuki Nishimura, Toshio Imai. "A novel counter ligand for coxsackie and adenovirus receptor(CAR), CARL, preferentially expressed on Th1 cells." The 35th Annual Meeting of the Japanese Society for Immunology, Sapporo, Dec. 1, 2004, 32 pages. Abstract No. 1 P-111.
Satoh K., Yoko Inoue, Akiko Hamaguchi, Koji Morimoto, Masakazu Takeuchi, Miyuki Nishimura, Toshio Imai. "A novel counter ligand for coxsackie and adenovirus receptor (CAR), CARL, preferentially expressed on Th1 cells." The 57th Japan Society for Cell Biology, Osaka, May 26, 2004, 13 pages. Abstract No. 1P-111.
Satoh-Yamaguchi K, Inoue Y, Rikitsu E, Fusaoka E, Nishimura M, lmai T. AMICA-CAR interaction stimulates the transmigration of Th1 cells by forming a migratory ring-like architecture. The 13th International Congress of Immunology, Rio de Janeiro, Brazil, Aug. 21-25, 2007, 18 pages.
Sawai et al., "T cell costimulation by fractalkine-expressing synoviocytes in rheumatoid arthritis," Arthritis Rheum. 52(5):1392-1401 (2005).
Schäfer et al., "Novel role of the membrane-bound chemokine fractalkine in platelet activation and adhesion," Blood 103(2):407-12 (2004).
Serbina et al., "TNF-iNOS-producing dendritic cells mediate innate immune defense against bacterial infection," Immunity 19(1):59-70 (2003).
Shi et al., "Innate Immunity and autoimmunity: from self-protection to self-destruction." TRENDS in Immunololgy. 22(2):97-101 (2001).
Shi et al., "Natural killer cells determine the outcome of B cell-mediated autoimmunity," Nature Immunol. 1(3):245-51 (2000).
Shingai et al., "Implications of nectin-like molecule-2/IGSF4/RA175/SgIGSF/TSLC1/SynCAM1 in cell-cell adhesion and transmembrane protein localization in epithelial cells," J Biol Chem. 278(37):35421-7 (2003).
Shingai et al., "Roles and Modes of Action of Cell Adhesion Molecule Nectin in Invasion and Metastasis of Cancer Cells," Molecular Target Treatment of Cancer. 1(2):16-23 (2003). English language translation provided.
Shingai T., Wataru Ikeda, Shigeki Kakunaga, Kyoji Takekuni, Koji Morimoto, Keiko Satoh, Masakazu Takeuchi, Toshio Imai, Yoshimi Takai., "Nectin-like molecule (necI)-2/TSLC1/SynCAM1: Localization at the basolateral plasma membrane of epithelial cells excluding cell-cell junctions and binding of Pals2." The 62nd Annual Meeting of the Japanese Cancer Association, Nagoya, Sep. 25-27, 2003, 18 pages. Abstract No. 1475-PA.
Shoudai et al., "Isolation of cDNA encoding a novel human CC chemokine NCC-4/LEC," Biochim Biophys Acta. 1396(3):273-7 (1998).
Soriano et al., "Mice deficient in fractalkine are less susceptible to cerebral ischemia-reperfusion injury," J. Neuroimmunol. 125:59-65 (2002).
Sozzani et al., "Differential regulation of chemokine receptors during dendritic cell migration: a model for their trafficking properties," J Immunol. 161(3):1083-6 (1998).
Spaeny-Dekking et al., "Extracellular granzymes A and B in humans: detection of native species during CTL responses in vitro and in vivo," J. Immunol. 160:3610-3616 (1998).
Sugihara-Mizuno et al., "Molecular characterization of angiomotin/JEAP family proteins: interaction with MUPP1/Patj and their endogenous properties." Genes Cells. 12(4):473-86 (2007).
Suzuki et al., "Serum level of soluble CX3CL1/fractalkine is elevated in patients with polymyositis and dermatomyositis, which is correlated with disease activity," Arthritis Research & Therapy. 14(2):176-85 (2012).
Suzuki F., Toshihiro Minamiki, Toshi Imai, Hirotoshi Kikuchi, Toshinari Hirobatake, Hitoshi Uesaka, Nobuyuki Miyasaka., "Suppression of experimental polymyositis by anti-fractalkine (FKN) antibody." The 49th Annual General Assembly and Scientific Meeting of the Japan College of Rheumatology, Yokohama, Apr. 26-29, 2005, 4 pages. Abstract No. S9-4.
Tagi et al., "Dermokine as a novel biomarker for early-stage colorectal cancer." J Gastroenterol. 45(12):1201-1 1 (2010).
Takagi et al., "Identification of a highly specific surface marker of T-cell acute lymphoblastic leukemia and neuroblastoma as a new member of the transmembrane 4 superfamily," Int J Cancer. 61(5):706-15 (1995).
Takagi S., Toshio Imai, Osamu Yoshie., "Structure of novel C type chemokine SCM-1/Lymphotactin gene." The 26th Annual Meeting of The Japanese Society for Immunology, Yokohama, Nov. 27, 1996, 2 pages. Abstract No. 2P4-22.
Takashima K., Eri Nishioka, Masato Hoshino, Kentaro Uesugi, Naoto Yagi, Toshio Imai, Atsushi Nakahira, Masahiro Kohzuki, Noriko Osumi, Hiroshi Onodera. "Poly glycolic acid scaffold with micro-braiding process promotes axonal regeneration after spinal cord injury." The 34th Annual Meeting of the Japan Neuroscience Society, Yokohama Sep. 14-17, 2011, 3 pages.
Takashima K., Eri Nishioka, Masato Hoshino, Yusuke Kawabe, Kentaro Uesugi, Naoto Yagi, Toshio Imai, Atsushi Nakahira, Masahiro Kohzuki, Noriko Osumi, Hiroshi Onodera., "Implantation of biodegradable intelligent-scaffold with micro-braiding process for CNS repair." The 33th Annual Meeting of the Japanese Society for Biomaterials., Kyoto, Nov. 21-22, 2011, 6 pages. Abstract No. P119.
Takebe A., Takumi Era, Yuichi Ono, Toshio Imai, Shinichi Nishikawa. "A new approach for analysis of genetic program during an early mesodermal development." Workshop for particular young researchers on cancer, Tateshina (2002), 2 pages.
Takeuchi K., Wataru Ikeda, Shigeki Kakunaga, Koji Morimoto, Keiko Satoh, Masakazu Takeuchi, Toshio Imai, Yoshimi Takai. "Nectin-like molecule(NecI)-5/Tage4(1): Enhancement of cancer cell mortility by heterophilic trans-interaction with Nectin-3." The 62nd Annual Meeting of the Japanese Cancer Association, Nagoya, Sep. 25-27, 2003, 12 pages. Abstract No. 1096-OA.
Tanaka et al., "Selective expression of liver and activation-regulated chemokine (LARC) in intestinal epithelium in mice and humans," Eur J Immunol. 29(2):633-42 (1999).
Tasaki et al., "Chemokine PARC Gene (SCYA18) Generated by Fusion of Two MIP-1alpha/LD78alpha-like Genes," Genomics. 55(3):353-7 (1999).
Tasaki Y., Kusuo Hieshima, Toshio Imai, Masataka Baba, Masayoshi lio, Retsu Miura, Osamu Yoshie, and Hisayuki Nomiyama., "Molecular cloning of Human CC chemokine PARC cDNA and

(56) References Cited

OTHER PUBLICATIONS

Characterization of Its Gene." The 20th Annual Meeting of The Molecular Biology Society of Japan, Kyoto, Dec. 17, 1997, 3 pages. Abstract No. 2-157-P-329.

Toyabe et al., "Requirement of IL-4 and liver NK1$^+$ T cells for concanavalin A-induced hepatic injury in mice," J. Immunol. 159:1537-1542 (1997).

Ueda et al., "Expression of the KAI1 protein in benign prostatic hyperplasia and prostate cancer," Am J Pathol. 149(5):1435-40 (1996).

Ueha et al., "Intervention of MAdCAM-1 or fractalkine alleviates graft-versus-host reaction associated intestinal injury while preserving graft-versus-tumor effect," Journal of Leukocyte Biology. 81(1):176-85 (2007).

Uehane S., Masako Murai, Hiroyuki Yoneyama, Masahiro Kitabatake, Shigeto Hontsu, Toshio lmai, Sho Ishikawa, Koji Matsushima., Analysis of the donor T cell infiltration mechanism in intestinal tract GVHD., The 33th Annual Meeting of The Japanese Society for Immunology, Fukuoka, Dec. 8, 2003, 10 pages. Abstract No. 1-C-W4-8-O/P.

Uehane S., Masako Murai, Hiroyuki Yoneyama, Masahiro Kitabatake, Shigeto Hontsu, Toshio Imai, Takashi Shimaoka, Shin Yonehara, Sho Ishikawa, Koji Matsushima., Potential of the avoidance of intestinal tract GVHD and of GVT inducement with α4β7-MAdCAM-1 and CX3CR1-fractalkine as the targets., The 34th Annual Meeting of The Japanese Society for Immunology, Sapporo, Dec. 2, 2004, 11 pages. Abstract No. 2-B-W19-05-O/P.

Uehane S., Masako Murai, Hiroyuki Yoneyama, Masahiro Kitabatake, Shigeto Hontsu, Toshio Imai, Takeshi Shimaoka, Shin Yonehara, Sho Ishikawa, Koji Matsushima., Potential of selective suppression of cell migration-targeted intestinal tract GVHD., The 25th Annual Meeting of The Japanese Society of Inflammation and Regeneration,Tokyo, Jul. 13, 2004, 12 pages. Abstract No. 160.

Umehara et al., "Fractalkine and Vascular Injury from Basic Research to Clinical Manifestations," Inflammation and Immunity. 12(6): 735-742 (2004). English language translation provided.

Umehara et al., "Fractalkine and vascular injury," Trends Immunol. 22(11):602-7 (2001).

Umehara et al., "Fractalkine in Vascular Biology. From Basic Research to Clinical Disease," Arterioscler Thromb Vasc Biol. 24(1):34-40 (2004).

Umehara et al., "Fractalkine, a CX3C-chemokine, functions predominantly as an adhesion molecule in monocytic cell line THP-1," Immunol Cell Biol. 79(3):298-302 (2001).

Umehara et al., "Fractalkine: Basic research and clinical relevance," Rinsho Meneki. 35(3):353-359 (2001). English language translation.

Umehara et al., "Involvement of fractalkine in interaction with vascular endothelial cells and lymphocytes," Rinsho Meneki. 40(4):371-378 (2003). English language translation provided.

Umehara et al., "Role of fractalkine in leukocyte adhesion and migration and in vascular injury," Drug News Perspect. 14(8):460-4 (2001).

Umehara H., Miyuki Nishimura, Naochika Domae, Tsuneyo Mimori, Osamu Yoshie, Toshio Imai. Fractalkine as the gatekeeper for cytotoxic lymphocytes. The 32nd Annual Meeting of The Japanese Society for Immunology, Symposium, Tokyo, Dec. 5 2002, 3 pages. Abstract No. S5-6.

Umehara H., Osamu Yoneda, Hitoshi Inoue, Seiji Aida, Toshio Ima, Naochika Domae. The molecular mechanism of vessel inflammation and vascularization: Fractalkine and angiitis., The 21st Annual Meeting of the Japanese Society of Inflammation, Symposium, Tokyo, Jul. 5, 2000, 2 pages. Abstract No. SY2-5.

Umehara H., Osamu Yoneda, Miyuki Nishimura, Satohiko Miyazi, Hiroshi Inoue, Seiji Aida, Naochika Domae, Tsuneyo Mimori, Osamu Yoshie, Toshio Imai. Significance of fractalkine in adhesion of lymphocyte and vascular endothelial cell. The 32nd Annual Meeting of The Japanese Society for Immunology, Tokyo, Dec. 5, 2002, 3 pages. Abstract No. 2-D-W24-160/P.

Umehara H., Seiji Aida, Osamu Yoneda, Hitoshi Inoue, Toshio Imai, Osamu Yoshie, Hisao Imai, Naochika Domae., Function of fractalkine, an adhesive chemokine in adhesion, of monocyte and vascular endothelial cell.The 30th Annual Meeting of The Japanese Society for Immunology, Symposium, Sendai, Nov. 15, 2000, 3 pages. Abstract No. 2-F-271-P.

Umehara H., Toshio Imai, Hajime Yoshifuji, Daisuke Kawabata, Yoshitaka Imura, Yoshimasa Fujita, Masao Tanaka, Takao Fujii, Tsuneyo Mimori. IFN-γ production of NK cell and Th1 response by Fractalkine. The 47th Annual General Assembly and Scientific Meeting of the Japan College of Rheumatology, Tokyo, Apr. 2003, 2 pages. Abstract No. W 34-4-O/P.

Umehara H., Toshio Imai, Masao Tanaka, Takao Fujii, Tsuneyo Mimori.Vascular endothelial cell injury by fractalkine. The 46th Annual General Assembly and Scientific Meeting of the Japan College of Rheumatology, Apr. 2002, 2 pages. Abstract No. W49-5.

Umehara H., Toshio Imai, Miyuki Nishimura, Hitoshi Inoue, Tadahiko Miyazi, Osamu Yoneda, Naochika Domae, Tsuneyo Mimori. Fractalkine and vascular endothelial injury. The 29th Annual Meeting of the Japanese Society for Clinical Immunology, Osaka, Dec. 10-11, 2001, 2 pages. Abstract No. 3-1w.

Umehara H., Toshio Imai, Tsuneyo Mimori. Physiological activity and clinical significance of fractalkine.The 23rd Annual Meeting of the Japanese Society of Inflammation and Regeneration, Tokyo, Jul. 2-3, 2002, 2 pages. Abstract No. W-6-2.

Urasaki Y., Toshihiro Nangi, Toshio Imai, Kenzo Muramoto, Tetsuro Kubota, Nobuyuki Miyasaka. Examination on arthritis inhibitory effects by anti-fractalkine (CX3CL1) antibody. The 47th Annual General Assembly and Scientific Meeting of the Japan College of Rheumatology, Tokyo, Apr. 2003, 22 pages. Abstract No. W 35-8-O/P.

Vestergaard C., Hiroyuki Yoneyama, Masako Murai, Koichiro Nakamura, Kunihiko Tamaki, Yuya Terashima, Toshio Imai, Osamu Yoshie, Tatsuro Irimura, Tsunaharu Matsushima., Overproduction of Th2 CC chemokines TARC and MDC in the skin of the NC/Nga mouse correlates with exacerbation of atopic dermatitis like lesions. The 29th Annual Meeting of The Japanese Society for Immunology, Kyoto, Dec. 1, 1999, 2 pages. Abstract No. P-1-D-643-II.

Vestergaard et al., "Overproduction of Th2-specific chemokines in NC/Nga mice exhibiting atopic dermatitis-like lesions," J Clin Invest. 104(8):1097-105 (1999).

Vos et al., "Inhibition of inducible nitric oxide synthase improves graft function and reduces tubulointerstitial injury in renal allograft rejection," Eur. J. Pharmacol. 391(12):31-38 (2000).

Warrington et al., "CD4$_+$,CD28- T cells in rheumatoid arthritis patients combine features of the innate and adaptive immune systems," Arthritis Rheum. 44(1): 13-20 (2001).

Watanabe et al., "Concanavalin a induces perforin-mediated but not fas-mediated hepatic injury," Hepatology 24:702-710 (1996).

Weninger et al., "Migration and differentiation of CD8$^+$ T cells," Immunol Rev. 186: 221-233 (2002).

Wong et al., "Characterization of fractalkine (CX3CL1) and CX3CR1 in human coronary arteries with native atherosclerosis, diabetes mellitus, and transplant vascular disease," Cardiovascular Pathology. 11:332-338 (2002).

Xie et al., "Acquisition of selectin binding and peripheral homing properties by CD4$^+$ and CD8$^+$ T cells," J. Exp. Med. 189(11):1765-1775 (1999).

Yagira M., Toshio Imai, Shin Takagi, Masataka Baba, Ryu Yoshida, Osamu Yoshie., Identification of lymphocyte-specific CC type chemokine SLC, expressed mainly in lymph node., The 27th Annual Meeting of The Japanese Society for Immunology, Tokyo, Oct. 30, 1997, 2 pages. Abstract No. 2P236.

Yamaguchi et al., "A group of adhesion molecules controlling infiltration of immune cells," Molecular Medicine. 42(12):1375-1381 (2005). English language translation provided.

Yamaguchi K., Koji Morimoto, Shoko Hamaguchi, Miyuki Nishimura, Toshio Imai., New cell adhesion molecule associated with selective infiltration of Th1 cells., The 35th Annual Meeting of The Japanese Society for Immunology,Yokohama, Dec. 13-15, 2005, 28 pages. Abstract No. 2-C-W23-11-O/P.

Yanagawa T, Muramoto K, Nishimura M, Kumai M, lmai T. "The Fractalkine/CX3CR1 pathway is involved in the development of symptoms and allodynia in EAE through distinct mechanisms, and

(56) References Cited

OTHER PUBLICATIONS has both peripheral and central roles.." 10th International Congress of Neuroimmunology Barcelona, Spain Oct. 26-30, 2010, 3 pages. Abstract No. 172.

Yoneda et al., "Effects of fractalkine on NK cell activity and NK cell-mediated damage of endothelial cells," Shika Igaku (J Osaka Odontol Soc). 62(2):90-7 (1999). English translation provided.

Yoneda et al., "Fractalkine-mediated endothelial cell injury by NK cells," J Immunol. 164(8): 4055-62 (2000).

Yoneda et al., "Membrane-bound form of fractalkine induces IFN-gamma production by NK cells," Eur J Immunol. 33(1):53-8 (2003).

Yoneda O., Hiroshi Inoue, Miyuki Nishimura, Toshio Imai, Yasuhiro Minami, Naochika Domae, Hisanori Umehara. IFN-gamma production of NK cell by Fractalkine stimulation and analysis thereof. The 32nd Annual Meeting of The Japanese Society for Immunology, Tokyo, Dec. 5, 2002, 3 pages. Abstract No. 2-D-W23-14-O/P.

Yoneda O., Hiroshi Inoue, Miyuki Nishimura, Toshio Imai, Yasuhiro Minami, Naochika Domae, Hisanori Umehara. IFN-gamma productivity of NK cell by fractalkine and analysis thereof. The 31st Annual Meeting of The Japanese Society for Immunology, Kobe, Dec. 13, 2001, 3 pages. Abstract No. 3-H-W23-20-P.

Yoneda O., Hisanori Umehara, Hiroshi Inoue, Seiji Aida, Toshi Imai, Naochika Domae., Vascular endothelial cell injury by NK cell via CX3C-chemokine, fractalkine.,The 21st Annual Meeting of the Japanese Society of Inflammation, Tokyo, Jul. 4, 2000, 2 pages. Abstract No. 24.

Yoneda O., Hisanori Umehara, Hiroshi Inoue, Seiji Gouda, Toshio Imai, Osamu Yoshie, Naochika Doumae., Effect of CX3C-chemokine, Fractalkine on adhesion capacity to endothelial cell and cytotoxic activity of NK cell., The 26th Annual Meeting of the Japanese Society for Clinical Immunology, Oct. 1998, 4 pages. Abstract No. 3-B2-329.

Yoneda O., Hisanori Umehara, Hiroshi Inoue, Seiji Gouda, Toshio Imai, Osamu Yoshie, Naochika Doumae., Effect of CX3C-chemokine, Fractalkine on cytotoxic activity and releasing of intracellular granules of NK cell. The 63rd Annual Meeting of the Japanese Society for Interferon & Cytokine Research, Tokyo, Jul. 31, 1998, 2 pages. Abstract No. 36.

Yoneda O., Hisanori Umehara, Hitoshi Inoue, Seiji Aida, Toshio Imai, Osamu Yoshie, Hisao Imai, Naochika Domae., Effects of CX3C-Chemokine, fractalkine on endothelial cell adhesion capability and cytotoxicity of NK cell.The 29th Annual Meeting of The Japanese Society for Immunology, Kyoto, Dec. 3, 1999, 3 pages. Abstract No. P-3-C2-118-1.

Yoneda O., Seiji Aida, Hitoshi Inoue, Toshio Imai, Osamu Yoshie, Hisao Imai, Hisanori Umehara, Naochika Domae., Activation and IFN-gamma productivity of NK cell by fractalkine. The 30th Annual Meeting of The Japanese Society for Immunology, Symposium, Sendai, Nov. 16, 2000, 3 pages. Abstract No. 3-G-368-P/O.

Yoneyama et al., "Pivotal role of TARC, a CC chemokine, in bacteria-induced fulminant hepatic failure in mice," J Clin Invest. 102(11):1933-41 (1998).

Yoneyama H., Akihisa Harada, Toshio Imai, Osamu Yoshie, Zhang Yi, Hidemitu Azuma, Masako Murai, Hitoshi Asakura, Koji Matsushima., Role of chemokine, TARC in the acute hepatopathy onset mouse model., The 26th Annual Meeting of the Japanese Society for Clinical Immunology, Oct. 1998, 2 pages. Abstract 3-A4-112.

Yoshida et al., "An activation-responsive element in single C motif-1/Lymphotactin promoter is a site of constitutive and inducible DNA-protein interactions involving nuclear factor of activated T cell," J Immunol. 163(6):3295-303 (1999).

Yoshida et al., "EbI1-ligand chemokine (ELC) attracts a broad spectrum of lymphocytes: activated T cells strongly up-regulate CCR7 and efficiently migrate toward ELC," Int Immunol. 10(7):901-10 (1998).

Yoshida et al., "Identification of Single C Motif-1/Lymphotactin receptor XCR1," J Biol Chem. 273(26):16551-4 (1998).

Yoshida et al., "Molecular cloning of a novel C or gamma type chemokine, SCM-1," FEBS Lett. 360(2):155-9 (1995).

Yoshida et al., "Molecular cloning of a novel human CC chemokine EBI1-ligand chemokine that is a specific functional ligand for EBI1, CCR7," J Biol Chem. 272(21):13803-9 (1997).

Yoshida et al., "Molecular cloning of mXCR1, the murine SCM-1/lymphotactin receptor," FEBS Lett. 458(1):37-40 (1999).

Yoshida et al., "Secondary lymphoid-tissue chemokine (SLC) is a functional ligand for the CC chemokine receptor CCR7," J Biol Chem. 273(12):7118-22 (1998).

Yoshida et al., "Structure and expression of two highly related genes encoding SCM-1/human lymphotactin," FEBS Lett. 395(1):82-8 (1996).

Yoshida R., Toshio Imai, Masataka Baba, Morio Yagira, Osamu Yoshie., Cloning of novel human CC chemokine ELC and identification of its receptor CCR7/EBI1.,The 27th Annual Meeting of The Japanese Society for Immunology, Tokyo, Oct. 30, 1997, 2 pages. Abstract No. 2J15.

Yoshie et al., "Chemokines in immunity," Adv Immunol. 78:57-110 (2001).

Yoshie et al., "Novel lymphocyte-specific CC chemokines and their receptors," J Leukoc Biol. 62(5):634-44 (1997).

Yoshie O., S. Takagi, M. Baba, M. Kitaura, M. Nishimura, M. Kakizaki, T. Imai. Identification of specific receptor for TARC, a T cell-directed CC chemokine. Keystone Symposia, The role of chemokines in leukocyte trafficking and disease, Colorado, Apr. 2, 1997, 2 pages. Abstract No. 227.

Yoshie O., T. Imai. The VIth International Symposium on the Molecular Cell Biology of Macrophages '97, Tokyo, May 23, 1997, 1 page.

Yoshie O., Yoshikazu Tanaka, Toshio Imai, Koichi Araki, and Yorio Hinuma., Induction of Cell Adhesion Molecules by HTLV-1., The 52nd Annual Meeting of the Japanese Cancer Association, Sendai, Oct. 5, 1993, 2 pages. Abstract No. W9-9.

Yoshikawa et al., "TNF-alpha and IL-4 regulate expression of fractalkine (CX3CL1) as a membrane-anchored proadhesive protein and soluble chemotactic peptide on human fibroblasts," FEBS Lett. 561(1-3):105-10 (2004).

Yoshikawa M., Makoto Iida, Toshiharu Nakajima, Kenji Matsumoto, Nao Aida, Toshio Imai, Hiroshi Moriyama, Hirohisa Saito. Expression analysis of Fractalkine (CX3CL1) in human fibroblast. The 51st Annual Meeting of Japanese Society of Allergology, Oct. 30, 2002, 2 pages. Abstract No. 352.

Zhang et al., "Regulation of experimental autoimmune encephalomyelitis by natural killer (NK) cells," J. Exp. Med. 186(10):1677-1687 (1997).

Zheng et al., "NK cells do not mediate renal injury in murine adriamycin nephropathy," Kidney International. 69:1159-65 (2006).

Zujovic et al., "In vivo neutralization of endogenous brain fractalkine increases hippocampal TNFα and 8-isoprostane production induced by intracerebroventricular injection of LPS," J. Neuroimmunol. 115:135-143 (2001).

Amendment (Appeal Brief) and its English translation for Japanese Application No. 2001-308619, filed Jun. 5, 2008 (15 pages).

Amendment (Appeal Brief) and its English translation for Japanese Application No. 2008-121030, filed Apr. 23, 2010 (20 pages).

Amendment and its English translation for Japanese Application No. 2001-308619, filed Mar. 4, 2003 (2 pages).

Amendment and its English translation for Japanese Application No. 2001-308619, filed Feb. 13, 2007 (2 pages).

Amendment and its English translation for Japanese Application No. 2001-308619, filed May 7, 2008 (2 pages).

Amendment and its English translation for Japanese Application No. 2001-308619, filed Dec. 17, 2008 (2 pages).

Amendment and its English translation for Japanese Application No. 2006-542371, filed Jul. 11, 2011 (2 pages).

Amendment and its English translation for Japanese Application No. 2006-542371, filed Oct. 26, 2011 (7 pages).

Amendment and its English Translation for Japanese Application No. 2008-121030, filed Dec. 17, 2008 (2 pages).

Amendment and its English Translation for Japanese Application No. 2008-121030, filed Mar. 23, 2010 (2 pages).

Amendment and its English Translation for Japanese Application No. 2008-121030, filed Dec. 25, 2012 (2 pages).

(56) References Cited

OTHER PUBLICATIONS

Amendment with its English Translation for Japanese Application No. 2000-354387, dated Feb. 24, 2010 (3 pages).
Appeal Brief with its English translation for Japanese Application No. 2000-354387, dated Apr. 15, 2010 (17 pages).
Argument and its English translation for Japanese Application No. 2001-308619, filed Feb. 2, 2007 (8 pages).
Argument and its English translation for Japanese Application No. 2001-308619, filed Dec. 17, 2008 (2 pages).
Argument and its English translation for Japanese Application No. 2008-121030, filed Dec. 17, 2008 (17 pages).
Decision of Refusal and its English translation for Japanese Application No. 2000-354387, mailed Nov. 24, 2009 (5 pages).
Decision of Refusal and its English translation for Japanese Application No. 2001-308619, mailed Mar. 4, 2008 (4 pages).
Decision of Refusal and its English translation for Japanese Application No. 2008-121030, drafted Dec. 16, 2009 and mailed Dec. 22, 2009 (4 pages).
Declaration under 37 C.F.R. 1.132 for U.S. Appl. No. 09/963,316, mailed Apr. 4, 2005 (3 pages).
Extended European Search Report for European Application No. 05805446.1, dated Nov. 10, 2008 (9 pages).
Final Office Action for U.S. Appl. No. 09/963,316, mailed Oct. 4, 2004 (5 pages).
Final Office Action for U.S. Appl. No. 09/963,316, mailed Jun. 13, 2005 (5 Pages).
Final Office Action for U.S. Appl. No. 11/393,283, mailed Jul. 3, 2008 (7 pages).
Final Office Action for U.S. Appl. No. 11/718,246, dated Sep. 3, 2009 (20 pages).
Final Office Action for U.S. Appl. No. 11/718,246, dated Aug. 8, 2011 (8 pages).
International Preliminary Report on Patentability and its English translation for International Application No. PCT/JP2004/014277, dated Jan. 19, 2006 (13 pages).
International Preliminary Report on Patentability and its English translation for International Application No. PCT/JP2005/020009, issued May 1, 2007 (16 pages).
International Search Report and its English translation for International Application No. PCT/JP2004/014277, mailed Dec. 7, 2004 (6 pages).
International Search Report and its English translation for International Application No. PCT/JP2005/020009, mailed Jan. 17, 2006 (9 pages).
Notice of Questioning and its English translation for Japanese Application No. 2000-354387, mailed Feb. 14, 2012 (11 pages).
Notice of Questioning and its English translation for Japanese Application No. 2008-121030, mailed May 29, 2012 (7 pages).
Notice of Reason for Rejection and its English Translation for Japanese Application No. 2000-354387, mailed Jul. 24, 2012 (15 pages).
Notice of Reason for Rejection and its English translation for Japanese Application No. 2001-308619, mailed Dec. 12, 2006 (4 pages).
Notice of Reason for Rejection and its English translation for Japanese Application No. 2001-308619, mailed Nov. 4, 2008 (6 pages).
Notice of Reason for Rejection and its English translation for Japanese Application No. 2006-542371, mailed May 10, 2011 (10 pages).
Notice of Reason for Rejection and its English translation for Japanese Application No. 2006-542371, mailed Sep. 13, 2011 (4 pages).
Notice of Reason for Rejection and its English translation for Japanese Application No. 2008-121030, mailed Nov. 11, 2008 (8 pages).
Notice of Reason for Rejection and its English translation for Japanese Application No. 2011-235023, mailed Jul. 2, 2013 (8 pages).
Notice of Reason for Rejection and its English translation for Japanese Patent Application No. 2000-354387, mailed Aug. 4, 2009 (4 pages).
Notice of Reasons for Rejection and its English translation for Japanese Application No. 2008-121030, mailed Oct. 23, 2012 (8 pages).
Office Action and its English translation for Thailand Application No. 1201001966, issued Oct. 31, 2013 (4 pages).
Office Action for European Application No. 05805446.1, dated Jan. 22, 2009 (2 pages).
Office Action for European Application No. 05805446.1, dated Aug. 11, 2010 (8 pages).
Office Action for European Application No. 05805446.1, dated Jun. 25, 2012 (7 pages).
Office Action for U.S. Appl. No. 09/963,316, mailed Feb. 23, 2004 (5 pages).
Office Action for U.S. Appl. No. 11/225,829, mailed Oct. 25, 2006 (5 pages).
Office Action for U.S. Appl. No. 11/225,829, mailed Jan. 26, 2006 (4 pages).
Office Action for U.S. Appl. No. 11/225,829, mailed Apr. 17, 2007 (5 pages).
Office Action for U.S. Appl. No. 11/393,283, mailed Dec. 21, 2007 (9 pages).
Office Action for U.S. Appl. No. 11/718,246, dated Nov. 4, 2008 (14 pages).
Office Action for U.S. Appl.No. 11/718,246, dated Feb. 24, 2011 (17 pages).
Response to Final Office Action for U.S. Appl. No. 09/963,316, mailed Apr. 1, 2005 and received by USPTO on Apr. 4, 2005 (7 pages).
Response to Final Office Action for U.S. Appl. No. 09/963,316, mailed Sep. 13, 2005 and received by the USPTO on Sep. 15, 2005 (6 pages).
Response to First Office Action and its English translation for Chilean Application No. 1143-2012, filed Dec. 11, 2013 (19 pages).
Response to First Office Action and its English translation for Chinese Application No. 201080049138.0, filed Nov. 18, 2013 (14 pages).
Response to Notice of Reason for Rejection and its English translation for Japanese Application No. 2000-354387, dated Oct. 2, 2009 (8 pages).
Response to Notice of Reason for Rejection and its English translation for Japanese Application No. 2006-542371, filed Jul. 11, 2011 (11 pages).
Response to Notice of Reason for Rejection and its English translation for Japanese Application No. 2006-542371, filed Oct. 26, 2011 (3 pages).
Response to Notice of Reason for Rejection and its English translation for Japanese Application No. 2008-121030, filed Dec. 24, 2012 (11 pages).
Response to Office Action for European Application No. 05805446.1, dated Jul. 14, 2009 (8 pages).
Response to Office Action for European Application No. 05805446.1, dated Jan. 19, 2011 (5 pages).
Response to Office Action for European Application No. 05805446.1, dated Sep. 18, 2012 (5 pages).
Response to Office Action for U.S. Appl. No. 09/963,316, mailed Jun. 23, 2004 and received by the USPTO on Jun. 25, 2004 (8 pages).
Response to Office Action for U.S. Appl. No. 11/225,829, mailed Apr. 7, 2006 and received by the USPTO on Apr. 11, 2006 (6 pages).
Response to Office Action for U.S. Appl. No. 11/225,829, mailed Dec. 12, 2006 and received by the USPTO on Dec. 14, 2006 (6 pages).
Response to Office Action for U.S. Appl. No. 11/225,829, mailed May 7, 2007 and received by the USPTO on May 10, 2007 (5 pages).
Response to Office Action for U.S. Appl. No. 11/393,283, filed Apr. 15, 2008 (10 pages).
Response to Office Action for U.S. Appl. No. 11/718,246, filed May 4, 2009 (11 pages).
Response to Office Action for U.S. Appl. No. 11/718,246, filed Jul. 6, 2009 (11 pages).
Response to Office Action for U.S. Appl. No. 11/718,246, filed Apr. 5, 2010 (10 pages).
Response to Office Action for U.S. Appl. No. 11/718,246, filed Jun. 23, 2011 (12 pages).
Response to Office Action for U.S. Appl. No. 11/718,246, filed Nov. 14, 2011 (7 pages).
Response to Restriction Requirement for U.S. Appl. No. 09/963,316, mailed Nov. 26, 2003 and received by the USPTO on Dec. 1, 2013 (6 pages).

(56) References Cited

OTHER PUBLICATIONS

Response to Restriction Requirement for U.S. Appl. No. 11/393,283, filed Nov. 19, 2007 (4 pages).
Response to Restriction Requirement for U.S. Appl. No. 11/718,246, dated May 14, 2008 (5 pages).
Response to Restriction Requirement for U.S. Appl. No. 11/718,246, filed Aug. 29, 2008 (2 pages).
Restriction Requirement for U.S. Appl. No. 09/963,316, mailed Sep. 26, 2003 (5 pages).
Restriction Requirement for U.S. Appl. No. 11/393,283, mailed Oct. 18, 2007 (7 pages).
Restriction Requirement for U.S. Appl. No. 11/718,246, dated Apr. 14, 2008 (5 pages).
Restriction Requirement for U.S. Appl. No. 11/718,246, dated Jul. 29, 2008 (9 pages).
Statement and its English translation for Japanese Application No. 2008-121030, filed Jun. 3, 2008 (3 pages).
Statement and its English Translation for Japanese Application No. 2011-235023, filed Oct. 26, 2011 (4 pages).
Supplementary European Search Report for European Application No. 04788343, mailed Jun. 8, 2009 (4 pages).
Written Reply and its English translation for Japanese Application No. 2000-354387, filed Apr. 16, 2012 (18 pages).
Written Reply and its English translation for Japanese Application No. 2008-121030, dated Jul. 30, 2012 (16 pages).
Response to Office Action for Thai Patent Application No. 1201001966, submitted Feb. 27, 2014 (10 pages).
Response to Second Office Action for New Zealand Patent Application No. 599779, submitted Mar. 4, 2014 (16 pages).
Response to Extended European Search Report for European Patent Application No. 10826929.1, submitted Apr. 29, 2014 (8 pages).
Second Office Action for Chinese Patent Application No. 201080049138.0, issued Mar. 14, 2014 (15 pages).
Brand et al., "Fractalkine-mediated signals regulate cell-survival and immune-modulatory responses in intestinal epithelial cells," Gastroenterology. 122(1):166-77 (2002).
Cook et al., "Generation and analysis of mice lacking the chemokine fractalkine," Mol Cell Biol. 21(9):3159-65 (2001).
Holdsworth et al., "Chemokines as therapeutic targets in renal disease," Curr Opin Nephrol Hypertens. 9(5):505-1 1 (2000).
Infante-Duarte et al., "Frequency of blood CX3CR1-positive natural killer cells correlates with disease activity in multiple sclerosis patients," FASEB J. 19(13):1902-4 (2005).
Jung et al., "Analysis of fractalkine receptor CX3CR1 function by targeted deletion and green fluorescent protein reporter gene insertion," Mol Cell Biol. 20(11):4106-14 (2000).
Limatola et al., "Chemokine CX3CL1 protects rat hippocampal neurons against glutamate-mediated excitotoxicity," J Neuroimmunol. 166(1-2):19-28 (2005).

Meucci et al., "Expression of CX3CR1 chemokine receptors on neurons and their role in neuronal survival," Proc Natl Aced Sci USA. 97(14):8075-80 (2000).
Ollivier et al., "Fractalkine/CX3CL1 production by human aortic smooth muscle cells impairs monocyte procoagulant and inflammatory responses," Cytokine. 21(6):303-1 1 (2003).
Tong et al., "Neuronal fractalkine expression in HIV-1 encephalitis: roles for macrophage recruitment and neuroprotection in the central nervous system," J Immunol. 164(3):1333-9 (2000).
Zujovic et al., "Fractalkine modulates TNF-alpha secretion and neurotoxicity induced by microglial activation," Glia. 29(4):305-15 (2000).
Response to Second Office Action for Chinese Application No. 201080049138.0, dated May 27, 2014 (16 pages).
Fourth Office Action for European Application No. 05805446.1, dated Jun. 17, 2014 (6 pages).
First Office Action for Israeli Application No. 219470, dated Jun. 19, 2014 (4 pages).
First Office Action for Mexican Application No. MX/a/2012/005052, dated Mar. 31, 2014 (7 pages).
Response to First Office Action for Mexican Application No. MX/a/2012/005052, dated Jul. 15, 2014 (16 pages).
Morita et al., "A perforin/granzyme-positive MDS-derived T cell line, K2-MDS, induces apoptosis in $CD34^+$ cells through the fractalkine-CX3CR1 system," Clin Immunol. 113(1):109- 16 (2004).
Response to Office Action for European Application No. 05805446.1, dated Sep. 22, 2014 (17 pages).
Third Office Action for Chinese Patent Application No. 201080049138.0, issued Aug. 29, 2014. English language translation provided (14 pages).
Jarrin et al., "Sequencing of antibodies," Methods Mol Biol. 96:21-8 (1999).
Kim et al., "Antibody engineering for the development of therapeutic antibodies," Mol Cells. 20(1):17-29 (2005).
First Office Action and English translation for Russian Application No. 2012122203, issued on Aug. 21, 2014 (8 pages).
Response to First Office Action and English translation for Japanese Application No. 2012-520621, submitted on Sep. 18, 2014 (11 pages).
First Office Action for Singaporean Application No. 2012031563, issued Sep. 18, 2014 (2 pages).
Search Report for Singaporean Application No. 201203156-3, mailed Sep. 8, 2014 (7 pages).
Written Opinion for Singaporean Application No. 201203156-3, mailed Sep. 8, 2014 (13 pages).
Notice of Reasons for Rejection for JP 2014-189668, mailed Oct. 28, 2014 (8 pages).
Patent Examination Report No. 1 for AU 2010312408, dated Oct. 31, 2014 (3 pages).

* cited by examiner

Figure 1

MAPISLSWLLRLATFCHLTVLLAGQHHGVTKCNITCSKMTSKIPVALLIHYQQN
QASCGKRAIILETRQHRLFCADPKEQWVKDAMQHLDRQAAALTRNGGTFEKQI
GEVKPRTTPAAGGMDESVVLEPEATGESSSLEPTPSSQEAQRALGTSPELPTGVTG
SSGTRLPPTPKAQDGGPVGTELFRVPPVSTAATWQSSAPHQPGPSLWAEAKTSE
APSTQDPSTQASTASSPAPEENAPSEGQRVWGQGQSPRPENSLEREEMGPVPA
HTDAFQDWGPGSMAHVSVVPVSSEGTPSREPVASGSWTPKAEEPIHATMDPQR
LGVLITPVPDAQAATRRQAVGLLAFLGLLFCLGVAMFTYQSLQGCPRKMAGEMAE
GLRYIPRSCGSNSYVLVPV (SEQ ID NO: 1)

Figure 2

| | | 1F3-1 | 3A5-2 | 3H7-6 |
|---|---|---|---|---|
| Chemotaxis assay $IC_{50}$ (nM) | Mouse | - | - | - |
| | Human | 12.67 (±5.07) | 4.80 (±1.33) | 19.07 (±5.13) |
| Affinity (BIACORE) KD (nM) | Mouse | - | - | - |
| | Human | 0.66 | 0.60 | 0.83 |
| Reactivity to cynomolgus monkey FKN (ELISA) | | Not equal to human | equal to human | equal to human |

- : no activity

Figure 4

● Narrowed Key residues

Figure 5

| | | 1st | 2nd | 3rd | Av. | SD |
|---|---|---|---|---|---|---|
| mouse | IC50 | 0.52 | 0.61 | 0.54 | 0.55 | 0.05 |
| | IC90 | 4.08 | 4.24 | 3.23 | 3.85 | 0.55 |
| | IC95 | 8.61 | 10.84 | 6.66 | 8.70 | 2.09 |
| chimeric | IC50 | 0.34 | 0.29 | 0.43 | 0.35 | 0.07 |
| | IC90 | 3.36 | 2.21 | 1.66 | 2.41 | 0.87 |
| | IC95 | 7.07 | 5.24 | 3.15 | 5.15 | 1.96 |
| H3L2 | IC50 | 0.47 | 0.26 | 0.29 | 0.34 | 0.12 |
| | IC90 | 2.94 | 2.25 | 1.34 | 2.18 | 0.80 |
| | IC95 | 5.61 | 4.69 | 2.91 | 4.40 | 1.37 |
| H3L4 | IC50 | 0.44 | 0.91 | 0.44 | 0.60 | 0.27 |
| | IC90 | 8.34 | 5.11 | 4.43 | 5.96 | 2.09 |
| | IC95 | 15.92 | 50.26 | 10.46 | 25.54 | 21.58 |
| H3-2L2 | IC50 | 0.25 | 0.23 | 0.27 | 0.25 | 0.02 |
| | IC90 | 2.23 | 2.13 | 2.67 | 2.34 | 0.29 |
| | IC95 | 4.25 | 5.28 | 5.59 | 5.04 | 0.70 |
| H3-2L4 | IC50 | 0.20 | 0.65 | 0.45 | 0.43 | 0.23 |
| | IC90 | 2.71 | 3.01 | 2.98 | 2.90 | 0.17 |
| | IC95 | 6.36 | 7.00 | 5.92 | 6.43 | 0.54 |
| H3-2L5 | IC50 | 0.13 | 0.46 | 0.57 | 0.39 | 0.23 |
| | IC90 | 1.97 | 4.92 | 3.84 | 3.58 | 1.49 |
| | IC95 | 5.81 | 17.47 | 6.68 | 9.99 | 6.50 |
| HK2L2 | IC50 | 16.49 | 27.86 | ND | | |
| | IC90 | >66.67 | >66.67 | ND | | |
| | IC95 | >66.67 | >66.67 | ND | | |
| HK2L4 | IC50 | 16.87 | 19.59 | ND | | |
| | IC90 | >66.67 | >66.67 | ND | | |
| | IC95 | >66.67 | >66.67 | ND | | |
| HK3L2 | IC50 | 1.65 | 8.50 | 9.63 | 6.59 | 4.32 |
| | IC90 | >66.67 | >66.67 | >66.67 | | |
| | IC95 | >66.67 | >66.67 | >66.67 | | |
| HK3L4 | IC50 | 0.42 | 25.25 | >66.67 | 12.84 | 17.56 |
| | IC90 | >66.67 | >66.67 | >66.67 | | |
| | IC95 | >66.67 | >66.67 | >66.67 | | |
| HK3L5 | IC50 | 1.10 | 14.17 | 13.50 | 9.59 | 7.36 |
| | IC90 | >66.67 | >66.67 | >66.67 | | |
| | IC95 | >66.67 | >66.67 | >66.67 | | |

Figure 6
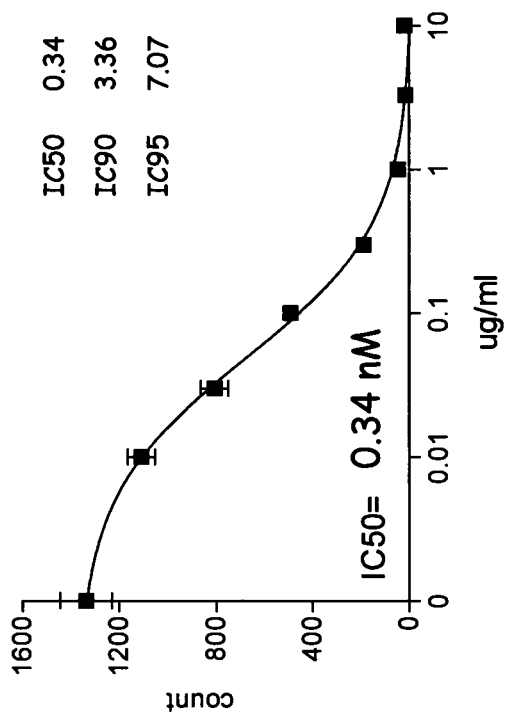
B *Chimeric*
IC50 0.34
IC90 3.36
IC95 7.07
IC50= 0.34 nM
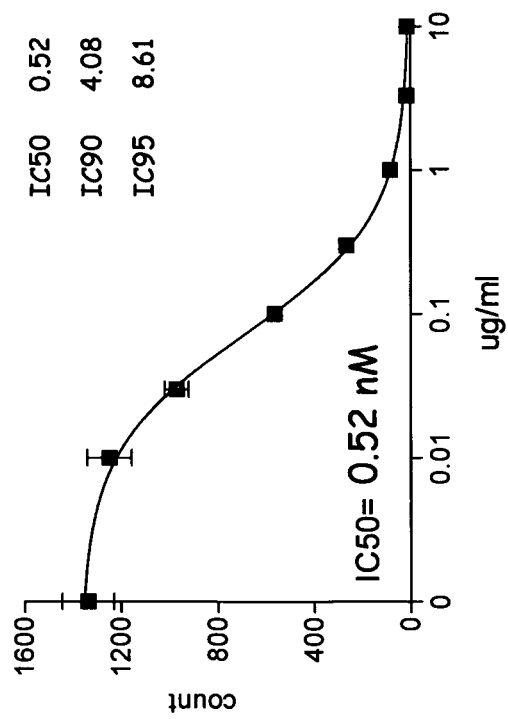
A *m3A5-2 (hybridoma)*
IC50 0.52
IC90 4.08
IC95 8.61
IC50= 0.52 nM

Figure 9

| mAbs | human FKN-SEAP | | | cynomolgus FKN-SEAP | | |
|---|---|---|---|---|---|---|
| | ka (1/Ms) | kd (1/s) | KD (M) | ka (1/Ms) | kd (1/s) | KD (M) |
| chimeric | 1.34E+07 | 9.58E-05 | 7.13E-12 | 1.43E+07 | 9.54E-05 | 6.62E-12 |
| H3L2 | 1.32E+07 | 1.16E-04 | 8.84E-12 | 1.26E+07 | 1.22E-04 | 9.62E-12 |
| H3-2L2 | 1.50E+07 | 8.83E-05 | 5.92E-12 | 1.39E+07 | 9.43E-05 | 6.75E-12 |
| H3L4 | 1.56E+07 | 1.05E-04 | 6.43E-12 | 1.61E+07 | 1.87E-04 | 1.20E-11 |
| H3-2L4 | 1.88E+07 | 1.01E-04 | 5.34E-12 | 1.49E+07 | 1.15E-04 | 7.71E-12 |
| HK2L4 | 1.83E+07 | 6.14E-04 | 3.40E-11 | 2.49E+07 | 6.35E-04 | 2.60E-11 |

Epitope Mapping BIACORE

Gray: Cross saturation
Black: Chemical shift mapping

COMPOSITIONS AND METHODS FOR TREATING INFLAMMATORY DISORDERS

CROSS-REFERENCE TO RELATED APPLICATIONS

This application is the U.S. national stage filing under 35 U.S.C. §371 of international application PCT/JP2010/069653, filed Oct. 28, 2010, which claims benefit of U.S. Provisional Application No. 61/256,521, filed Oct. 30, 2009.

FIELD OF THE INVENTION

The present invention features compositions and methods related to antibodies that bind fractalkine.

BACKGROUND OF THE INVENTION

Fractalkine (FKN) is a transmembrane chemokine that is expressed on the surface of activated endothelial cells and binds to the CX3CR1 receptor. The binding of membrane-bound FKN to membrane-bound CX3CR1 mediates strong cell-cell adhesion without the involvement of selectins or integrins. Secreted FKN, which is shed from membrane-bound FKN, also binds to CX3CR1 and induces the activation of integrin and cell chemotaxis.

Expression of FKN is induced on the surface of endothelial cells by proinflammatory cytokines. The elevated expression of FKN and the accumulation of CX3CR1$^+$ cytotoxic effector lymphocytes and macrophages have been reported in subjects with numerous disorders, including inflammatory and autoimmune disorders, including ulcerative colitis (UC), Crohn's disease (CD), rheumatoid arthritis (RA), autoimmune hepatitis (AIH), multiple sclerosis (MS), and diabetes mellitus. Umehara et al., *Arterioscler. Thromb. Vasc. Biol.* 24:34-40 (2004) describes the role of FKN in atherosclerosis and vascular injury. Nishimura et al., *Ann. NY Acad. Sci.* 1173:350-356 (2009) discusses FKN as a potential therapeutic target for inflammatory bowel disease such as UC and CD.

Antibodies and FKN-binding fragments of antibodies are desirable therapeutic agents because of their specificity. Antibodies and FKN-binding fragments may be used to target specific cells or tissues, thereby minimizing the potential side effects of non-specific targeting. There is a need to identify and characterize therapeutic antibodies useful in the treatment of inflammatory disorders, including those that are described herein.

SUMMARY OF THE INVENTION

In a first aspect, the invention features an anti-FKN antibody or FKN-binding fragment thereof, wherein the antibody or fragment thereof includes six CDRs selected from:
(a) a CDR-H1 that includes the amino acid sequence of SEQ ID NO: 28;
(b) a CDR-H2 that includes the amino acid sequence of SEQ ID NO: 29;
(c) a CDR-H3 that includes the amino acid sequence of SEQ ID NO: 30;
(d) a CDR-L1 that includes the amino acid sequence of SEQ ID NO: 31;
(e) a CDR-L2 that includes the amino acid sequence of SEQ ID NO: 32; and
(f) a CDR-L3 that includes the amino acid sequence of SEQ ID NO: 33.

The antibody may be an intact antibody. In one example, the antibody is a humanized antibody. The heavy chain variable domain of the humanized antibody may include the amino acid sequence of SEQ ID NO: 36, SEQ ID NO: 37, SEQ ID NO: 39, SEQ ID NO: 42, or SEQ ID NO: 43, and the light chain variable domain of the humanized antibody may include the amino acid sequence of SEQ ID NO: 38, SEQ ID NO: 44, or SEQ ID NO: 45.

In one example, the antibody is an anti-fractalkine antibody or FKN-binding fragment thereof, wherein the antibody or fragment thereof includes a heavy chain with the amino acid sequence of SEQ ID NO: 37 and a light chain with the amino acid sequence of SEQ ID NO: 44.

The antibody may also be a chimeric antibody. In one example, the heavy chain variable domain of the chimeric antibody includes the amino acid sequence of SEQ ID NO: 26, and the light chain variable domain of the chimeric antibody includes the amino acid sequence of SEQ ID NO: 27.

FKN-binding fragments of an antibody are also contemplated. The FKN-binding fragment may be a Fab, Fab', F(ab')2, or Fv fragment that retains the binding specificity to FKN.

In certain examples, when the antibody or FKN-binding fragment thereof includes a human constant region, the constant region is of the IgG isotype (e.g., the IgG2 isotype).

In other examples, the antibody or FKN-binding fragment includes a mutated Fc region such that the antibody has reduced ADCC and/or complement activation relative to the Fc region lacking the mutation. For example, the Fc region may be mutated at one or more of amino acid residues V234, G237, C131, or C219.

Desirably, the antibody or FKN-binding fragment substantially reduces or inhibits binding of FKN to its receptor, CX3CR1, by at least 50%, 60%, 70%, 80%, 90%, or greater, or substantially inhibits neutralized hFKN in a chemotaxis assay such as the one described herein.

The invention also features a pharmaceutical composition that includes the antibody or FKN-binding fragment of the present invention and a pharmaceutically acceptable carrier or excipient. In certain embodiments, the composition includes one or more additional therapeutic agents, such as those described below.

Also contemplated is a nucleic acid encoding and antibody or FKN-binding fragment described above. In one embodiment, the nucleic acid encodes all or a portion of the heavy chain of the antibody or FKN-binding fragment thereof. In another embodiment, the nucleic acid encodes all or a portion of the light chain of the antibody or FKN-binding fragment thereof. The nucleic acid may be in a vector (e.g., an expression vector).

The invention also features a host cell that includes one or more vectors of the invention. In one example, the host cell includes two vectors, the first vector including a nucleic acid encoding a heavy chain and the second vector including a nucleic acid encoding a light chain of an antibody or FKN-binding fragment described herein. The expression of the heavy and light chain in the host cell produces an antibody or FKN-binding fragment. In one embodiment, the host cell is prokaryotic. In another embodiment, the host cell is eukaryotic. Exemplary mammalian cells useful for producing antibodies and FKN-binding fragments are CHO cells and NS0 cells.

The invention also features a method for making an anti-FKN antibody or FKN-binding fragment thereof. The method includes (a) expressing a vector of the invention in a suitable host cell, and (b) recovering the antibody. The antibody or FKN-binding fragment may be secreted by the host cell into culture media. In one example, the antibody or FKN-binding fragment thereof is purified to remove at least 95% or greater purity of the non-antibody materials.

Methods for treating an inflammatory disorder by administering an effective amount of an anti-FKN antibody or FKN-binding fragment in accordance with the invention are also contemplated. Exemplary inflammatory disorders are inflammatory bowel disease, Crohn's disease, and ulcerative colitis. For these disorders, the method may further include administering one or more additional therapeutic agents. Exemplary therapeutic agents are opiates, 5-aminosalicylic acid, 6-mercaptopurine, azathioprine, glucocorticoids, methotrexate, cyclosporine, and metronidazole. Other suitable therapeutic agents are described below.

Inflammatory disorders that may be treated by administering an effective amount of an anti-FKN antibody or FKN-binding fragment in accordance with the invention also include autoimmune hepatobiliary diseases (e.g., autoimmune hepatitis, primary biliary cirrhosis, or primary sclerosing cholangitis). For these disorders, the method may further include administering 6-mercaptopurine, ursodeoxycholic acid, azathioprine, a glucocorticoid, a thiazide diuretic, an anti-aldosterone diuretic, cyclosporine, albumin, or spironolactone.

Rheumatoid arthritis (RA) may also be treated by administering an effective amount of an anti-FKN antibody or FKN-binding fragment in accordance with the invention. In the treatment of RA, the method may further include administering a non-steroidal anti-inflammatory drug (NSAID), methotrexate, leflunomide, bucillamine, 5-aminosalicylic acid, a glucocorticoid, hydrochloroquine, vitamin D, calcium, or alendronate.

Systemic lupus erythematosus (e.g., lupus of the central nervous system or lupus nephritis) may also be treated by administering an effective amount of an anti-FKN antibody or FKN-binding fragment, either alone or in combination with one or more additional therapeutic agents. Exemplary additional therapeutic agents are glucocorticoids, cyclophosphamide, methotrexate, cyclosporine, and tacrolimus.

Multiple sclerosis and neuromyelitis optica may also be treated by administering an effective amount of an anti-FKN antibody or FKN-binding fragment. Treatment may further include administering one or more additional therapeutic agents, such as a glucocorticoid, interferon-β, or Copaxone®.

Demyelinating polyradiculopathy (e.g., Guillain-Barré syndrome or chronic inflammatory demyelinating polyradiculopathy) may also be treated by administering an effective amount of an anti-FKN antibody or FKN-binding fragment. Again, cotherapy is also contemplated, and treatment may further include administering one or more additional therapeutic agents, such as a glucocorticoid or an intravenous immunoglobulin.

Administering an effective amount of an anti-FKN antibody or FKN-binding fragment may also be useful for the treatment of neuropathic pain, either alone or in combination with an additional therapeutic agent. Exemplary additional agents for the treatment of neuropathic pain are lamotrigine, topiramate, oxcarbazepine, levetiracetam, fentanyl, tramadol, capsaicin, cloridine, an NSAID, amitriptyline, pregabalin, lidocaine, duloxetine, and carbamazepine.

Alzheimer's disease may also be treated by administering an effective amount of an anti-FKN antibody or FKN-binding fragment. The method may further include administering one or more additional therapeutic agents, such as tacrine hydrochloride, donepezil hydrochloride, rivastigmine tartrate, galantamine hydrobromide, memantine hydrochloride, paroxetine, risperidone, quetiapine, or perospirone.

Visceral pain associated with cancer may also be treated by administering an effective amount of an anti-FKN antibody or FKN-binding fragment, either alone or in combination with one or more additional therapeutic agents, such as morphine, an NSAID, phentanyl, lidocaine, pentazocine, or clonidine.

Atherosclerosis may also be treated by administering an effective amount of an anti-FKN antibody or FKN-binding fragment. The method may further include administering one or more additional therapeutic agents, such as prostacyclin, aspirin, clopidogrel, ticlopidine, limaprost, prostaglandin E1, an HMG CoA reductase inhibitor, bezafibrate, lidocaine, mexiletine, a diuretic, digitalis, dopamine, a β-adrenergic receptor agonist, isosorbide dinitrate, nitroglycerin, a natriuretic peptide, warfarin, heparin, tissue plasminogen activator, urokinase, or procainamide.

Vasculopathies (e.g., age-related macular degeneration, Behcet's disease, Harada's disease, and sarcoidosis-origined uveitis) may also be treated by administering an effective amount of an anti-FKN antibody or FKN-binding fragment in accordance with the invention. The method may further include administering one or more additional therapeutic agents selected from glucocorticoids, cyclophosphamide, pegaptanib, ranibizumab, NSAIDs, colchicine, chlorambucil, thalidomide, and verteporfin.

Nephropathies (e.g., lupus nephritis, glomerulonephritis, or diabetic nephropathy) may also be treated by administering an effective amount of an anti-FKN antibody or FKN-binding fragment in accordance with the invention. Glucocorticoids, sulfonylurea, cyclophosphamide, glinides, cyclosporine, tacrolimus, mycophenolate mofetil, mizoribine, diuretics, insulin, biguanide, α-glucosidase inhibitors, angiotensin receptor blockers, thiazolidinedione, angiotensin converting enzyme (ACE) inhibitors, calcium channel blockers, or β-adrenergic receptor inhibitors may be included in the treatment methods. adrenergic receptor inhibitors may be included in the treatment methods.

The invention also relates to the use of an anti-FKN antibody or FKN-binding fragment in accordance with the invention in the treatment of any of the inflammatory disorders described herein.

The invention also relates to the use of an anti-FKN antibody or FKN-binding fragment in accordance with the invention in the preparation of a medicament for the treatment of any of the inflammatory disorders described herein.

The invention also features a method of inhibiting the recruitment of leukocytes to an inflammation site in a subject by administering an effective amount of an anti-FKN antibody or FKN-binding fragment to a subject in need of such treatment, whereby the recruitment of leukocytes to an inflammation site is inhibited.

An ex vivo strategy can also be used for therapeutic applications. Ex vivo strategies involve transfecting or transducing cells obtained from the subject with a polynucleotide encoding an antibody or antibody fragment. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells.

For the purpose of the present invention, the following abbreviations and terms are defined below.

The term "antibody" (used herein interchangeably with "immunoglobulin") includes intact monoclonal and polyclonal antibodies, multispecific antibodies (e.g., bispecific antibodies), and antibody fragments that exhibit the desired biological activity (e.g., the ability to bind FKN and modulate the interaction between FKN and CX3CR1). "Intact antibodies" are heterotetrameric glycoproteins of about 150,000 Daltons, composed of two identical light (L) chains and two identical heavy (H) chains. Each light chain is linked to a heavy chain by one covalent disulfide bond, while the number of disulfide linkages varies among the heavy chains of different immunoglobulin isotypes. Each heavy and light chain also has regularly spaced intrachain disulfide bridges. Each heavy chain has at one end a variable domain (VH) followed by a number of constant domains. Each light chain has a variable domain at one end (VL) and a constant domain at its other end. The constant domain of the light chain is aligned with the first constant domain of the heavy chain, and the light chain variable domain is aligned with the variable domain of the heavy chain. Particular amino acid residues are believed to form an interface between the light chain and heavy chain variable domains.

There are five major classes of immunoglobulins: IgA, IgD, IgE, IgG, and IgM, and several of these may be further divided into subclasses (isotypes), e.g., $IgG_1$, $IgG_2$, $IgG_3$, $IgG_4$, $IgA_1$, and $IgA_2$. An antibody may be part of a larger fusion molecule, formed by covalent or non-covalent association of the antibody with one or more other proteins or peptides. An antibody may also be part of an immunoconjugate, wherein the antibody is conjugated to a second molecule (e.g., a toxin, radioisotope, or label.)

The term "monoclonal antibody," as used herein, refers to an antibody obtained from a population of substantially homogeneous antibodies, i.e., the individual antibodies are identical except for possible mutations that may be present in minor amounts.

"Humanized" forms of non-human antibodies are antibodies or fragments thereof that contain a framework region (FR) having substantially the amino acid sequence of a human immunoglobulin and a complementarity determining region (CDR) having substantially the amino acid sequence of a non-human immunoglobulin (i.e., the "import"sequence). In some instances, framework region residues of the human immunoglobulin are replaced by corresponding non-human residues. Further modifications of the humanized antibody may be made to refine antibody performance.

By "complementarity determining region" or "CDR" is meant one of the three hypervariable sequences in the variable regions within each of the immunoglobulin light and heavy chains.

By "framework region" or "FR" is meant the sequences of amino acids located on either side of the three CDRs of the immunoglobulin light and heavy chains. The FRs and CDRs of a humanized antibody need not correspond precisely to the parental sequences, e.g., the import CDR or the consensus FR may be mutagenized by substitution, insertion, or deletion of at least one residue so that the CDR or FR residue at that site does not correspond to either the consensus or the import sequence. Such mutations, however, will generally not be extensive. Usually, at least 75%, 80%, 85%, 90%, 95%, or 99% of the humanized antibody residues will correspond to the residues of the parental sequences.

The term "about," as used herein, when referring to a measurable value such as an amount, a temporal duration, and the like, is meant to encompass variations of up to ±20%, preferably ±10%, more preferably ±5%, even more preferably ±2% from the specified value, as such variations are appropriate to perform the disclosed methods. Unless otherwise indicated, all numbers expressing quantities of ingredients, properties such as molecular weight, reaction conditions, and so forth used in the specification and claims are to be understood as being modified in all instances by the term "about."Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

By "an amount sufficient" or "effective amount" is meant the amount of a therapeutic antibody or pharmaceutical composition thereof required to treat or ameliorate a disorder, such as an inflammatory disorder, in a clinically relevant manner. A sufficient amount of a therapeutic anti-FKN antibody, FKN-binding fragment or pharmaceutical composition thereof used to practice the present invention for therapeutic treatment of, e.g., an inflammatory disorder varies depending upon the manner of administration, age, and general health of the patient.

"Binding affinity" generally refers to the strength of the sum total of noncovalent interactions between a single binding site of a molecule (e.g., an antibody) and its binding partner (e.g., an antigen). Binding affinity can be represented by the dissociation constant (Kd). Affinity can be measured by methods known in the art, including radiolabeled FKN-binding assays (RIA) or by surface plasmon resonance assays (e.g., BIACORE®).

"Chimeric" or "chimerized" antibodies (i.e., immunoglobulins) refer to antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass, as well as fragments of such antibodies, so long as they exhibit the desired biological activity (Morrison et al., *Proc. Natl. Acad. Sci. U.S.A.* 81:6851-6855, 1984).

By "epitope" or "antigenic determinant" is meant a sequence of amino acids which, either as a result of linear structure or three-dimensional conformation, forms the binding site for an antibody. A conformational epitope, which may include discontinuous sections of an antigen's amino acid sequence, interacts with an antibody as a result of the tertiary structure of the epitope. In contrast, a linear epitope is an epitope that is recognized by antibodies based on its primary structure. In one embodiment, the epitope of fractalkine that forms the minimal interface with Fab includes, e.g., E66-Q69, W81-Q87, H70-F73, and 1188-D90.

The terms "express" and "produce" are used synonymously herein, and refer to the biosynthesis of a gene product. These terms encompass the transcription of a gene into RNA. These terms also encompass translation of RNA into one or more polypeptides, and further encompass all naturally occurring post-transcriptional and post-translational modifications. The expression/production of an antibody can be within the cytoplasm of the cell, and/or into the extracellular milieu such as the growth medium of a cell culture.

By "fractalkine," "FKN," "FK," or "neurotactin" is meant a polypeptide that is homologous to the polypeptide defined by SEQ ID NO: 1 (FIG. 1) and that has FKN biological activity (e.g., binds to the CX3CR1 receptor; chemoattracts T cells and monocytes; or promotes adhesion of leukocytes to activated endothelial cells). The biological activity of a FKN polypeptide may be assayed using any standard method. As used herein, FKN also includes any FKN family member or isoform. See, e.g., U.S. Pat. No. 7,390,490, WO 2006/

046739, and U.S. Patent Application Publication No. 2006/0233710, hereby incorporated by reference.

An "FKN-binding fragment" includes a portion of an intact antibody, comprising the FKN-binding region thereof and capable of binding FKN. FKN-binding fragments can be Fab, Fab', F(ab')$_2$, or Fv fragments; diabodies; triabodies; tetrabodies; miniantibodies; Affibody molecules; minibodies; linear antibodies; single-chain antibody molecules; or multispecific antibodies formed from antibody fragments.

By "homologous" is meant any gene or protein sequence that bears at least 30%, 40%, 50%, 60%, 70%, 80%, 90%, 95%, 99% or more homology to a known gene or protein sequence over the length of the comparison sequence. A "homologous" protein can also have at least one biological activity of the comparison protein. For polypeptides, the length of comparison sequences will generally be at least 15, 20, 25, 35 or more amino acids. For nucleic acids, the length of comparison sequences will generally be at least 50, 60, 75, 100, 125 or more nucleotides. "Homology" can also refer to a substantial similarity between an epitope used to generate antibodies and the protein or fragment thereof to which the antibodies are directed. In this case, homology refers to a similarity sufficient to elicit the production of antibodies that can specifically recognize the protein at issue.

"Human antibody" means that the antibody is either solely from human origin or any antibody in which the variable and constant domain sequences are human sequences or sequences of human antibodies. The term encompasses antibodies with sequences derived from (i.e., that utilize) human genes, but which have been changed, e.g., to decrease possible immunogenicity, increase affinity, eliminate cysteines that may cause undesirable folding, etc. The term encompasses such antibodies produced recombinantly in non-human cells, which may impart glycosylation not typical of human cells.

"Hybridoma" refers to the product of a cell-fusion between a cultured neoplastic lymphocyte and a primed B- or T-lymphocyte, which expresses the specific immune potential of the parent cell.

An "inflammatory disorder" as used herein refers to any disease, disorder, or condition in which the immune system is abnormally activated. The inflammatory disorder may be, e.g., ulcerative colitis, Crohn's disease, inflammatory bowel disease, rheumatoid arthritis, myositis, multiple sclerosis, neuromyelitis optica, atherosclerosis, psoriasis, systemic lupus erythematosus (e.g., lupus of the central nervous system or lupus nephritis), nephritis, glomerulonephritis, autoimmune hepatobiliary disease (e.g., autoimmune hepatitis, primary biliary cirrhosis, or primary sclerosing cholangitis), graft-versus-host disease, atopic dermatitis, asthma, neurodegenerative disease (e.g., Alzheimer's disease), demyelinating polyradiculopathy (e.g., Guillain-Barré syndrome or chronic inflammatory demyelinating polyradiculopathy), neuropathic pain, visceral pain of cancer, atherosclerosis, age-related macular degeneration, diabetic nephropathy, sarcoidosis-origined uveitis, or diabetes mellitus.

Alternatively, the disease, disorder, or condition is a disease of the upper or lower respiratory tract, for example, lymphomatous tracheobronchitis; allergic hypersensitivity or a hypersecretion condition, such as chronic bronchitis and cystic fibrosis; pulmonary fibrosis of various etiologies (e.g., idiopathic pulmonary fibrosis); chronic obstructive pulmonary disease (COPD); sarcoidosis; allergic and non-allergic rhinitis; allergic or non-allergic urticaria; a skin-related disease characterized by deregulated inflammation, tissue remodeling, angiogenesis, and neoplasm; a disease of the gastrointestinal tract, such as Hirschsprung's disease, diarrhea, malabsorption conditions, and inflammatory conditions; a disorder of the central and peripheral nervous system, such as depression, anxiety states, Parkinson's disease, migraine and other forms of cranial pain, strokes, and emesis; a disease of the immune system, such as in the splenic and lymphatic tissues, an autoimmune disease, or other immune-related disease; a disease of the cardiovascular system, such as pulmonary edema, hypertension, pre-eclampsia, complex regional pain syndrome type 2, and stroke; chronic inflammatory disease, such as arthritis; a bone-related disease; chronic pain, such as fibromyalgia; and other disorders in which the action of neurokinins, tachykinins, or other related substances (e.g., hemokinins) are involved in the pathogenesis, pathology, and etiology.

Additional examples of inflammatory disorders are acne vulgaris; acute respiratory distress syndrome; Addison's disease; allergic intraocular inflammatory diseases; ANCA-associated small-vessel vasculitis; ankylosing spondylitis; autoimmune hemolytic anemia; Behcet's disease; Bell's palsy; bullous pemphigoid; cerebral ischemia; cirrhosis; Cogan's syndrome; contact dermatitis; Cushing's syndrome; dermatomyositis; discoid lupus erythematosus; eosinophilic fasciitis; erythema nodosum; exfoliative dermatitis; focal glomerulosclerosis; focal segmental glomerulosclerosis; segmental glomerulosclerosis; giant cell arteritis; gout; gouty arthritis; hand eczema; Henoch-Schonlein purpura; herpes gestationis; hirsutism; idiopathic ceratoscleritis; idiopathic thrombocytopenic purpura; immune thrombocytopenic purpura inflammatory bowel or gastrointestinal disorders; inflammatory dermatoses; lichen planus; lymphomatous tracheobronchitis; macular edema; myasthenia gravis; nonspecific fibrosing lung disease; osteoarthritis; pancreatitis; pemphigoid gestationis; pemphigus vulgaris; periodontitis; polyarteritis nodosa; polymyalgia rheumatica; pruritus scroti; pruritus/inflammation; psoriatic arthritis; pulmonary histoplasmosis; relapsing polychondritis; rosacea; sarcoidosis; scleroderma; septic shock syndrome; shoulder tendinitis or bursitis; Sjogren's syndrome; Still's disease; Sweet's disease; systemic sclerosis; Takayasu's arteritis; temporal arteritis; toxic epidermal necrolysis; transplant-rejection and transplant-rejection-related syndromes; tuberculosis; type-1 diabetes; vasculitis; Vogt-Koyanagi-Harada (VKH) disease; and Wegener's granulomatosis.

"Isolated" or "purified" means altered "by the hand of man" from the natural state. If a molecule or composition occurs in nature, it has been "isolated" or "purified"if it has been changed or removed from its original environment, or both. For example, a polynucleotide or a polypeptide naturally present in a living plant or animal is not "isolated" or "purified," but the same polynucleotide or polypeptide separated from the coexisting materials of its natural state is "isolated" or "purified" as the term is employed herein.

The term "operably linked" or "operably inserted" means that the regulatory sequences necessary for expression of the coding sequence are placed in a nucleic acid molecule in the appropriate positions relative to the coding sequence so as to enable expression of the coding sequence. By way of example, a promoter is operably linked with a coding sequence when the promoter is capable of controlling the transcription or expression of that coding sequence. Coding sequences can be operably linked to promoters or regulatory sequences in a sense or antisense orientation. The term "operably linked" is sometimes applied to the arrangement of other transcription control elements (e.g., enhancers) in an expression vector.

"Polynucleotide," synonymously referred to as "nucleic acid molecule," refers to any polyribonucleotide or polydeoxyribonucleotide, which may be unmodified RNA or DNA or modified RNA or DNA. "Polynucleotides" include, without limitation, single- and double-stranded DNA, DNA that is a mixture of single- and double-stranded regions, single- and double-stranded RNA, and RNA that is mixture of single- and double-stranded regions, hybrid molecules comprising DNA and RNA that may be single-stranded, or, more typically, double-stranded or a mixture of single- and double-stranded regions. In addition, "polynucleotide" refers to triple-stranded regions comprising RNA or DNA or both RNA and DNA. The term polynucleotide also includes DNAs or RNAs containing one or more modified bases and DNAs or RNAs with backbones modified for stability or for other reasons. "Modified" bases include, for example, tritylated bases and unusual bases such as inosine. A variety of modifications can be made to DNA and RNA; thus, "polynucleotide" embraces chemically, enzymatically, or metabolically modified forms of polynucleotides as typically found in nature, as well as the chemical forms of DNA and RNA characteristic of viruses and cells. "Polynucleotide" also embraces relatively short nucleic acid chains, often referred to as oligonucleotides.

"Polypeptide" refers to both short chains, commonly referred to as peptides, oligopeptides, or oligomers, and to longer chains, generally referred to as proteins. Polypeptides may contain amino acids other than the 20 gene-encoded amino acids. "Polypeptides" include amino acid sequences modified either by natural processes, such as post-translational processing, or by chemical modification techniques which are well known in the art. Such modifications are well described in basic texts and in more detailed monographs, as well as in a voluminous research literature. Modifications can occur anywhere in a polypeptide, including the peptide backbone, the amino acid side-chains, and the amino or carboxyl termini. It will be appreciated that the same type of modification may be present in the same or varying degrees at several sites in a given polypeptide. Also, a given polypeptide may contain many types of modifications. Polypeptides may be branched as a result of ubiquitination, and they may be cyclic, with or without branching. Cyclic, branched and branched cyclic polypeptides may result from natural post-translational processes or may be made by synthetic methods. Modifications include, e.g., acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cystine, formation of pyroglutamate, formylation, gamma-carboxylation, glycosylation, GPI anchor formation, hydroxylation, iodination, methylation, myristoylation, oxidation, proteolytic processing, phosphorylation, prenylation, racemization, selenoylation, sulfation, and transfer-RNA mediated addition of amino acids to proteins such as arginylation, and ubiquitination. See, for instance, Proteins—Structure and Molecular Properties, 2nd Ed., T. E. Creighton, W.H. Freeman and Company, New York, 1993 and Wold, F., Posttranslational Protein Modifications: Perspectives and Prospects, pgs. 1-12 in Posttranslational Covalent Modification of Proteins, B. C. Johnson, Ed., Academic Press, New York, 1983; Seifter et al., Analysis for Protein Modifications and Nonprotein Cofactors, Meth Enzymol (1990) 182:626-646 and Rattan et al., Protein Synthesis: Posttranslational Modifications and Aging, Ann NY Acad Sci (1992) 663:48-62.

By "specifically binds" is meant an antibody or fragment thereof recognizes and binds an antigen (e.g., FKN or a fragment thereof), but that does not substantially recognize and bind other molecules in a sample (e.g., a biological sample). "Specifically" is meant to distinguish the low-level, non-specific stickiness that can sometimes occur between random proteins, e.g., with exposed hydrophilic domains. It is not meant to imply that the antibody will not bind to any protein other than antigen of the invention. Antibodies could cross-react (and "bind specifically") with any protein that includes the relevant epitope.

By "subject" is meant is meant any animal, e.g., a mammal (e.g., a human). A subject who is being treated for, e.g., an inflammatory disorder is one who has been diagnosed by a medical or veterinary practitioner as the case may be as having such a condition. Diagnosis may be performed by any suitable means. One in the art will understand that subjects of the invention may have been subjected to standard tests or may have been identified, without examination, as one at high risk due to the presence of one or more risk factors, such as age, genetics, or family history.

A cell has been "transformed" or "transfected" by exogenous or heterologous nucleic acids such as DNA when such DNA has been introduced inside the cell. The transforming DNA may or may not be integrated (e.g., covalently linked) into the genome of the cell. In prokaryotes, yeast, and mammalian cells, for example, the transforming DNA may be maintained on an episomal element such as a plasmid. With respect to eukaryotic cells, a stably transformed cell, or "stable cell" is one in which the transforming DNA has become integrated into a chromosome so that it is inherited by daughter cells through chromosome replication. This stability is demonstrated by the ability of the eukaryotic cell to establish cell lines or clones comprised of a population of daughter cells containing the transforming DNA. A "clone" is a population of cells derived from a single cell or common ancestor by mitosis. A "cell line" is a clone of a primary cell that is capable of stable growth in vitro for many generations.

By "treating" is meant administering a therapeutic antibody or a pharmaceutical composition thereof for prophylactic and/or therapeutic purposes. To "treat a disease or disorder" or use for "therapeutic treatment" refers to administering treatment to a subject already suffering from a disease to improve the subject's condition. The subject may be diagnosed with an inflammatory disorder based on identification of any of the characteristic symptoms or the use of the diagnostic methods known to one of skill in the art. To "prevent a disease or disorder" refers to prophylactic treatment of a subject who is not yet ill, but who is susceptible to, or otherwise at risk of, developing a particular disease. A subject is determined to be at risk of developing an inflammatory disorder using the diagnostic methods known in the art.

A "vector" is a replicon, such as plasmid, phage, cosmid, or virus in which another nucleic acid segment may be operably inserted so as to bring about the replication or expression of the segment.

As used in this specification and the appended claims, the singular forms "a," "an," and "the" include plural referents unless the context clearly dictates otherwise. Thus, for example, reference to "a cell" includes a combination of two or more cells, and the like.

Other features and advantages of the invention will be apparent from the detailed description and from the claims.

BRIEF DESCRIPTION OF THE DRAWINGS

FIG. 1 is the amino acid sequence of human FKN.

FIG. 2 is a table showing the binding characteristics (i.e., neutralizing activity, binding affinity, and species cross-reactivity) of anti-FKN monoclonal antibodies.

FIG. 4 is an alignment of the light chain variable regions of the humanized anti-FKN mAb sequences (SEQ ID NOS 38 and 44-45, respectively, in order of appearance), the m3A5-2 sequence (SEQ ID NO: 27), the germline Ig sequence (SEQ ID NO: 41), and the ABU90602.1 sequence (SEQ ID NO: 35).

FIG. 5 is a table summarizing the results from three independent chemotaxis assays. The neutralizing activities of humanized anti-hFKN mAbs were analyzed using a chemotaxis assay. All combinations of H3 and H3-2 with L2 and L4 were successfully humanized, as these mAbs showed similar neutralizing activity with the chimeric mAb. However, HK2, which was made by using narrowed key residues, showed decreased neutralizing activity in combination with L2 or L4.

FIGS. 6A and 6B depict a series of graphs showing the neutralizing activities of m3A5-2 mAb and chimeric mAb. FIG. 6A is a graph showing the neutralizing activity of m3A5-2 mAb as determined by a chemotaxis assay. FIG. 6B is a graph showing the neutralizing activity of the chimeric mAb as determined by a chemotaxis assay.

FIG. 7A shows the neutralizing activity of H3L2-IgG2. FIG. 7B shows the neutralizing activity of H3-L4-IgG2. FIG. 7C shows the neutralizing activity of HK2L2-IgG2. FIG. 7D shows the neutralizing activity of HK2L4-IgG2.

FIG. 8A shows the neutralizing activity of H3-2L2-IgG2. FIG. 8B shows the neutralizing activity of H3-2L4-IgG2. FIG. 8C shows the neutralizing activity of H3-2L5-IgG2. FIG. 8D shows the neutralizing activity of HK3L2-IgG2. FIG. 8E shows the neutralizing activity of HK3L4-IgG2. FIG. 8F shows the neutralizing activity of HK3L5-IgG2.

FIG. 9 is a table summarizing the results from BIACORE® assays used to measure binding affinity of the mAbs to hFKN and cynomolgus monkey FKN.

FIG. 10A is a bar graph showing the Ka values (1/Ms). FIG. 10B is a bar graph showing the Kd values (1/s). FIG. 10C is a bar graph showing the KD values (M).

DETAILED DESCRIPTION

Figure 3:
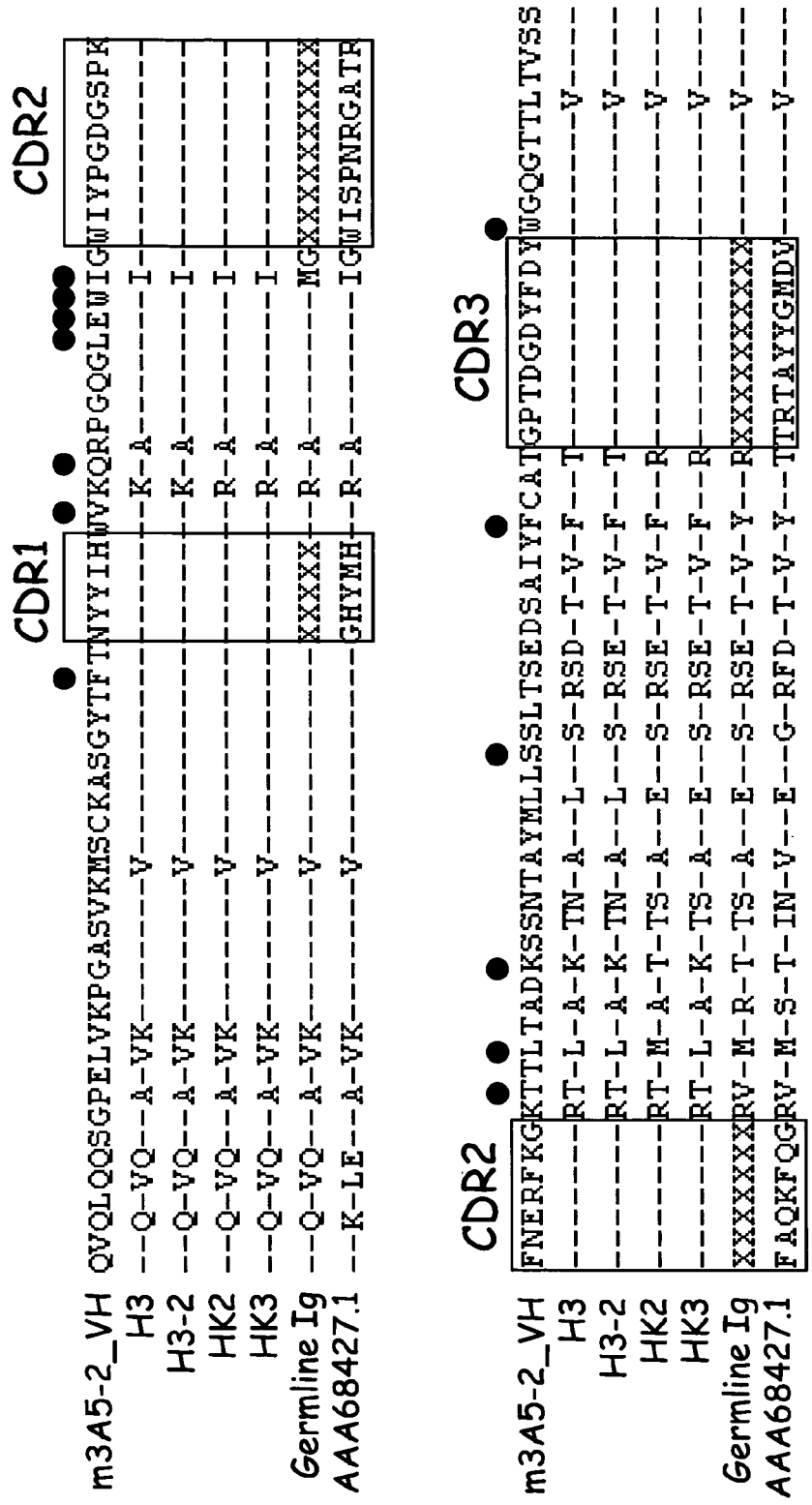
FIG. 3 is an alignment of the heavy chain variable regions of the humanized anti-FKN mAb sequences (SEQ ID NOS 36-37 and 42-43, respectively, in order of appearance), the m3A5-2 sequence (SEQ ID NO: 26), the germline Ig sequence (SEQ ID NO: 40), and the AAA68427.1 sequence (SEQ ID NO: 34).
Figure 7:
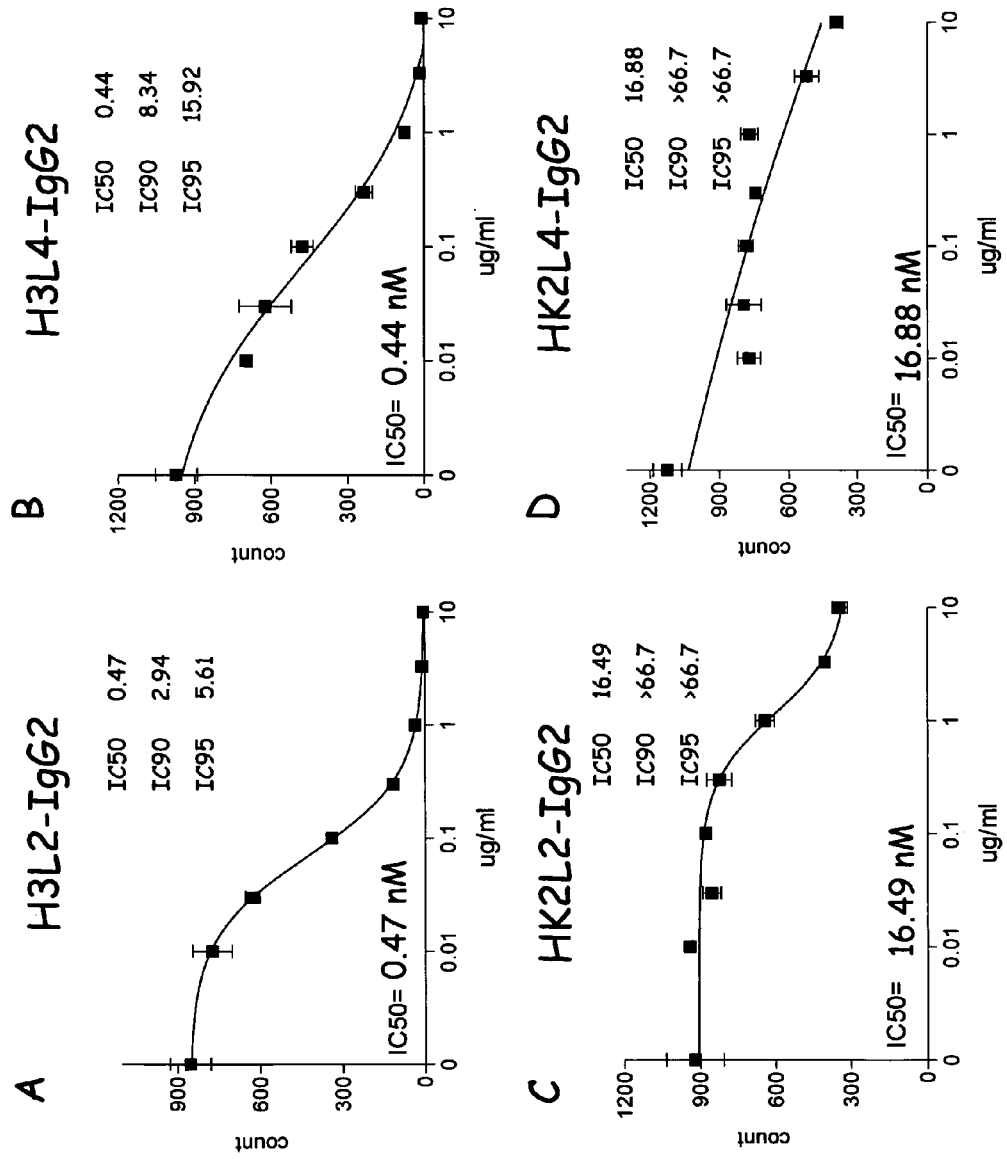
FIGS. 7A-7D depict a series of graphs showing the neutralizing activities of humanized anti-hFKN antibodies as determined by a chemotaxis assay.
Figure 8:
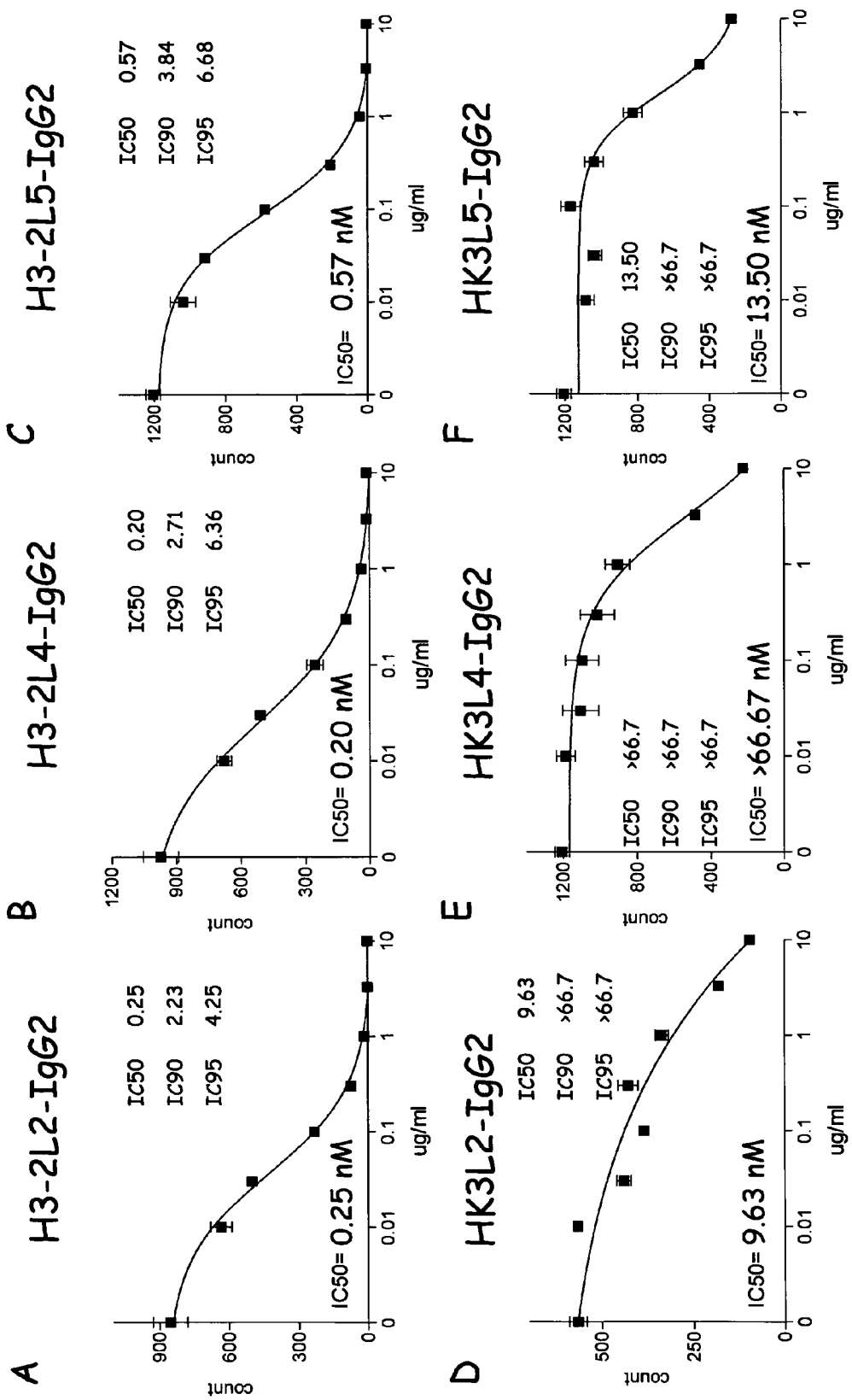
FIGS. 8A-8F depict a series of graphs showing the neutralizing activities of humanized anti-hFKN antibodies as determined by a chemotaxis assay.
Figure 10:
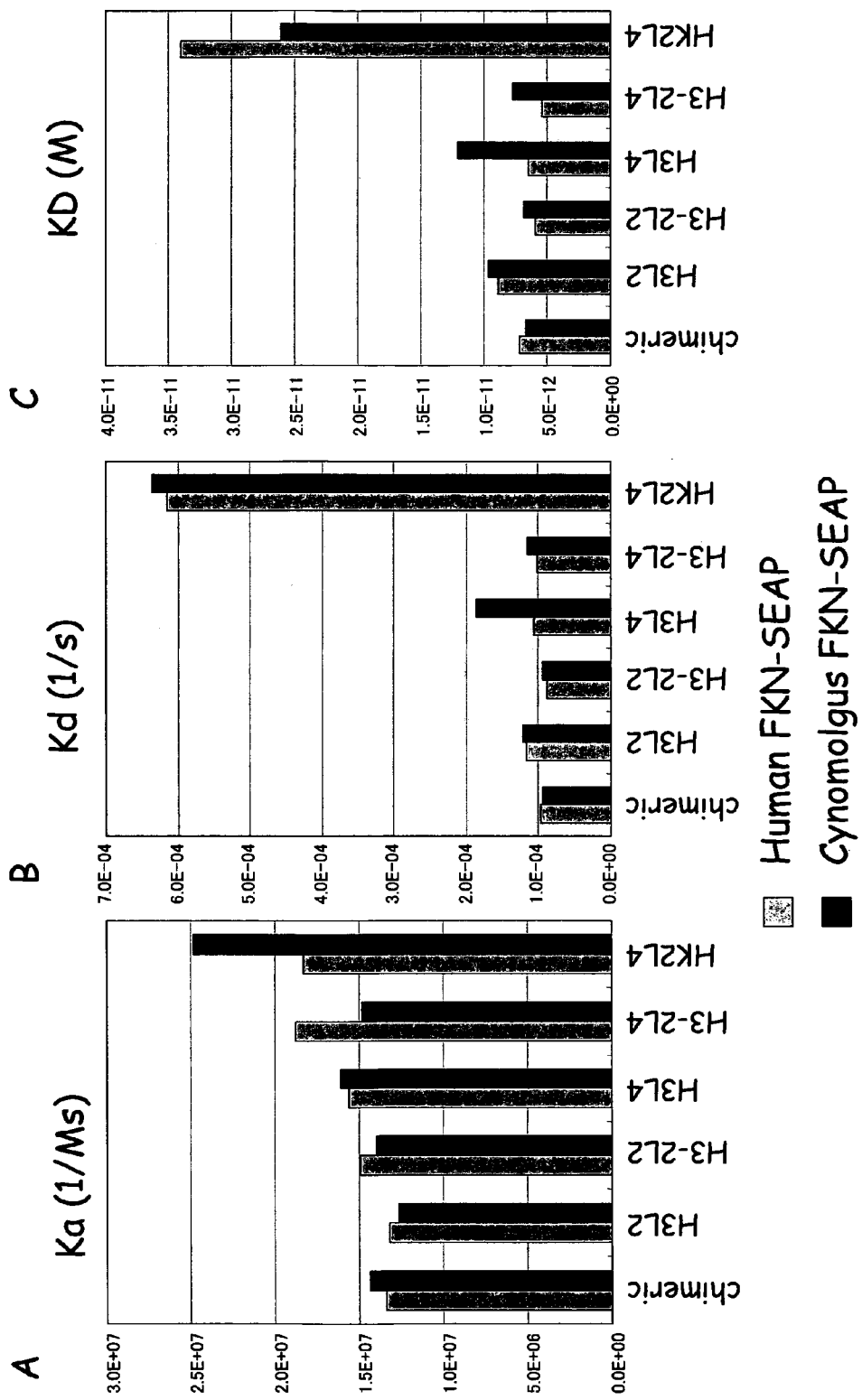
FIGS. 10A-10C depict a series of graphs showing the binding affinities of the chimeric and humanized anti-hFKN antibodies (H3L2, H3-2L2, H3L4, H3-2L4, and HK2L4) to hFKN-SEAP and cynomolgus monkey FKN-SEAP as determined by a BIACORE® assay.

We have designed and isolated chimeric anti-FKN antibodies, humanized anti-FKN antibodies, and FKN-binding fragments thereof. The humanized anti-FKN antibodies and FKN-binding fragments thereof featured herein may be used to treat inflammatory disorders. Such antibodies may also be used to inhibit the recruitment of leukocytes to an inflammation site. Inflammatory disorders that can be treated according to the invention include ulcerative colitis, Crohn's disease, inflammatory bowel disease, rheumatoid arthritis, myositis, multiple sclerosis, neuromyelitis optica, atherosclerosis, psoriasis, systemic lupus erythematosus (e.g., lupus of the central nervous system or lupus nephritis), nephritis, glomerulonephritis, autoimmune hepatobiliary disease (e.g., autoimmune hepatitis, primary biliary cirrhosis, or primary sclerosing cholangitis), graft-versus-host disease, atopic dermatitis, asthma, neurodegenerative disease (e.g., Alzheimer's disease), demyelinating polyradiculopathy (e.g., Guillain-Barré syndrome or chronic inflammatory demyelinating polyradiculopathy), neuropathic pain, visceral pain of cancer, atherosclerosis, age-related macular degeneration, diabetic nephropathy, sarcoidosis-origined uveitis, diabetes mellitus, lymphomatous tracheobronchitis, allergic hypersensitivity or a hypersecretion condition, such as chronic bronchitis and cystic fibrosis, pulmonary fibrosis of various etiologies (e.g., idiopathic pulmonary fibrosis), chronic obstructive pulmonary disease (COPD), sarcoidosis, allergic and non-allergic rhinitis, allergic or non-allergic urticaria, a skin-related disease characterized by deregulated inflammation, tissue remodeling, angiogenesis, and neoplasm, a disease of the gastrointestinal tract, such as Hirschsprung's disease, diarrhea, malabsorption conditions, and inflammatory conditions, a disorder of the central and peripheral nervous system, such as depression, anxiety states, Parkinson's disease, migraine and other forms of cranial pain, strokes, and emesis, a disease of the immune system, such as in the splenic and lymphatic tissues, an autoimmune disease, or other immune-related disease, a disease of the cardiovascular system, such as pulmonary edema, hypertension, pre-eclampsia, complex regional pain syndrome type 2, and stroke, chronic inflammatory disease, such as arthritis, a bone-related disease, chronic pain, such as fibromyalgia, acne vulgaris, acute respiratory distress syndrome, Addison's disease, allergic intraocular inflammatory diseases, ANCA-associated small-vessel vasculitis, ankylosing spondylitis, autoimmune hemolytic anemia, Behcet's disease, Bell's palsy, bullous pemphigoid, cerebral ischemia, cirrhosis, Cogan's syndrome, contact dermatitis, Cushing's syndrome, dermatomyositis, discoid lupus erythematosus, eosinophilic fasciitis, erythema nodosum, exfoliative dermatitis, focal glomerulosclerosis, focal segmental glomerulosclerosis, segmental glomerulosclerosis, giant cell arteritis, gout, gouty arthritis, hand eczema, Henoch-Schonlein purpura, herpes gestationis, hirsutism, idiopathic ceratoscleritis, idiopathic thrombocytopenic purpura, immune thrombocytopenic purpura inflammatory bowel or gastrointestinal disorders, inflammatory dermatoses, lichen planus, lymphomatous tracheobronchitis, macular edema, myasthenia gravis, nonspecific fibrosing lung disease, osteoarthritis, pancreatitis, pemphigoid gestationis, pemphigus vulgaris, periodontitis, polyarteritis nodosa, polymyalgia rheumatica, pruritus scroti, pruritis/inflammation, psoriatic arthritis, pulmonary histoplasmosis, relapsing polychondritis, rosacea, sarcoidosis, scleroderma, septic shock syndrome, shoulder tendinitis or bursitis, Sjogren's syndrome, Still's disease, Sweet's disease, systemic sclerosis, Takayasu's arteritis, temporal arteritis, toxic epidermal necrolysis, transplant-rejection and transplant-rejection-related syndromes, tuberculosis, type-1 diabetes, vasculitis, Vogt-Koyanagi-Harada (VKH) disease, and Wegener's granulomatosis.

Antibodies

Methods for making and purifying antibodies or FKN-binding fragments thereof are well known in the art. See, e.g., Kohler et al., *Nature* 256:495-497 (1975); Hongo et al., *Hybridoma* 14:253-260 (1995); Harlow et al., *Antibodies: A Laboratory Manual* (Cold Spring Harbor Laboratory Press), 2nd ed. (1988); Hammerling et al., Monoclonal Antibodies and T-Cell Hybridomas (Elsevier), 563-681 (1981); Ni, Xiandai Mianyixue, 26:265-268 (2006); U.S. Pat. Nos. 7,189,826; 7,078,492; and 7,153,507; Vollmers and Brandlein, *Histology and Histopathology* 20:927-937 (2005); Vollmers and Brandlein, *Methods and Findings in Experimental and Clinical Pharmacology* 27:185-191 (2005); US 2006/258841; US 2006/183887; US 2006/059575; US 2005/287149; US 2005/100546; and US 2005/026229.

Chimeric Antibodies

Chimeric antibodies and methods to produce them are well known and established in the art. As used herein, the term "chimeric antibody" means an antibody, or FKN-binding fragment thereof, having at least some portion of at least one variable domain derived from the antibody amino acid sequence of a non-human mammal, a rodent, or a reptile, while the remaining portions of the antibody, or FKN-binding fragment thereof, are derived from a human. For example, a chimeric antibody may comprise a mouse antigen binding domain with a human Fc or other such structural domain.

Humanized Antibodies

The invention encompasses humanized anti-FKN antibodies and FKN-binding fragments thereof that, for example, modulate the interaction between FKN and CX3CR1. Humanization can be performed by means of the complementarity determining region (CDR)-grafting method (Kontermann and Dübel, Antibody Engineering, Springer Lab Manual (2001) and Tsurushita et al., *Methods* 36:69-83 (2005)). Humanization can be also performed following methods known in the art (see, e.g., Jones et al., *Nature* 321:522-525 (1986); Riechmann et al., *Nature* 332:323-327 (1988); and Verhoeyen et al., *Science* 239:1534-1536 (1988)) by substituting hypervariable region sequences for the corresponding sequences of a human antibody. Humanized antibodies are typically human antibodies in which some hypervariable region residues and possibly some FR residues are substituted by residues from analogous sites in non-human antibodies.

The choice of human variable domains, both light and heavy, to be used in making the humanized antibodies can be important to reduce antigenicity. According to the "best-fit" method, the sequence of the variable domain of a rodent antibody is screened against the entire library of known human variable-domain sequences. The human sequence that is closest to that of the rodent is then accepted as the human framework for the humanized antibody. See, e.g., Sims et al., *J. Immunol.* 151:2296-2308 (1993) and Chothia et al., *J. Mol. Biol.* 196:901-917 (1987). Another method uses a particular framework derived from the consensus sequence of all human antibodies of a particular subgroup of light or heavy chains. The same framework may be used for several different humanized antibodies. See, e.g., Carter et al., *Proc. Natl. Acad. Sci. USA* 89:4285-4289 (1992) and Presta et al., *J. Immunol.* 151:2623-2632 (1993).

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s) (e.g., FKN or a fragment thereof), is achieved. In general, the CDR residues are directly and most substantially involved in influencing antigen binding.

FKN-Binding Fragments

In certain embodiments of the invention, there is provided FKN-binding fragments that modulate the interaction between FKN and CX3CR1. Such fragments may be functional antigen binding fragments of intact, humanized, and/or chimeric antibodies, such as Fab, Fab', $F(ab')_2$, Fv, or ScFv fragments (see, e.g., Bird et al., *Science* 242:423-426 (1998)) Such fragments are produced by the proteolytic digestion of intact antibodies by, e.g., papain digestion (see, e.g., WO 94/29348) directly from recombinantly transformed host cells. FKN-binding fragments may be produced using a variety of engineering techniques described below.

Fv fragments have a lower interaction energy between their two chains than Fab fragments. To stabilize the association of the VH and VL domains, Fv fragments have been linked with peptides (see, e.g., Bird et al., *Science* 242:423-426 (1998) and Huston et al., *PNAS* 85:5879-5883 (1998)), disulfide bridges (see, e.g., Glockshuber et al., *Biochemistry* 29:1362-1367 (1990)), and "knob in hole" mutations (see, e.g., Zhu et al., *Protein Sci.* 6:781-788 (1997)). ScFv fragments can be produced by methods well known to those skilled in the art (see, e.g., Whitlow et al., *Methods Enzymol.* 2:97-105 (1991) and Huston et al., *Int. Rev. Immunol.* 10:195-217 (1993)). ScFv may be produced in bacterial cells such as *E. coli*, but may also be produced in eukaryotic cells. One disadvantage of ScFv is the monovalency of the product, which precludes an increased avidity due to polyvalent binding, and the short half-life of ScFv fragments. Attempts to overcome these problems include bivalent $(ScFv')_2$ produced from ScFV containing an additional C-terminal cysteine by chemical coupling (see, e.g., Adams et al., *Cancer Res.* 53:4026-4034 (1993) and McCartney et al., *Protein Eng.* 8:301-314 (1995)) or by spontaneous site-specific dimerization of ScFv containing an unpaired C-terminal cysteine residue (see, e.g., Kipriyanov et al., *Cell. Biophys.* 26:187-204 (1995)). Alternatively, ScFv can be forced to form multimers by shortening the peptide linker to 3 to 12 residues to form "diabodies" (see, e.g., Holliger et al., *PNAS* 90:6444-6448 (1993)). Reducing the linker further can result in ScFV trimers to form "triabodies" (see, e.g., Kortt et al., *Protein Eng.* 10:423-433 (1997)) and tetramers to form "tetrabodies" (see, e.g., Le Gall et al., *FEBS Letters* 453:164-168 (1999)). Construction of bivalent ScFV molecules can also be achieved by genetic fusion with protein dimerizing motifs to form "miniantibodies" (see, e.g., Pack et al., *Biochemistry* 31:1579-1584 (1992)) and "minibodies" (see, e.g., Hu et al., *Cancer Res.* 56:3055-3061 (1996)). ScFv-Sc-Fv tandems ((ScFV)$_2$) may also be produced by linking two ScFv units by a third peptide linker (see, e.g., Kurucz et al., *J. Immunol.* 154:4576-4582 (1995)). Bispecific diabodies can be produced through the noncovalent association of two single chain fusion products containing a VH domain from one antibody connected by a short linker to the VL domain of another antibody (see, e.g., Kipriyanov et al., *Int. J. Can.* 77:763-772 (1998)). The stability of such bispecific diabodies can be enhanced by the introduction of disulfide bridges or "knob in hole" mutations or by the formation of single chain diabodies (ScDb), wherein two hybrid ScFv fragments are connected through a peptide linker (see, e.g., Kontermann et al., *J. Immunol. Methods* 226:179-188 (1999)). Tetravalent bispecific molecules are available by, e.g., fusing a ScFv fragment to the CH3 domain of an IgG molecule or to a Fab fragment through the hinge region (see, e.g., Coloma et al., *Nature Biotechnol.* 15:159-163 (1997)). Alternatively, tetravalent bispecific molecules are available by the fusion of bispecific single chain diabodies (see, e.g., Alt et al., *FEBS Letters* 454:90-94 (1999)). Smaller tetravalent bispecific molecules can also be formed by the dimerization of either ScFv-ScFv tandems with a linker containing a helix-loop-helix motif (DiBi miniantibodies) (see, e.g., Muller et al., *FEBS Letters* 432:45-49 (1998)) or a single chain molecule comprising four antibody variable domains (VH and VL) in an orientation preventing intramolecular pairing (tandem diabody) (see, e.g., Kipriyanov et al., *J. Mol. Biol.* 293:41-56 (1999)). Bispecific F(ab')$_2$ fragments can be created by chemical coupling of Fab' fragments or by heterodimerization through leucine zippers (see, e.g., Shalaby et al., *J. Exp. Med.* 175:217-225 (1992) and Kostelny et al., *J. Immunol.* 148:1547-1553 (1992)). Also available are isolated VH and VL domains (see, e.g., U.S. Pat. Nos. 6,248,516; 6,291,158; and 6,172,197, hereby incorporated by reference).

Pharmaceutical Formulations

Therapeutic formulations comprising an antibody or FKN-binding fragment thereof of the invention may be combined with physiologically acceptable carriers, excipients, or stabilizers in the form of aqueous or dried formulations. Acceptable carriers, excipients, or stabilizers include, e.g., saline; buffers, such as phosphate, citrate, and other organic acids; antioxidants, including ascorbic acid; low molecular weight polypeptides; proteins (e.g., serum albumin, gelatin, or immunoglobulins); hydrophilic polymers such as polyvinylpyrrolidone; amino acids; monosaccharides, disaccharides, and other carbohydrates, including glucose, mannose, or dextrins; chelating agents, such as EDTA; sugar alcohols, such as mannitol or sorbitol; salt-forming counterions, such as sodium; or nonionic surfactants, such as TWEEN™, PLURONICS™, or PEG.

The antibodies or FKN-binding fragments thereof of the invention may be entrapped in microcapsules, in colloidal drug delivery systems (e.g., liposomes, albumin microspheres, microemulsions, nanoparticles, or nanocapsules), or in macroemulsions. Where sustained release administration of the antibody is desired in a formulation with release characteristics suitable for the treatment of any disorder requiring administration of the antibody, microencapsulation of the antibody may be contemplated. Examples of sustained-release matrices include polyesters, hydrogels (for example, poly(2-hydroxyethyl-methacrylate) or poly(vinylalcohol)), polylactides (see, e.g., U.S. Pat. No. 3,773,919), copolymers of L-glutamic acid and γ ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), and poly-D-(-)-3-hydroxybutyric acid.

The formulations to be used for in vivo administration must be sterile. This is readily accomplished by filtration through sterile filtration membranes.

Combination Therapies

Therapeutic antibodies or FKN-binding fragments thereof of the invention can be used either alone or in combination with other compositions in a therapy. For instance, an antibody of the invention may be co-administered with one or more of another antibody, anti-inflammatory agents, cytotoxic agents, anti-angiogenic agents, cytokines, growth inhibitory agents, or anti-TNF-α therapy. Such combined therapies include combined administration (where the two or more agents are included in the same or separate formulations) and separate administration (e.g., simultaneously or sequentially). When two or more agents are administered separately, administration of the antibody of the invention can occur prior to or following administration of the adjunct therapy.

The effective amounts of therapeutic agents administered in combination with an anti-FKN antibody or FKN-binding fragment thereof will be at a physician's discretion. The dosage determination is calculated to achieve maximal management of the conditions to be treated. The dose will additionally depend on such factors as the type of therapeutic agent to be used and the specific subject being treated. Suitable dosages can be lowered due to the combined action (synergy) of the additional therapeutic agent and the anti-FKN antibody or FKN-binding fragment thereof.

Anti-Inflammatory Agents

An anti-inflammatory compound may be administered in combination with the antibodies or FKN-binding fragments of the invention. Exemplary anti-inflammatory agents include steroids, such as a glucocorticoid, non-steroidal anti-inflammatory drugs (e.g., ibuprofen or tacrolimus), cyclooxygenase-2-specific inhibitors such as rofecoxib (Vioxx®) and celecoxib (Celebrex®), corticosteroids (e.g., prednisone or hydrocortisone), specific cytokines directed at T lymphocyte function, flubiprofen, diclofenac, and ketarolac. See, e.g., U.S. Pat. Nos. 7,112,578 and 7,199,119, hereby incorporated by reference.

Other Agents

Other therapeutic agents that may be administered include, e.g., aminosalicylates (e.g., 5-aminosalicylic acid), sulfasalazine (e.g., azulfadine), mesalamine (e.g., Asacol® or Pentasa®), azathioprine (e.g., Imuran®), 6-mercaptopurine (e.g., Purinethol®), cyclosporine, methotrexate, infliximab (e.g., Remicade®), interferons (e.g., interferon-β, glatiramer acetate (e.g., Copaxone®), natalizumab (Tysabri®), anti-integrin α4, ursodeoxycholic acid, tacrine hydrochloride, HMG CoA reductase inhibitor, lidocaine, sulfonylurea, cyclophosphamide, intravenous immunoglobulin, amitriptyline, opiates (e.g., morphine), diphenoxylate, atropine, vitamin D, calcium, lamotrigine, quetiapine, prostaglandin E1, nitroglycerin, pegaptanib, ranibizumab, isosorbide dinitrate, perospirone, topiramate, oxcarbazepine, dopamine, mycophenolate mofetil, mizoribine, levetiracetam, fentanyl, tramadol, digitalis, capsaicin, natriuretic peptide, cloridine, -dronates (e.g., alendronate), bezafibrate, mexiletine, glinides (e.g., nateglinide or repaglinide), donepezil hydrochloride, leflunomide, pregabalin, rivastigmine tartrate, phentanyl, prostacyclin, procainamide, colchicine, α-glucosidase inhibitors, diuretics (e.g., thiazide diuretics or anti-aldosterone diuretics), tacrolimus, memantine hydrochloride, pentazocine, clopidogrel, tissue plasminogen activator, thalidomide, angiotensin receptor blocker, thiazolidinedione, metronidazole, spironolactone, duloxetine, paroxetine, clonidine, ticlopidine, heparin, calcium channel blockers, insulin, albumin, bucillamine, carbamazepine, risperidone, limaprost, warfarin, verteporfin, gabapentin, galantamine hydrobromide, aspirin, urokinase, chlorambucil, angiotensin converting enzyme inhibitor, biguanides, β-adrenergic receptor inhibitors or agonists, hydrochloroquine, and mitoxantrone.

Treatment of a disorder described herein (e.g., an inflammatory disorder) may additionally involve administration of other therapies. For example, plasmapheresis (e.g., plasma exchange therapy) may be used to treat, for example, Guillain-Barré syndrome, demyelinating polyradiculopathy (e.g., chronic inflammatory demyelinating polyradiculopathy), thrombotic thrombocytopenic purpura (TTP), Behcet's disease, or multiple sclerosis.

Dosages and Administration

Alleviation or treatment of an inflammatory disorder generally involves the lessening of one or more symptoms or complications associated with the disorder. In the case of inflammatory disorders, the therapeutically effective amount of the therapeutic antibody, FKN-binding fragments, or pharmaceutical composition thereof can accomplish one or a combination of the following: reduce inflammation; reduce abdominal pain or cramping; reduce bloating; reduce or eliminate diarrhea; reduce ulceration of the digestive tract; reduce fever; reduce or relieve nausea; reduce fatigue; minimize weight loss; alleviate joint pain; reduce swelling; relieve itching or skin rashes; eliminate jaundice; and/or relieve one or more of the symptoms associated with an inflammatory disorder. The "therapeutically effective amount" of the antibody to be administered is the minimum amount necessary to prevent, ameliorate, or treat an inflammatory disorder.

The antibodies, FKN-binding fragments, and pharmaceutical composition described herein are administered to a subject in accordance with known methods, such as intravenous administration as a bolus or by continuous infusion over a period of time, topically, orally, subcutaneously, by bronchial injection, intracerebrally, intranasally, transdermally, intraperitoneally, intramuscularly, intrapulmonary, vaginally, rectally, intraarticularly, intraarterially, intralesionally, parenterally, intraventricularly in the brain, or intraocularly. Local administration may be particularly desired if extensive side effects or toxicity is associated with the treatment.

Formulations for oral use may also be provided as chewable tablets, or as hard gelatin capsules, wherein the active ingredient is mixed with an inert solid diluent, or as soft gelatin capsules wherein the active ingredient is mixed with water or an oil medium.

An ex vivo strategy can also be used for therapeutic applications. Ex vivo strategies involve transfecting or transducing cells obtained from the subject with a polynucleotide encoding an antibody or antibody fragment. The transfected or transduced cells are then returned to the subject. The cells can be any of a wide range of types including, without limitation, hemopoietic cells (e.g., bone marrow cells, macrophages, monocytes, dendritic cells, T cells, or B cells), fibroblasts, epithelial cells, endothelial cells, keratinocytes, or muscle cells:

The dosage and the timing of administering the compositions of the present invention depend on various clinical factors, including the overall health of the subject and the severity of the symptoms of the inflammatory disorder. Treatment can be continued for a period of time ranging from 1 day to 4 years, 1 day to 3 years, 1 day to 2 years, 1 day to a year, 1 to 100 days, 1 to 60 days, 1 to 20 days, 1 to 10 days, or until the inflammatory disorder or symptoms of the inflammatory disorder are treated or alleviated. The compositions of the present invention may be administered four times per day, three times per day, twice per day, daily, weekly, bi-monthly, monthly, every two months, every three months, or annually. Dosages vary depending on the severity of the condition and are titrated to achieve a steady-state blood serum concentration ranging from about 1 ng/mL to 10 μg/mL, or 1 to 500 ng/mL. The amount of antibody administered is typically in the range of about 0.001 to about 30 mg/kg of subject weight (e.g., 0.01 to about 10 mg/kg of subject weight).

EXAMPLES

The present invention is illustrated by the following examples, which are in no way intended to be limiting of the invention.

Example 1

Preparation of Mouse Anti-Human Fractalkine (hFKN) Monoclonal Antibodies

Mouse anti-hFKN monoclonal antibodies (mAbs) were generated as described previously (see, e.g., U.S. Pat. No. 7,390,490, hereby incorporated by reference). Neutralizing mAb clones 1F3-1, 3A5-2, 1F3, 1G1, 2B2, 3D5, 3H7, 6D1, 7F6, and 5H7-6 were obtained.

Example 2

Selection of Candidate mAb for Humanization

Clones 1F3-1, 3A5-2, and 5H7-6 were analyzed using chemotaxis assays for measuring neutralizing activity, BIACORE® assays for measuring binding affinity to hFKN, and enzyme-linked immunosorbent assays (ELISA) for measuring species cross-reactivity to cynomolgus monkey FKN. The neutralizing activity, binding affinity, and species cross-reactivity to cynomolgus monkey FKN are summarized in FIG. 2. Clone 3A5-2 showed the highest neutralizing activity and the highest binding affinity to hFKN. Clone 3A5-2 showed equal reactivity to cynomolgus monkey FKN and hFKN. Therefore, clone 3A5-2 was selected as a candidate for humanization.

Chemotaxis assays were performed as follows. Cells were placed in the upper wells of a transwell culture plate (Multi-Screen-MIC Plate, 5.0 μm, Millipore, Catalog No. MAMIC 5S10) with ligand in the lower wells. First, recombinant human FKN (R&D Systems, Catalog No. 362-CX/CF) (33 ng/ml final concentration) (FIG. 1) was pre-incubated with purified antibodies at various concentrations (0 to 10 μg/ml) at room temperature. The composition contained the following components: 10× chemokine solution, 15 μl/well; 10× purified mAb, 15 μl/well; and 1× chemotaxis buffer (0.5% BSA, 0.5% FBS, 20 mM HEPES (pH 7.4), 50 μM 2-mercaptoethanol in RPMI1640 (Invitrogen)), 120 μl/well. After 30 minutes, B300.19 cells transfected with CX3CR1 ($2 \times 10^5$ cells/75 μl) were applied to the upper wells and incubated in a 5%-$CO_2$ incubator at 37° C. for 4 hours. After the incubation, 150 μl of the solution of the lower wells were harvested, fixed with 50 μl of 4% PFA/PBS, and 30 μl of the samples were applied to the FACSCantoII cell analyzer to count migrated cells.

BIACORE® assays were performed as follows. Recombinant Protein-A/G (Pierce Chemical) was immobilized on BIACORE® sensor chips (CM5) that were pre-activated with amine coupling reagents (GE Healthcare). Purified mAbs were added into the sensor chips at a concentration of 0.2 µg/ml. Soluble antigens (soluble FKN conjugated to secreted alkaline phosphatase (SEAP) or control SEAP proteins) were added into the sensor chips at various concentrations (0 to 200 nM). Association of added antigens with mAbs captured on the sensor chips was monitored continuously, and the relative binding response of the antigens was determined using a BIACORE® A100 system (GE Healthcare).

ELISAs were performed as follows. Polyclonal anti-rabbit IgG antibody (Jackson ImmunoResearch Laboratories, Catalog No. 711-005-152) was coated on the wells of a 96-well plate (Nunc, Catalog No. 442402). After overnight incubation at 4° C., the wells were blocked with 1× Block-Ace (DainipponPharma) for 1 hour at room temperature. After washing three times with 0.05% Tween 20/PBS, 10 nM rabbit polyclonal anti-PLAP antibody (Biomeda) was added to the wells (50 µl/well). After incubating for 1 hour at room temperature and washing three times as described above, culture supernatants containing hFKN-SEAP or cynomolgus monkey FKN-SEAP were added (1 nM final concentration) to the wells and incubated for 1 hour at room temperature. After washing three times, purified anti-hFKN mAbs were added to the wells at various concentrations (0 to 10 µg/ml). After incubating for 1 hour and washing three times, horseradish peroxidase-conjugated anti-mouse IgG antibody (Jackson ImmunoResearch Laboratories, Catalog No. 715-036-151) was added at 0.16 µg/ml (50 µl/well) and incubated for 1 hour at room temperature. After washing three times, a TMB (3,3',5,5'-tetramethylbenzidine) solution was added to the wells and allowed to incubate for 15-30 minutes. An equal volume of stopping solution (2 M $H_2SO_4$) was added to the wells and the optical density at 450 nm was read by a microplate reader (Arvo, PerkinElmer).

Soluble hFKN-SEAP was prepared as follows. cDNA encoding the extracellular region of hFKN was amplified with 5'-SalI-hFKN primer (CGCGTCGACGCCACCAT-GGCTCCGATATCTCTGTC; SEQ ID NO: 2) and 3'-NotI-hFKN primer (GCGGGCG-CCGCCCTCCGGGTG-GCAGCCTGGG; SEQ ID NO: 3) and subcloned into pcDNA3.1 (+) dSalI SEAP vector containing SEAP cDNA. The expression vector of hFKN-SEAP was transfected into HEK293EBNA (HEK293E) cells (Invitrogen). HEK293E cells were inoculated with DMEM (Invitrogen) supplemented with 10% fetal bovine serum on the day before transfection. On the day of transfection, the medium was exchanged with OPTI-MEM II serum free media (Invitrogen). The expression vector was transfected with TransIT LT1 (TAKARA) according to the manufacturers'instructions. After 3 days of incubation (5% $CO_2$ at 37° C.), the culture supernatant was harvested. The concentration of SEAP protein was measured using Great EscAPe SEAP Chemiluminescence Kit 2.0 (Clontech).

Soluble cynomolgus monkey FKN-SEAP was prepared as follows. cDNA encoding the extracellular region of cynomolgus monkey FKN was amplified with 5'-XhoI-cynomolgus monkey FKN primer (GCGCTCGAGGCCACCATGGCTC-CGATA-TCTCTGTCGTGG; SEQ ID NO: 4) and 3'-NotI-cynomolgus monkey FKN primer (CGCGGCGGCCGCG-GTGGCAGCCTGGGAGTCAGGGAC; SEQ ID NO: 5) and subcloned into pENTR1A (Invitrogen) containing SEAP cDNA. The fragment encoding cynomolgus monkey FKN and SEAP was transferred to pcDNA3.1 containing cassette B by using the GATEWAY system (Invitrogen). Culture supernatant containing cynomolgus monkey FKN-SEAP was prepared as described above.

Example 3 cDNA Cloning of the Variable Regions of Heavy and Light Chains of Clone 3A5-2 Mouse Anti-hFKN mAb cDNAs of heavy and light chains of clone 3A5-2 were amplified by RT-PCR. The total RNA was extracted from the hybridoma of clone 3A5-2 with RNeasy Mini Kit (QIAGEN). By using the total RNA, cDNAs were synthesized using a cDNA synthesis kit (TAKARA) and amplified with 5'-Mm-HC-Leader1 primer (GGGATGGRATGSAG-CTGKGT-MATSCTCTT; SEQ ID NO: 6), 5'-Mm-HC-Leader2 primer (GGGATGRA-CTTCGGGYTGAGCTKGGTTTT; SEQ ID NO: 7), or 5'-Mm-HC-Leader3 primer (GGGATGGCT-GTCTTGGGGCTGCTCTTCT; SEQ ID NO: 8) and 3'-Mm-IgG2a-CH3-R primer (TCATTTACCCGGAGTCCGG-GAGAAGCTCTTAGTC; SEQ ID NO: 9) for the heavy chain and 5'-Mm-LC-Leader1 primer (GGGATGGAGACAGA-CACA-CTCCTGCTAT; SEQ ID NO: 10) or 5'-Mm-LC-Leader2 primer (GGGATGGATTTT-CAGGTGCA-GATTTTCAG; SEQ ID NO: 11) or 5'-Mm-LC-Leader3 primer (GGGATGRAGTCACAKACYCAGGTCTTYRTA; SEQ ID NO: 12) or 5'-Mm-LC-Leader4 primer (GGGAT-GAGGKCCCCWGCTCAGYTYCTKGGR; SEQ ID NO: 13) or 5'-Mm-LC-Leader5 primer (GGGATGAAGTTG-GCTGTTAGGCTGTTG; SEQ ID NO: 14) and 3'-Mm-Ckappa-R primer (CTAACACTCATTCCTGTTGAAGCTC; SEQ ID NO: 15) for the light chain, respectively. Amplified cDNAs were subcloned into pCR2.1 vector (Invitrogen). The sequences were analyzed using ABI3130XL. Full-length heavy chain and a 5'-truncated version of the L chain were obtained. To amplify the truncated region of L chain and identify precise leader sequences, 5'-rapid amplification of cDNA ends (5'-RACE) was performed. Double-stranded cDNA was prepared using a cDNA synthesis kit (TAKARA) and 5' adaptor (ad29S; ACATCACTC-CGT (SEQ ID NO: 16) and as29AS; ACGGAGTGATGTCCGTCGACG-TATCTCTGC-GTTGATACTTCAGCGTAGCT (SEQ ID NO: 17) were annealed) was added. cDNA was amplified with 5'-PCR1 primer (GTATCAACGCAGAGATACGTC-GACGG; SEQ ID NO: 18) for the first PCR and 5'-PCR4 primer (AGCTACGCTGAAGTATCAACGC-AG-AG; SEQ ID NO: 19) for the second PCR and 3' HC RACE primer_1 (GTACGGA-GTACTCCAAAAATGTTG; SEQ ID NO: 20) for the first PCR or 3' HC RACE primer_2 (TCTTCAGGCT-GCAGGCTGATGATC; SEQ ID NO: 21) for the second PCR for H chain, 3' LC RACE primer_3 (AAATCTTCAGGCT-GCAGGCTGTTG; SEQ ID NO: 22) for the first PCR or 3' LC RACE primer_4 (CTGTTGATCTTGAGAGAATAT-TGTG; SEQ ID NO: 23) for the second PCR for L chain, respectively. Amplified cDNAs were subcloned and sequenced as described above. The identified sequences of variable regions are as follows.

```
Nucleotide sequence of the heavy (H) chain
variable region:
                                      (SEQ ID NO: 24)
CAGGTCCAGCTGCAGCAGTCTGGACCTGAACTGGTGAAGCCTGGGGCTTC

AGTGAAGATGTCCTGCAAGGCTTCTGGCTACACCTTCACAAACTACTATA

TACACTGGGTGAAGCAGAGGCCTGGACAGGGACTTGAGTGGATTGGATGG

ATTTATCCTGGAGATGGTAGTCCTAAGTTCAATGAGAGGTTCAAGGGCAA

GACCACACTGACTGCAGACAAGTCCTCAAACACAGCCTACATGTTGCTCA
```

-continued

```
GCAGCCTGACCTCTGAAGACTCTGCGATCTATTTCTGTGCAACTGGGCCC

ACTGATGGCGACTACTTTGACTACTGGGGCCAGGGCACCACTCTCACAGT

CTCCTCA

Nucleotide sequence of the light (L) chain
variable region:
                                         (SEQ ID NO: 25)
GACATCCAGATGACTCAGTCTCCAGCCTCCCTATCTGCATCTGTGGGAGA

AACTGTCACCATCACATGTCGAGCAAGCGGGAATATTCACAATTTTTAG

CATGGTATCAGCAGAAACAGGGAAAATCTCCTCAGTTCCTGGTCTATAAT

GAAAAAACCTTAGCAGATGGTGTGCCATCAAGGTTCAGTGGCAGTGGATC

AGGAACACAATATTCTCTCAAGATCAACAGCCTGCAGCCTGAAGATTTTG

GGATTTATTTCTGTCAACAGTTTTGGAGTACTCCGTATACGTTCGGAGGG

GGGACCAAGCTGGAAATAAAA

Amino acid sequence of the heavy (H) chain
variable region:
                                         (SEQ ID NO: 26)
QVQLQQSGPELVKPGASVKMSCKASGYTFTNYYIHWVKQRPGQGLEWIGW

IYPGDGSPKFNERFKGKTTLTADKSSNTAYMLLSSLTSEDSAIYFCATGP

TDGDYFDYWGQGTTLTVSS

Amino acid sequence of the light (L) chain
variable region:
                                         (SEQ ID NO: 27)
DIQMTQSPASLSASVGETVTITCRASGNIHNFLAWYQQKQGKSPQFLVYN

EKTLADGVPSRFSGSGSGTQYSLKINSLQPEDFGIYFCQQFWSTPYTFGG

GTKLEIK
```

Example 4

Design of Humanized Anti-FKN mABs from Clone 3A5-2

Mouse anti-hFKN mAb, clone 3A5-2, was humanized by means of the complementarity determining region (CDR)-grafting method (Kontermann and Dübel, Antibody Engineering, Springer Lab Manual (2001) and Tsurushita et al., *Methods* 36:69-83 (2005)). The amino acid sequences of the CDRs are as follows.

```
CDR-H1:    NYYIH              (SEQ ID NO: 28)
CDR-H2:    WIYPGDGSPKFNERFKG  (SEQ ID NO: 29)
CDR-H3:    GPTDGDYFDY         (SEQ ID NO: 30)
CDR-L1:    RASGNIHNFLA        (SEQ ID NO: 31)
CDR-L2:    NEKTLAD            (SEQ ID NO: 32)
CDR-L3:    QQFWSTPYT          (SEQ ID NO: 33)
```

Human acceptor frameworks were selected among the human variable region segments. Identified CDRs of 3A5-2 were grafted into the selected human acceptor frameworks. The designed humanized sequences are as follows.

```
H chain (designated as H3; SEQ ID NO: 36)
QVQLVQSGAEVKKPGASVKVSCKASGYTFTNYYIHWVKQAPGQGLEWIGW

IYPGDGSPKFNERFKGRTTLTADKSTNTAYMLLSSLRSDDTAVYFCATGP

TDGDYFDYWGQGTTVTVSS

H chain (designated as H3-2; SEQ ID NO: 37)
QVQLVQSGAEVKKPGASVKVSCKASGYTFTNYYIHWVKQAPGQGLEWIGW

IYPGDGSPKFNERFKGRTTLTADKSTNTAYMLLSSLRSEDTAVYFCATGP

TDGDYFDYWGQGTTVTVSS

L chain (designated as L2; SEQ ID NO: 38)
DIQMTQSPSSLSASVGDRVTITCRASGNIHNFLAWYQQKPGKAPKFLVYN

EKTLADGVPSRFSGSGSGTQYTLTISSLQPEDFATYFCQQFWSTPYTFGG

GTKVEIK

H chain (designated as H4; SEQ ID NO: 39)
QVQLVQSGAEVKKPGASVKVSCKASGYTFTNYYIHWVRQAPGQGLEWIGW

IYPGDGSPKFNERFKGRTTLTRDKSTNTAYMELSSLRSDDTAVYFCATGP

TDGDYFDYWGQGTTVTVSS

Germline sequences for H chain (SEQ ID NO: 40)
QVQLVQSGAEVKKPGASVKVSCKASGYTFTXXXXXWVRQAPGQGLEWMGX

XXXXXXXXXXXXXXXXRVTMTRDTSTSTAYMELSSLRSEDTAVYYCARXX

XXXXXXXXWGQGTTVTVSS

Germline sequences for L chain (SEQ ID NO: 41)
DIQMTQSPSSLSASVGDRVTITCXXXXXXXXXXXWYQQKPGKAPKLLIYX

XXXXXXGVPSRFSGSGSGTDFTLTISSLQPEDFATYYCXXXXXXXXXFGG

GTKVEIK

H chain (designated as HK2; SEQ ID NO: 42)
QVQLVQSGAEVKKPGASVKVSCKASGYTFTNYYIHWVRQAPGQGLEWIGW

IYPGDGSPKFNERFKGRTTMTADTSTSTAYMELSSLRSEDTAVYFCARGP

TDGDYFDYWGQGTTVTVSS

H chain (designated as HK3; SEQ ID NO: 43)
QVQLVQSGAEVKKPGASVKVSCKASGYTFTNYYIHWVRQAPGQGLEWIGW

IYPGDGSPKFNERFKGRTTLTADKSTSTAYMELSSLRSEDTAVYFCARGP

TDGDYFDYWGQGTTVTVSS

L chain (designated as L4; SEQ ID NO: 44)
DIQMTQSPSSLSASVGDRVTITCRASGNIHNFLAWYQQKPGKAPKLLIYN

EKTLADGVPSRFSGSGSGTDYTLTISSLQPEDFATYFCQQFWSTPYTFGG

GTKVEIK

L chain (designated as L5; SEQ ID NO: 45)
DIQMTQSPSSLSASVGDRVTITCRASGNIHNFLAWYQQKPGKAPKLLIYN

EKTLADGVPSRFSGSGSGTQYTLTISSLQPEDFATYFCQQFWSTPYTFGG

GTKVEIK
```

Figure 4:
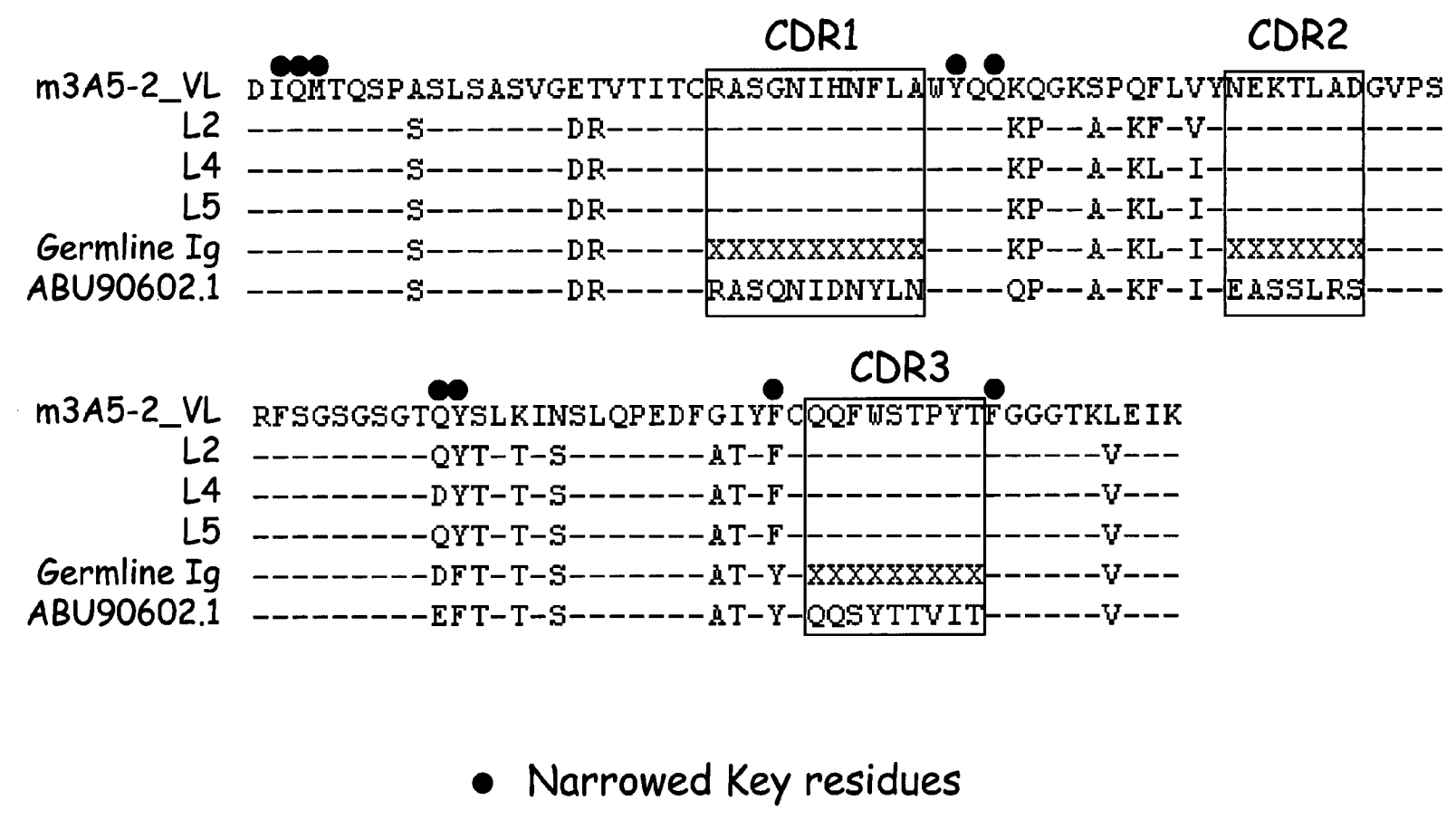

All humanized sequences were aligned (FIGS. 3 and 4).

Example 5

Construction of Expression Vectors of the Humanized Anti-HFKN mABs

To select the leader sequences for expression of humanized mAbs, germline segments were searched based on the similarity to AAA68427.1 and ABU90602.1. Segments VH1-1-18 and VKI-O12 were the most similar to the AAA68427.1 and ABU90602.1, respectively. Their leader sequences were used for expression of humanized mAbs. Their leader sequences are as follows.

```
H chain amino acid sequence (SEQ ID NO: 46)
MDWTWSILFLVAAPTGAHS

H chain nucleotide sequences
ATGGACTGGACCTGGAGCATCCTTTTCTTGGTGGCAGCACCAACAGGTGC

CCACTCC (for H3 and H3-2; SEQ ID NO: 47)

ATGGACTGGACATGGTCCATCCTGTTCCTGGTGGCCGCTCCAACTGGCGC

ACACTCT (for HK2 and HK3; SEQ ID NO: 48)

L chain amino acid sequence (SEQ ID NO: 49)
MDMRVPAQLLGLLLLWLRGARC

L chain nucleotide sequence (SEQ ID NO: 50)
ATGGACATGAGGGTCCCCGCTCAGCTCCTGGGGCTCCTGCTACTCTGGCT

CCGAGGTGCCAGATGT
```

Variable regions of the designed humanized anti-hFKN mAbs added with leader sequences described above were generated by PCR with the following primers.

```
For H3 heavy chain h3A5-2_VH3-1 primer (SEQ ID NO: 51):
ATGGACTGGACCTGGAGCATCCTTTTCTTGGTGGCAGCACCAACAGGTGC h3A5-2_VH3-2R primer (SEQ ID NO: 52):
CCAGACTGCACCAGCTGCACCTGGGAGTGGGCACCTGTTGGTGCTGCCAC h3A5-2_VH3-3 primer (SEQ ID NO: 53):
GTGCAGCTGGTGCAGTCTGGGGCTGAGGTGAAGAAGCCTGGGGCCTCAGT h3A5-2_VH3-4R primer (SEQ ID NO: 54):
GTGTATCCAGAAGCCTTGCAGGAGACCTTCACTGAGGCCCCAGGCTTCTT h3A5-2_VH3-5 primer (SEQ ID NO: 55):
TGCAAGGCTTCTGGATACACCTTCACCAACTACTATATACACTGGGTGAA h3A5-2_VH3-6R primer (SEQ ID NO: 56):
ATCCACTCAAGCCCTTGTCCAGGGGCCTGCTTCACCCAGTGTATATAGTA h3A5-2_VH3-7 primer (SEQ ID NO: 57):
GGACAAGGGCTTGAGTGGATAGGATGGATTTATCCTGGAGATGGTAGTCC h3A5-2_VH3-8R primer (SEQ ID NO: 58):
GTCCTGCCCTTGAACCTCTCATTGAACTTAGGACTACCATCTCCAGGATA h3A5-2_VH3-9 primer (SEQ ID NO: 59):
GAGAGGTTCAAGGGCAGGACCACCCTGACCGCAGACAAGTCCACGAACAC h3A5-2_VH3-10R primer (SEQ ID NO: 60):
GATCTCAGGCTGCTCAGCAACATGTAGGCTGTGTTCGTGGACTTGTCTGC h3A5-2_VH3-11 primer (SEQ ID NO: 61):
TTGCTGAGCAGCCTGAGATCTGACGACACGGCCGTGTATTTCTGTGCGAC h3A5-2_VH3-12R primer (SEQ ID NO: 62):
TAGTCAAAGTAGTCGCCATCAGTGGGCCCTGTCGCACAGAAATACACGGC h3A5-2 VH3-13 primer (SEQ ID NO: 63):
GATGGCGACTACTTTGACTACTGGGGCCAAGGGACCACGGTCACCGTCTC h3A5-2_R primer (SEQ ID NO: 64):
GACCGATGGGCCCTTGGTGGAGGCTGAAGAGACGGTGACCGTGGTCCC For L2 light chain h3A5-2_VL2-1 primer (SEQ ID NO: 65):
GCCACCATGGACATGAGGGTCCCCGCTCAGCTCCTGGGGCTCCTGCTACT

CTGGCTCCGAGGTGCCAGAT h3A5-2_VL2-2R primer (SEQ ID NO: 66):
TCCTACAGATGCAGACAGGGAGGATGGAGACTGGGTCATCTGGATGTCAC

ATCTGGCACCTCGGAGCCAG h3A5-2_VL2-3 primer (SEQ ID NO: 67):
CCCTGTCTGCATCTGTAGGAGACAGAGTCACCATCACTTGCCGAGCAAGC

GGGAATATTCACAATTTTTT h3A5-2_VL2-4R primer (SEQ ID NO: 68):
GAACTTAGGGGCTTTCCCTGGTTTCTGTTGATACCATGCTAAAAAATTGT

GAATATTCCCGCTTGCTCGG h3A5-2_VL2-5 primer (SEQ ID NO: 69):
CAGGGAAAGCCCCTAAGTTCCTGGTCTATAATGAAAAAACCTTAGCAGAT

GGGGTCCCATCAAGGTTCAG h3A5-2_VL2-6R primer (SEQ ID NO: 70):
GTTGCAGACTGCTGATGGTGAGAGTATATTGTGTCCCAGATCCACTGCCA

CTGAACCTTGATGGGACCCC h3A5-2_VL2-7 primer (SEQ ID NO: 71):
CACCATCAGCAGTCTGCAACCTGAAGATTTTGCGACCTACTTCTGTCAAC

AGTTTTGGAGTACTCCGTAT h3A5-2_VL2-8R primer (SEQ ID NO: 72):
TTTGATCTCCACCTTGGTCCCTCCGCCGAACGTATACGGAGTACTCCAAA

ACTGTTGACAGAA h3A5-2_VL-R (SEQ ID NO: 73):
GACAGATGGTGCAGCCACAGTTCGTTTGATCTCCACCTTGGTCCCTCC
```

Generated H3 and L2 were amplified by PCR with 5'-Eco-Sal-h3A5-2_VH_F primer (GCGAATTCGTCGACGC-CACCATGGACTGGACCTGGAGCATCCTTTT-CTTG; SEQ ID NO: 74) and 3'-NheI-h3A5-2_VH_R (CGCGCTAGCTGAAGAGAC-GGTGACCGTGGT-CCC; SEQ ID NO: 75) for H3 and 5'-h3A5-2_VL_SalI-kozac_F primer (GCGGTCGACGCCACCATGGACAT-GAGGGTCCCC; SEQ ID NO: 76) and 3'-h3A5-2_VL-R primer (GACAGATGGTGCAGCCACAGT-TCGTTTGATCTCCAC-CTTGGTCCCTCC; SEQ ID NO: 77) for L2, respectively.

H4 was generated by Genscript USA Inc. The sequence of H4 is as follows.

```
H4 (SEQ ID NO: 78):
GAATTCGTCGACGCCACCATGGACTGGACATGGTCCATCCTGTTCCTGGT

GGCCGCTCCAACTGGCGCACACTCTCAGGTGCAGCTGGTGCAGAGTGGCG

CTGAGGTGAAGAAACCCGGAGCATCAGTGAAGGTGTCCTGCAAAGCCAGC

GGATACACCTTCACCAACTACTATATTCATTGGGTGAGGCAGGCTCCTGG

ACAGGGACTGGAGTGGATCGGATGGATCTACCCAGGGGACGGTTCCCCTA

AGTTCAACGAAAGGTTTAAAGGCCGGACCACACTGACCAGGGATAAGTCA

ACCAATACAGCTTACATGGAACTGTCCAGCCTGCGCTCTGACGATACAGC

AGTGTATTTCTGTGCCACTGGGCCAACCGACGGCGACTACTTTGATTATT

GGGGCCAGGGAACTACCGTGACCGTGTCTAGTGCTAGC
```

The variable region of HK2 was generated by point mutations with PCR from H4 with the following primers.

```
3A5-2_HKG2_sa124F primer (SEQ ID NO: 79):
CGCGTCGACGCCACCATGGACTGGACATGGTCCATCCTG h3A5-2_HKG2_280F primer (SEQ ID NO: 80):
ATGACCGCCGATACCTCAACCTCCACAGCTTACATGAA h3A5-2_HKG2_300R primer (SEQ ID NO: 81):
GGTTGAGGTATCGGCGGTCATTGTGGTCCG h3A5-2_HKG2_340F primer (SEQ ID NO: 82):
GAGGATACAGCAGTGTATTTCTGTGCCCGGGGGCCAACC h3A5-2_HKG2_370R primer (SEQ ID NO: 83):
GGCACAGAAATACACTGCTGTATCCTCAGAGCGCAG h3A5-2_HKG2_Nhe24R (SEQ ID NO: 84):
CGCGCTAGCACTAGACACGGTCACGGTAGTTCC
```

The variable region of HK3 was generated by point mutations with PCR from HK2 with primers as follows.

```
h3A5-2_HKG2_sa124F primer (SEQ ID NO: 85):
CGCGTCGACGCCACCATGGACTGGACATGGTCCATCCTG HKG3_R primer (SEQ ID NO: 86):
TTGACTTATCGGCGGTCAGTGTGGTCCGGCCTTTAAACCTTTC HKG3_F primer (SEQ ID NO: 87):
ACACTGACCGCCGATAAGTCAACCTCCACAGCTTACATGGAA h3A5-2_HKG2_Nhe24R primer (SEQ ID NO: 88):
CGCGCTAGCACTAGACACGGTCACGGTAGTTCC
```

The variable region of L4 was generated by point mutations with PCR from L2 with primers as follows.

```
h3A5-2_VL4_sa124F primer (SEQ ID NO: 89):
CGCGTCGACGCCACCATGGACATGAGGGTCCCCGCTCAG h3A5-2_VL4_200R primer (SEQ ID NO: 90):
CAGCAGCTTAGGGGCTTTCCCTGGTTTCTG h3A5-2_VL4_190F primer (SEQ ID NO: 91):
GGGAAAGCCCCTAAGCTGCTGATCTATAATGAAAAA h3A5-2_VL4_260R primer (SEQ ID NO: 92):
TGTCCCAGATCCACTGCCACTGAACCTTGA h3A5-2_VL4_250F primer (SEQ ID NO: 93):
AGTGGCAGTGGATCTGGGACAGACTATACTCTCACC h3A5-2_VL4_BsiW24R primer (SEQ ID NO: 94):
CGCCGTACGTTTGATCTCCACCTTGGTCCCTCC
```

The variable region of L5 was generated by point mutations with PCR from L4 with primers as follows.

```
h3A5-2_VL4_sa124F primer (SEQ ID NO: 95):
CGCGTCGACGCCACCATGGACATGAGGGTCCCCGCTCAG VL5_R primer (SEQ ID NO: 96):
GGTGAGAGTATACTGTGTCCCAGATCCACTGCCACTGAAC VL5_F primer (SEQ ID NO: 97):
GGATCTGGGACACAGTATACTCTCACCATCAGCAGTCTG h3A5-2_VL4_BsiW24R (SEQ ID NO: 98):
cgcCGTACGTTTGATCTCCACCTTGGTCCCTCC
```

Constant regions of IgG2 and Igκ were amplified with 5'-NheI-IgG2_F primer (CGCGCTAGCACCAAGGGC-CCATCGGTCTTCCCC; SEQ ID NO: 99) and 3'-EcoRV-IgG2_R primer (CGCGATATCTCATTTACCCGGAGA-CAGGGAGAG; SEQ ID NO: 100) for IgG2 and 5'-BsiWI-Igκ_F primer (CGCCGTACGGTGGCTGCACCA-TCTGTCTTCATC; SEQ ID NO: 101) and 3'-EcoRV-Igκ_R primer (CGCGATATCCT-AACACTCTCCCCTGT-TGAAGCT; SEQ ID NO: 102) for Igκ, respectively. Amplified constant regions were subcloned into pENTR1A dNotI in which NotI was deleted.

Generated variable regions were subcloned into pENTR1A-IgG2 or pENTR1A-Igκby using SalI-NheI sites for heavy chains or SalI-BsiWI sites for light chains, respectively. In the case of L2, the constant region of Igκ was amplified with 5'-hIGK_F primer (CGAACTGTGGCTG-CACCATCTGTC; SEQ ID NO: 103) and 3'-hIGK_NotI-R primer (CGCGCGGCCGCCTAACACTCTCCCCTGT-TGAAGCTCTT; SEQ ID NO: 104). The amplified Igκ constant region and the generated L2 were combined by PCR and subcloned into pENTR1A. Subcloned variable regions and constant regions were transferred into pEE6.4 or pEE12.4 (Lonza) for the heavy chain and light chain, respectively, by using the GATEWAY system (Invitrogen).

H3-2 was generated by point mutation with the GeneTailor Site-Directed Mutagenesis System from pENTR1A-H3-IgG2 with 5'-h3A5-2_H3-2_300F primer (TTGCTGAG-CAGCCTGAGATCTGAGGACACGGCC; SEQ ID NO: 105) and 3'-h3A5-2_H3-2_320R primer (AGATCTCAG-GCTGCTCAGCAACATGTAGGC; SEQ ID NO: 106). GeneTailor Site-Directed Mutagenesis was performed according to according to the manufacturers' instructions. Mutated variable region and constant region were transferred into pEE6.4 as described above.

Example 6

Preparation of Humanized Anti-hFKN mAbs

Expression vectors of heavy and light chains of humanized anti-hFKN mAbs were transfected into HEK293E cells. On the day of transfection, HEK293E cells were inoculated with DMEM (Invitrogen) with 10% fetal bovine serum. After incubating for 5 hours, a mixture of heavy and light chain expression vectors was transfected with Lipofectamine 2000 (Invitrogen) according to the manufacturers' instructions. On the next day of the transfection, the medium was changed to 293 Serum-Free Media (SFM) II (Invitrogen). After incubating for 5 days at 37° C., culture supernatants were harvested. For BIACORE® assays, harvested supernatants were used directly. For chemotaxis assays, supernatants were purified with a recombinant protein A Sepharose column (Pharmacia).

Example 7

Preparation of Mouse-Human Chimeric 3A5-2 mAb

The variable region of heavy chain of mouse 3A5-2 was amplified with 5'-EcoRI-SalI-3A5-2 VH primer (GCG-GAATTCGTCGACGCCACCATGCGATGGAGCTGGA-TC; SEQ ID NO: 107) and 3'-IgG overlapped 3A5-2 VH primer (GACCGATGGGCC-CTTGGTGGAGGCTGAG-GAGACTGTGAGAGTGGTGCC; SEQ ID NO: 108). Human IgG2 constant region was amplified with 5'-hIgG2 primer (GCCTCCACCA-AGGGCCCATCGGTCTTC-CCCTGGCGCCCTG; SEQ ID NO: 109) and 3'-NotI-hIgG2 (CGCGCGGCCGCTCATTTACCCGGAGA-CAGGGAGAG; SEQ ID NO: 110). Amplified 3A5-2 VH and human IgG2 constant region were combined with PCR and subcloned into pCX-IRES-bsr, which has the blasticidin resistant gene for cell selection. The variable region of light chain of mouse 3A5-2 was amplified with 5'-3A_VL-SalI-kozac_F primer (GCGGTCGACGCCACCATGAGTGT- GCTCACTCAG; SEQ ID NO: 111) and 3'-3A-IgG1, 2_VH-R primer (GACAGATGGTGCAGCCACAGTTCGTTTT ATTTC-CAGCTTGGTCCCCCCT; SEQ ID NO: 112). Human Igκ constant region was amplified with 5'-hIGK_F primer (CGAACTGTGGCTGCACCATCTGTC; SEQ ID NO: 113) and 3'-hIGK_NotI-R (CGCGCGGCCGCCTAACACTCTC-CCCTGTTGA-AGCTCTT; SEQ ID NO: 114). Amplified 3A5-2 VH and human IgG2 constant region were combined with PCR and subcloned into pMX-IRES-puro, which has the puromycin resistant gene for cell selection.

The expression vector of chimeric light chain was transfected into HEK293E cells with pE-Eco and pGp (TAKARA) for retrovirus packaging. HEK293E cells were inoculated with DMEM (Invitrogen) with 10% FBS on the day before transfection. On the day of transfection, vectors were transfected with TranIT LT1 (TAKARA). After incubating for 3 days, culture supernatant containing retrovirus was harvested and added to B300.19 cells. After incubating for 8 hours, culture supernatant was removed and RPMI1640 (Invitrogen) with 10% FBS was added. After culturing for 2 days, puromycin was added to select infected cells. Selected cells were subsequently infected with another recombinant retrovirus carrying chimeric heavy chain, which was made using a similar method as described for the light chain. After selection with blasticidin, double-selected cells were cultured with SF-0 (Sanko Junyaku) containing 8 mM Glutamax, 55 μM 2-mercaptoethanol, 1× cholesterol (Invitrogen) in the Integra CELLine (Integra Bioscience). Culture supernatant was purified using a recombinant protein A Sepharose column (Pharmacia) for the chemotaxis assay and BIACORE® assay.

Example 8

Analysis of Humanized Anti-hFKN mAbs

Humanized anti-hFKN mAbs were analyzed using a chemotaxis assay for measuring neutralizing activity and a BIACORE® assay for measuring binding affinity to hFKN and cynomolgus monkey FKN. Representative data and results from three independent chemotaxis assays are summarized in FIG. 5 and shown in FIGS. 6A-B, 7A-D, and 8A-F. All combinations of H3 and H3-2 for heavy chain with L2 and L4 for light chain were successfully humanized as these mAbs showed similar neutralizing activity with the chimeric mAb. However, HK2, which was made by using narrowed key residues, showed decreased neutralizing activity in combination with L2 or L4. The results of the BIACORE® assay are summarized in FIGS. 9 and 10A-C. All combinations of H3 and H3-2 for heavy chain with L2 and L4 for light chain showed similar levels of affinity compared to the chimeric mAb. On the other hand, HK2L4 showed lower affinity than the others. These results suggest that 3A5-2 could not be humanized successfully by a general method using the usual key residue identification, especially in the case of the heavy chain.

Chemotaxis assays were performed as follows. Cells were placed in the upper wells of a transwell culture plate (Multi-Screen-MIC Plate, 5.0 μm, Millipore, Catalog No. MAMIC 5S10) with ligand in the lower wells. First, recombinant human FKN (R&D Systems, Catalog No. 362-CX/CF) (10 ng/ml final concentration) was added with purified antibodies at various concentrations (0 to 10 μg/ml) to the lower wells. The composition contained the following components: 3× chemokine solution, 50 μl/well; 1.5× purified mAb, 100 μl/well; chemokine and purified antibodies were diluted with 1×chemotaxis buffer (described above). B300.19 cells transfected with CX3CR1 ($2\times10^5$ cells/75 μl) were applied together with purified antibodies at various concentrations (0 to 10 μg/ml) to the upper wells. The composition contained the following components: 3×cell suspension, 25 μl/well; 1.5× purified mAb solution, 50 μl/well; cells and purified antibodies were diluted with 1× chemotaxis buffer. The chemotaxis assay was performed in a 5%-$CO_2$ incubator at 37° C. for 4 hours. After the incubation, 150 μl of the lower wells were harvested, fixed with 50 μl of 4% PFA/PBS, and 30 μl of the samples were applied to the FACSCantoII cell analyzer to count migrated cells.

The BIACORE® assays were performed as described above. However, for humanized and chimeric mAbs, anti-human IgG mouse mAb (GE Healthcare) was used as the capturing antibody on the sensor chip.

Example 9

Epitope Mapping Using Synthetic Peptides from FKN Chemokine Domain

Epitope mapping using libraries of overlapping synthetic peptides from FKN chemokine domain was performed. The twenty-one kinds of 15 residue peptides were synthesized by Sigma Genosys. The peptides were dissolved to 10 mg/ml with DMSO. These peptides (50 μg/ml) were coated on an ELISA plate (Nunc) overnight at 4° C. The peptide solutions were removed and PBS solution containing 1% BlockAce (Dainippon Pharma) was added to each well, incubated for 1 hour at room temperature, and washed with Tris-buffered saline (pH 7.4) containing 0.05% Tween 20 (washing solution). H3-2L4 antibody solution (50 μg/ml) was added to the wells and incubated for 2 hours at room temperature. The antibody solution was removed and washed with washing solution. Peroxidase-labeled anti-human IgG antibody solution (Zymed; 400 ng/ml) was added to the wells and incubated for 1 hour at room temperature. The antibody solution was removed and washed with washing solution. TMBZ solution (Sigma) was added to each well and incubated for 10 minutes at room temperature. The reaction was terminated with 1N $H_2SO_4$ solution and absorbance at 450-650 nm was measured.

Figure 11:
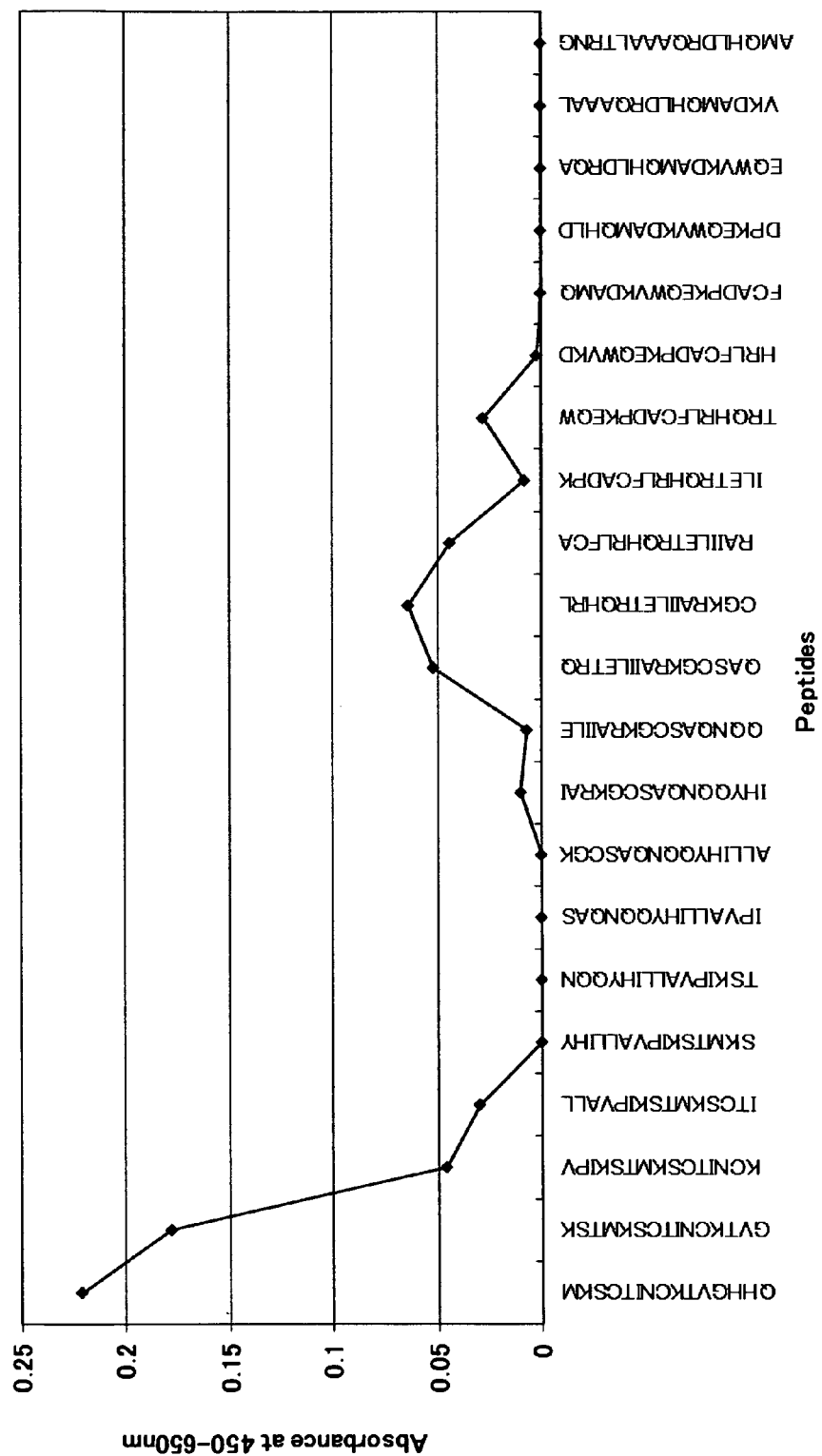
FIG. 11 depicts the results of epitope mapping using libraries of overlapping synthetic peptides (SEQ ID NOS 115-135, respectively, in order of appearance) from the FKN chemokine domain.

The results are shown in FIG. 11. H3-2L4 antibody reacted with peptides from the N-terminal and middle region of human FKN.

Example 10

Preparation of Alanine or Serine Substitution Mutants

Alanine or serine substitution mutants of hFKN-SEAP were prepared as follows. cDNA encoding the extracellular region of hFKN was isolated from the expression vector of hFKN-SEAP, pcDNA3.1 (+) hFKN-SEAP, by using SalI/NotI restriction enzymes and subcloned into pENTR1A_dSEAP-(His)10 vector containing SEAP cDNA (pENTR1A was purchased from Invitrogen). Alanine or serine substitution mutations were induced by using GeneTailor™ Site-Directed Mutagenesis System (Invitrogen) according to the manufacturer's instructions. The mutation-induced cDNA fragments of hFKN-SEAP were transferred into pcDNA3.1 (+)_cassette B vector (cassette B was purchased from Invitrogen) using the Gateway system (Invitrogen). The expression vectors of the alanine or serine substitution mutant of hFKN-SEAP were transfected into HEK293EBNA (HEK293E) cells (Invitrogen). HEK293E cells were inoculated with DMEM (Invitrogen) supplemented with 10% fetal bovine serum on the day before transfection. The expression vectors were transfected with TransIT LT1 (Takara) according to the manufacturer's instructions. After 3 of days incubation (5% $CO_2$ at 37° C.), the culture supernatant was harvested. The concentration of SEAP proteins was measured by using Great EscAPe SEAP Chemiluminescence Kit 2.0 (Clontech).

Example 11

ELISA for Epitope Mapping of hFKN

Figure 12:
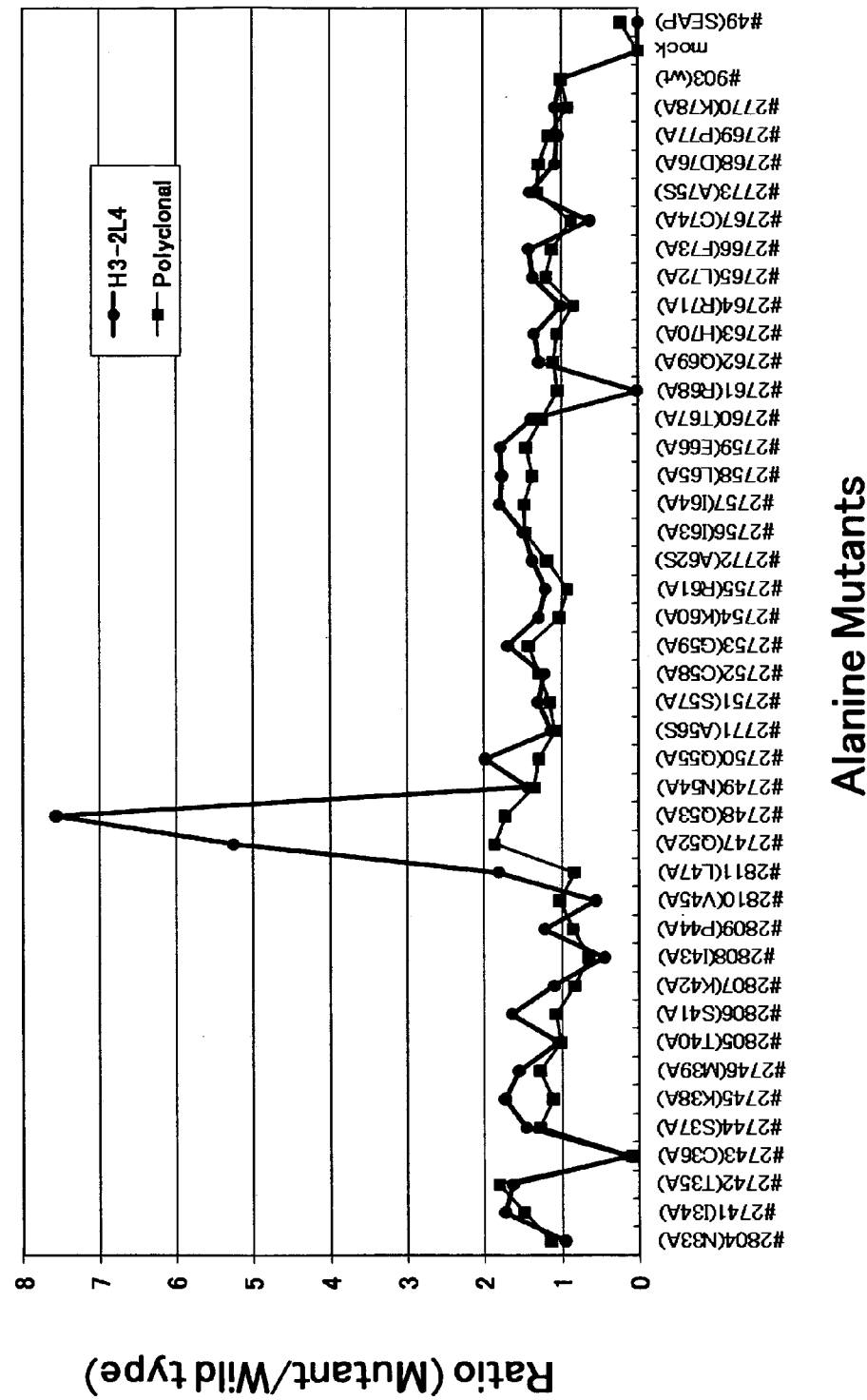
FIG. 12 depicts the results of epitope mapping of hFKN using ELISA.

Anti-hFKN polyclonal antibody (eBioscience) and H3-2L4 were each coated on wells of an ELISA plate (Nunc) overnight at 4° C. For each, the antibody solution was removed and PBS containing 1% bovine serum albumin was added to each well and incubated for 1 hour at room temperature, then washed with Tris-buffered saline (pH 7.4) containing 0.05% Tween20 (washing solution). Alanine or serine substitution mutants were diluted to 0.13 nM with PBS containing 1% BSA and 50 μl aliquots were added to the ELISA plate wells and incubated for 4 hours at room temperature. The mutant solutions were removed and washed with washing solution. p-Nitrophenyl phosphate solution (Thermo Scientific) was added to each well and incubated for 30 minutes at room temperature. The reaction was terminated with 1N NaOH solution and absorbance at 405 nm was measured. The results are shown in FIG. 12. R68A mutant specifically lost reactivity with H3-2L4. Other mutants that lost reactivity with H3-2L4 also lost reactivity with polyclonal antibody. These results show that R68 is a critical epitope for H3-2L4.

Example 12

Epitope Mapping of hFKN Using BIACORE®

Figure 13:
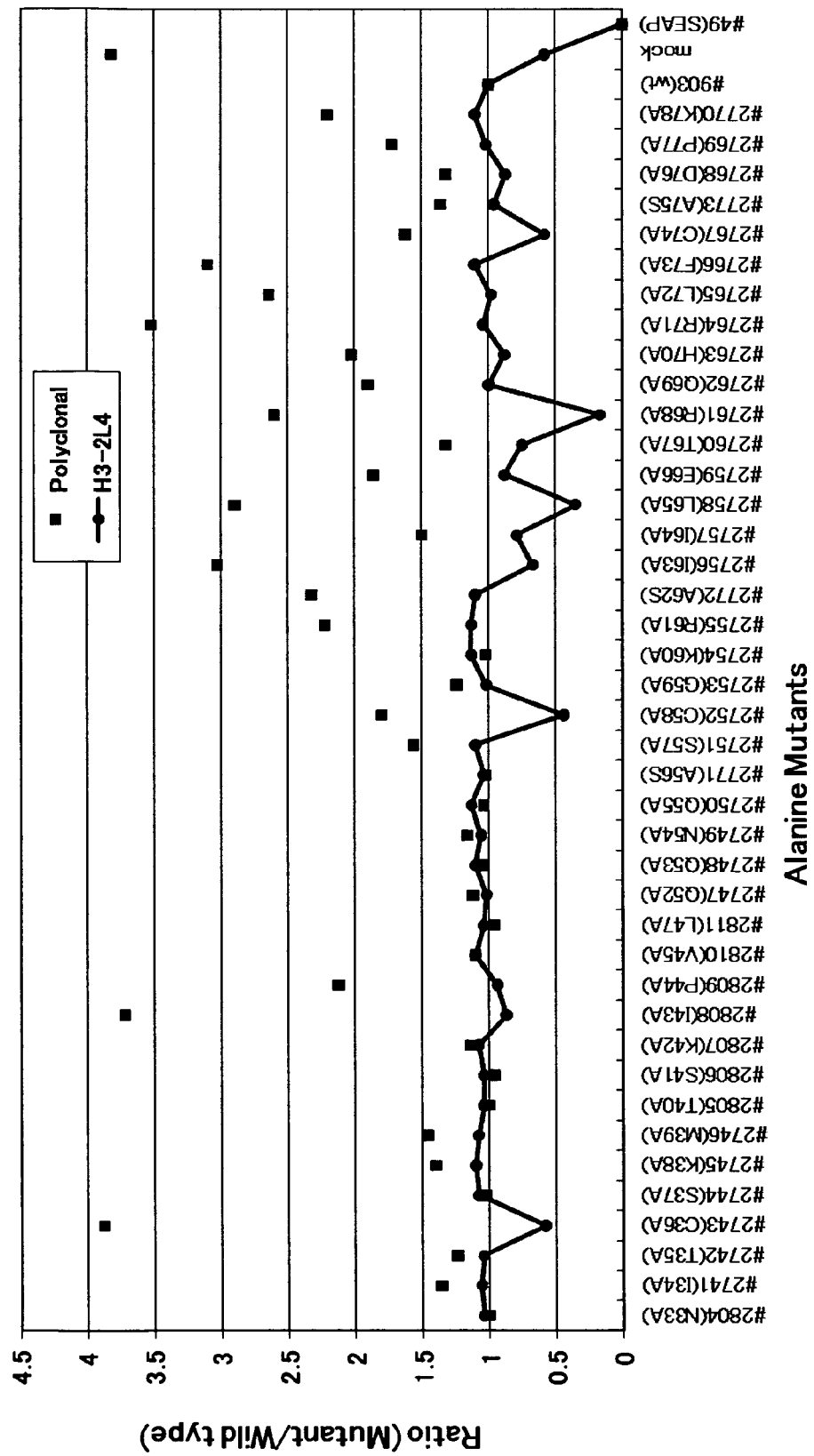
FIG. 13 depicts the results of epitope mapping of hFKN using BIACORE®.

Anti-histidine-tag antibody (Bethyl) was immobilized on a CM5 sensor chip (GE Healthcare). Alanine- or serine-substituted mutant solutions were 10 times diluted with HBS-EP buffer (GE Healthcare), loaded on the chip, washed with HBS-EP, and antigen binding level was measured. H3-2L4 and anti-FKN polyclonal antibody solution were loaded on the antigen bound chip, washed with HBS-EP, and antibody binding level was measured. [Antibody binding level/Antigen binding level] was calculated and the values calculated for each mutant were compared with that of wild type. The results are shown in FIG. 13.

Example 13

Reactivity of Other Antibodies with the R68A Mutant

Mouse anti-human FKN monoclonal antibodies (1F3, 1G1, 2B2, 3D5, 6D1, 7F6) and H3-2L4 antibody were coated on an ELISA plate (Nunc) overnight at 4° C. The antibody solutions were removed. PBS solution containing 1% BSA was added to each well and incubated for 1 hour at room temperature, and the wells were washed with Tris-buffered saline (pH 7.4) containing 0.05% Tween 20. The wild type and R68A mutated FKN-SEAP-His solution (1, 0.5, 0.25, 0.125 nM) were added to the wells and incubated for 2 hours at room temperature. The antigen solutions were removed and washed with washing solution. p-Nitrophenyl phosphate solution (Thermo Scientific) was added to each well and incubated for 30 minutes at room temperature. The reaction was terminated with 1N NaOH solution and absorbance at 405 nm was measured.

Neutralizing activity of these antibodies was tested based on a chemotaxis assay, as described above. 10 nM human FKN and various concentrations of these antibodies were added in the lower wells of a transwell plate. In the upper well of the plate, CX3CR1-expressing cells were added. After being incubated for 4 hours at 37° C., media of the lower wells were recovered and cells were fixed using a 4% formaldehyde solution. The number of cells was counted using a FACS analyzer. The relationship between neutralizing activity and reactivity with R68A mutant is shown in Table 1. Antibodies which strongly neutralize CTX activity lost their reactivity with the R68A mutant. This result shows that R68 of human FKN is the key recognition site for antibodies that can effectively neutralize the FKN function.

TABLE 1

Relationship between binding to R68A mutant and neutralizing activity

| Antibody | R68A/wild type (%) | CTX (IC50, nM) |
|---|---|---|
| 1F3 | 131 | 12.7 |
| 1G1 | 39 | 80< |
| 2B2 | 51 | 80< |
| 3D5 | 0 | 4.09 |
| 3H7 | 0 | 19.1 |
| 6D1 | 58 | 80< |
| 7F6 | 56 | 80< |
| H3-2L4 | 0 | 0.2 |

Example 14

Epitope Mapping of hFKN by NMR

Purification of Fab from H3-2L4 Antibody 100 mg of purified H3-2L4 antibody solution (20 mg/ml of PBS solution) was dialyzed against 0.1 M phosphate buffer (pH 7.0) containing 2 mM EDTA. The antibody concentration was adjusted to 15 mg/ml with the dialysis buffer and 30 mM cysteine was added. 0.2 mg of papain (Sigma) was added to the antibody solution and incubated for 14 hours at 37° C. Iodoacetamide was added to the solution to terminate the enzyme reaction. The papain digested antibody solution was dialyzed against PBS solution overnight at room temperature. The solution was applied to a ProSep vA (Millipore) column and the flow-through fraction was collected. The flow-through fraction was applied to an anti-human IgG Fc antibody (Jackson ImmunoResearch Laboratories) immobilized column and flow-through was collected. The flow-through fraction was concentrated and applied to Superose 12 10/300 GL (GE Healthcare) and fractions containing Fab fragment were collected. Purity of these fractions was analyzed by SDS PAGE and Fab dominant fractions were pooled.

Identification of Fab Binding Site on Fractalkine

In order to identify the binding site of the Fab on fractalkine, stable isotope-labeled ($^2H$, $^{15}N$ and $^2H$, $^{13}C$, $^{15}N$) fractalkine was prepared (Mizoue, L et al., Biochemistry, 38: 1402-1414 (1999)) and a $^{15}N$-Heteronuclear Single Quantum Coherence (HSQC) based NMR experiment was executed. NMR samples were prepared in 20 mM acetate buffer (pH 5.0) and 80% $D_2O$ (cross saturation experiment) or 5% $D_2O$ (the other experiments). All NMR experiments were carried out on a 700 MHz Bruker Avance spectrometer equipped with cryogenic probe under the temperature of 45° C.

Addition of the unlabeled Fab induced spectral change of fractalkine, indicating the interaction between the labeled fractalkine and the Fab. Sequential assignments of backbone $^{15}$N and $^1$H$_N$ of fractalkine complexed with the Fab were completed from 3D HNCA spectrum.

Figure 14:
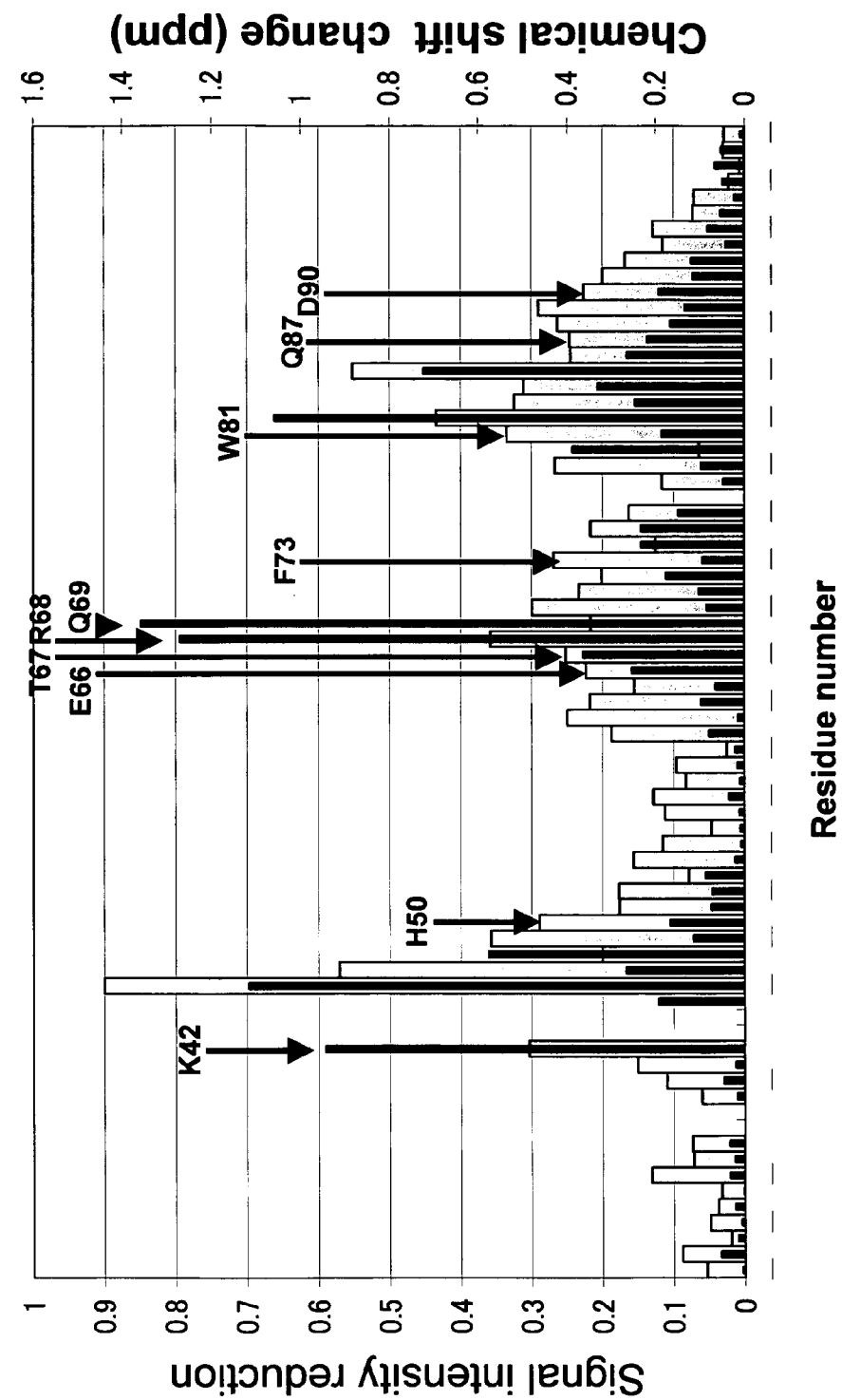
FIG. 14 shows the results of the cross saturation experiment to identify the Fab binding site on fractalkine. The plot shows that the E66-Q69, W81-Q87, H70-F73 and H88-D90 regions of FKN are included in the minimal interface with Fab.

A cross saturation experiment is one of the most precise NMR methods to determine binding interfaces of protein-protein interactions (Takahashi, H et al., Nat. Struct. Mol. Biol., 7: 220-223 (2000)). As a result of the experiment, signal intensity of several residues was reduced by selective irradiation of the Fab (FIG. 14). Those residues were located at two separate contiguous regions. The one region consists of E66-Q69, and the other region consists of W81-Q87. Furthermore, the chemical shifts of these residues were largely affected upon addition of the Fab, supporting the cross saturation data (FIG. 14). From these results, we concluded that these regions are included in the interface with the Fab.

Other Embodiments

From the foregoing description, it is apparent that variations and modifications may be made to the invention described herein to adopt it to various usages and conditions. Such embodiments are also within the scope of the following claims.

All publications mentioned in this specification are herein incorporated by reference to the same extent as if each independent publication or patent application was specifically and individually indicated to be incorporated by reference.

---

The invention claimed is:

1. An isolated anti-fractalkine antibody or fractalkine-binding fragment thereof, wherein the antibody or fragment thereof comprises:
   (a) a CDR-H1 consisting of the amino acid sequence of SEQ ID NO: 28;
   (b) a CDR-H2 consisting of the amino acid sequence of SEQ ID NO: 29;
   (c) a CDR-H3 consisting of the amino acid sequence of SEQ ID NO: 30;
   (d) a CDR-L1 consisting of the amino acid sequence of SEQ ID NO: 31;
   (e) a CDR-L2 consisting of the amino acid sequence of SEQ ID NO: 32; and
   (f) a CDR-L3 consisting of the amino acid sequence of SEQ ID NO: 33.

2. The isolated antibody of claim 1, wherein the antibody is an intact antibody.

3. The isolated antibody or fractalkine-binding fragment thereof of claim 1, wherein the antibody or fractalkine-binding fragment is humanized.

4. The isolated antibody or fractalkine-binding fragment thereof of claim 3, wherein the antibody comprises a heavy chain and a light chain, wherein the heavy chain variable domain of said antibody or fractalkine-binding fragment comprises the amino acid sequence of SEQ ID NO: 36, SEQ ID NO: 37, SEQ ID NO: 39, SEQ ID NO: 42, or SEQ ID NO: 43, and wherein the light chain variable domain of said antibody or fractalkine-binding fragment comprises the amino acid sequence of SEQ ID NO: 38, SEQ ID NO: 44, or SEQ ID NO: 45.

5. The isolated antibody or fractalkine-binding fragment thereof of claim 1, wherein the antibody or fractalkine-binding fragment is chimeric.

6. The isolated antibody or fractalkine-binding fragment thereof of claim 5, wherein the antibody comprises a heavy chain and a light chain, wherein the heavy chain variable domain of said antibody comprises the amino acid sequence of SEQ ID NO: 26, and wherein the light chain variable domain of said antibody comprises the amino acid sequence of SEQ ID NO: 27.

7. The isolated antibody or fractalkine-binding fragment thereof of claim 1 comprising a human constant region.

8. The isolated antibody or fractalkine-binding fragment thereof of claim 7, comprising a constant region of an IgG isotype.

9. The isolated antibody or fractalkine-binding fragment thereof of claim 8, comprising a constant region of the IgG2 isotype.

10. The isolated antibody or fractalkine-binding fragment thereof of claim 1, comprising a mutated Fc region such that said antibody has reduced antibody-dependent cell-mediated cytotoxicity (ADCC) and/or complement activation.

11. The isolated antibody or fractalkine-binding fragment thereof of claim 10, wherein the Fc region is mutated at one or more of V234, G237, C131, or C219.

12. The isolated antibody or fractalkine-binding fragment thereof of claim 1, wherein the fractalkine-binding fragment is selected from the group consisting of a Fab, a Fab', a F(ab')2, and a Fv, and wherein the fractalkine-binding fragment retains the binding specificity to fractalkine.

13. The isolated antibody or fractalkine-binding fragment thereof of claim 1, wherein the antibody inhibits the binding between fractalkine and CX3C chemokine receptor 1 (CX3CR1).

14. A pharmaceutical composition comprising the isolated antibody or fractalkine-binding fragment thereof of claim 1.

15. The pharmaceutical composition of claim 14, wherein the composition further comprises a carrier.

16. The pharmaceutical composition of claim 14, wherein the composition further comprises an additional therapeutic agent.

17. An isolated nucleic acid encoding the antibody or fractalkine-binding fragment thereof of claim 1.

18. The isolated nucleic acid of claim 17, wherein said nucleic acid encodes all or a portion of the heavy chain of said antibody or fractalkine-binding fragment thereof.

19. The isolated nucleic acid of claim 17, wherein said nucleic acid encodes all or a portion of the light chain of said antibody or fractalkine-binding fragment thereof.

20. A vector comprising the isolated nucleic acid of claim 17.

21. The vector of claim 20, wherein the vector is an expression vector.

22. A host cell comprising one or more vectors of claim 20.

23. The host cell of claim 22, wherein said host cell comprises a first and second vector, said first vector comprising a nucleic acid encoding a heavy chain and said second vector comprising a nucleic acid encoding a light chain of an anti-fractalkine antibody or fractalkine-binding fragment thereof that comprises:
   (a) a CDR-H1 consisting of the amino acid sequence of SEQ ID NO: 28;
   (b) a CDR-H2 consisting of the amino acid sequence of SEQ ID NO: 29;
   (c) a CDR-H3 consisting of the amino acid sequence of SEQ ID NO: 30;
   (d) a CDR-L1 consisting of the amino acid sequence of SEQ ID NO: 31;
   (e) a CDR-L2 consisting of the amino acid sequence of SEQ ID NO: 32; and
   (f) a CDR-L3 consisting of the amino acid sequence of SEQ ID NO: 33.

24. The host cell of claim 23, wherein expression of said heavy and light chain in said host cell produces an anti-fractalkine antibody or fractalkine-binding fragment thereof that comprises:
   (a) a CDR-H1 consisting of the amino acid sequence of SEQ ID NO: 28;
   (b) a CDR-H2 consisting of the amino acid sequence of SEQ ID NO: 29;
   (c) a CDR-H3 consisting of the amino acid sequence of SEQ ID NO: 30;
   (d) a CDR-L1 consisting of the amino acid sequence of SEQ ID NO: 31;
   (e) a CDR-L2 consisting of the amino acid sequence of SEQ ID NO: 32; and
   (f) a CDR-L3 consisting of the amino acid sequence of SEQ ID NO: 33.

25. The host cell of claim 22, wherein the host cell is prokaryotic.

26. The host cell of claim 22, wherein the host cell is eukaryotic.

27. The host cell of claim 26, wherein the host cell is mammalian.

28. The host cell of claim 27, wherein the cell is a CHO cell or NS0 cell.

29. A method for making an anti-fractalkine antibody or fractalkine-binding fragment thereof, said method comprising (a) expressing the vector of claim 20 in a suitable host cell, and (b) recovering the antibody or fractalkine-binding fragment thereof.

30. The method of claim 29, wherein said antibody or fractalkine-binding fragment thereof is secreted by said host cell into culture media.

31. The method of claim 30, wherein said antibody or fractalkine-binding fragment thereof is purified to at least 95% or greater with respect to said antibody-containing culture media.

32. A method for treating an inflammatory disorder selected from ulcerative colitis, Crohn's disease, and rheumatoid arthritis, the method comprising administering an effective amount of the antibody or fractalkine-binding fragment thereof of claim 1 to a subject in need of such treatment, whereby the inflammatory disorder is treated.

33. An isolated anti-fractalkine antibody or fractalkine-binding fragment thereof, wherein the antibody or fragment thereof comprises a heavy chain comprising the amino acid sequence of SEQ ID NO: 37 and a light chain comprising the amino acid sequence of SEQ ID NO: 44.

34. The isolated antibody of claim 33, wherein the antibody is an intact antibody.

35. The isolated antibody or fractalkine-binding fragment thereof of claim 33, wherein the antibody or fractalkine-binding fragment is humanized.

36. The isolated antibody or fractalkine-binding fragment thereof of claim 33, wherein the antibody or fractalkine-binding fragment is chimeric.

37. The isolated antibody or fractalkine-binding fragment thereof of claim 33 comprising a human constant region.

38. The isolated antibody or fractalkine-binding fragment thereof of claim 37, comprising a constant region of an IgG isotype.

39. The isolated antibody or fractalkine-binding fragment thereof of claim 38, comprising a constant region of the IgG2 isotype.

40. The isolated antibody or fractalkine-binding fragment thereof of claim 33, comprising a mutated Fc region such that said antibody has reduced antibody-dependent cell-mediated cytotoxicity (ADCC) and/or complement activation.

41. The isolated antibody or fractalkine-binding fragment thereof of claim 40, wherein the Fc region is mutated at one or more of V234, G237, C131, or C219.

42. The isolated antibody or fractalkine-binding fragment thereof of claim 33, wherein the fractalkine-binding fragment is selected from the group consisting of a Fab, a Fab', a F(ab')2, and a Fv, and wherein the fractalkine-binding fragment retains the binding specificity to fractalkine.

43. The isolated antibody or fractalkine-binding fragment thereof of claim 33, wherein the antibody inhibits the binding between fractalkine and CX3C chemokine receptor 1 (CX3CR1).

44. A pharmaceutical composition comprising the isolated antibody or fractalkine-binding fragment thereof of claim 33.

45. The pharmaceutical composition of claim 44, wherein the composition further comprises a carrier.

46. The pharmaceutical composition of claim 44, wherein the composition further comprises an additional therapeutic agent.

47. An isolated nucleic acid encoding the antibody or fractalkine-binding fragment thereof of claim 33.

48. The isolated nucleic acid of claim 47, wherein said nucleic acid encodes all or a portion of the heavy chain of said antibody or fractalkine-binding fragment thereof.

49. The isolated nucleic acid of claim 47, wherein said nucleic acid encodes all or a portion of the light chain of said antibody or fractalkine-binding fragment thereof.

50. A vector comprising the isolated nucleic acid of claim 47.

51. The vector of claim 50, wherein the vector is an expression vector.

52. A host cell comprising one or more vectors of claim 50.

53. The host cell of claim 52, wherein said host cell comprises a first and second vector, said first vector comprising a nucleic acid encoding a heavy chain and said second vector comprising a nucleic acid encoding a light chain of an anti-fractalkine antibody or fractalkine-binding fragment thereof that comprises:
   (a) a CDR-H1 consisting of the amino acid sequence of SEQ ID NO: 28;

(b) a CDR-H2 consisting of the amino acid sequence of SEQ ID NO: 29;
(c) a CDR-H3 consisting of the amino acid sequence of SEQ ID NO: 30;
(d) a CDR-L1 consisting of the amino acid sequence of SEQ ID NO: 31;
(e) a CDR-L2 consisting of the amino acid sequence of SEQ ID NO: 32; and
(f) a CDR-L3 consisting of the amino acid sequence of SEQ ID NO: 33.

54. The host cell of claim 23, wherein expression of said heavy and light chain in said host cell produces an anti-fractalkine antibody or fractalkine-binding fragment thereof that comprises:
(a) a CDR-H1 consisting of the amino acid sequence of SEQ ID NO: 28;
(b) a CDR-H2 consisting of the amino acid sequence of SEQ ID NO: 29;
(c) a CDR-H3 consisting of the amino acid sequence of SEQ ID NO: 30;
(d) a CDR-L1 consisting of the amino acid sequence of SEQ ID NO: 31;
(e) a CDR-L2 consisting of the amino acid sequence of SEQ ID NO: 32; and
(f) a CDR-L3 consisting of the amino acid sequence of SEQ ID NO: 33.

55. The host cell of claim 52, wherein the host cell is prokaryotic.

56. The host cell of claim 52, wherein the host cell is eukaryotic.

57. The host cell of claim 56, wherein the host cell is mammalian.

58. The host cell of claim 57, wherein the cell is a CHO cell or NS0 cell.

59. A method for making an anti-fractalkine antibody or fractalkine-binding fragment thereof, said method comprising (a) expressing the vector of claim 50 in a suitable host cell, and (b) recovering the antibody or fractalkine-binding fragment thereof.

60. The method of claim 59, wherein said antibody or fractalkine-binding fragment thereof is secreted by said host cell into culture media.

61. The method of claim 60, wherein said antibody or fractalkine-binding fragment thereof is purified to at least 95% or greater with respect to said antibody-containing culture media.

62. A method for treating an inflammatory disorder selected from ulcerative colitis, Crohn's disease, and rheumatoid arthritis, the method comprising administering an effective amount of the antibody or fractalkine-binding fragment thereof of claim 33 to a subject in need of such treatment, whereby the inflammatory disorder is treated.

* * * * *

SEQUENCE LISTING

```
<160> NUMBER OF SEQ ID NOS: 135

<210> SEQ ID NO 1
<211> LENGTH: 397
<212> TYPE: PRT
<213> ORGANISM: Homo sapiens

<400> SEQUENCE: 1

Met Ala Pro Ile Ser Leu Ser Trp Leu Leu Arg Leu Ala Thr Phe Cys
1               5                   10                  15

His Leu Thr Val Leu Leu Ala Gly Gln His His Gly Val Thr Lys Cys
            20                  25                  30

Asn Ile Thr Cys Ser Lys Met Thr Ser Lys Ile Pro Val Ala Leu Leu
        35                  40                  45

Ile His Tyr Gln Gln Asn Gln Ala Ser Cys Gly Lys Arg Ala Ile Ile
    50                  55                  60

Leu Glu Thr Arg Gln His Arg Leu Phe Cys Ala Asp Pro Lys Glu Gln
65                  70                  75                  80

Trp Val Lys Asp Ala Met Gln His Leu Asp Arg Gln Ala Ala Ala Leu
                85                  90                  95

Thr Arg Asn Gly Gly Thr Phe Glu Lys Gln Ile Gly Glu Val Lys Pro
            100                 105                 110

Arg Thr Thr Pro Ala Ala Gly Gly Met Asp Glu Ser Val Val Leu Glu
        115                 120                 125

Pro Glu Ala Thr Gly Glu Ser Ser Ser Leu Glu Pro Thr Pro Ser Ser
    130                 135                 140

Gln Glu Ala Gln Arg Ala Leu Gly Thr Ser Pro Glu Leu Pro Thr Gly
145                 150                 155                 160

Val Thr Gly Ser Ser Gly Thr Arg Leu Pro Pro Thr Pro Lys Ala Gln
                165                 170                 175

Asp Gly Gly Pro Val Gly Thr Glu Leu Phe Arg Val Pro Pro Val Ser
            180                 185                 190

Thr Ala Ala Thr Trp Gln Ser Ser Ala Pro His Gln Pro Gly Pro Ser
        195                 200                 205

Leu Trp Ala Glu Ala Lys Thr Ser Glu Ala Pro Ser Thr Gln Asp Pro
    210                 215                 220

Ser Thr Gln Ala Ser Thr Ala Ser Ser Pro Ala Pro Glu Glu Asn Ala
225                 230                 235                 240

Pro Ser Glu Gly Gln Arg Val Trp Gly Gln Gly Gln Ser Pro Arg Pro
                245                 250                 255

Glu Asn Ser Leu Glu Arg Glu Glu Met Gly Pro Val Pro Ala His Thr
            260                 265                 270
```

```
Asp Ala Phe Gln Asp Trp Gly Pro Gly Ser Met Ala His Val Ser Val
        275                 280                 285

Val Pro Val Ser Ser Glu Gly Thr Pro Ser Arg Glu Pro Val Ala Ser
    290                 295                 300

Gly Ser Trp Thr Pro Lys Ala Glu Glu Pro Ile His Ala Thr Met Asp
305                 310                 315                 320

Pro Gln Arg Leu Gly Val Leu Ile Thr Pro Val Pro Asp Ala Gln Ala
                325                 330                 335

Ala Thr Arg Arg Gln Ala Val Gly Leu Leu Ala Phe Leu Gly Leu Leu
            340                 345                 350

Phe Cys Leu Gly Val Ala Met Phe Thr Tyr Gln Ser Leu Gln Gly Cys
        355                 360                 365

Pro Arg Lys Met Ala Gly Glu Met Ala Glu Gly Leu Arg Tyr Ile Pro
    370                 375                 380

Arg Ser Cys Gly Ser Asn Ser Tyr Val Leu Val Pro Val
385                 390                 395

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cgcgtcgacg ccaccatggc tccgatatct ctgtc                            35

<210> SEQ ID NO 3
<211> LENGTH: 32
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
gcgggcggcc gccctccggg tggcagcctg gg                               32

<210> SEQ ID NO 4
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
gcgctcgagg ccaccatggc tccgatatct ctgtcgtgg                        39

<210> SEQ ID NO 5
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cgcggcggcc gcggtggcag cctgggagtc agggac                           36

<210> SEQ ID NO 6
```

<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
gggatggrat gsagctgkgt matsctctt                                    29

<210> SEQ ID NO 7
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gggatgract tcgggytgag ctkggtttt                                    29

<210> SEQ ID NO 8
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
gggatggctg tcttggggct gctcttct                                     28

<210> SEQ ID NO 9
<211> LENGTH: 34
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
tcatttaccc ggagtccggg agaagctctt agtc                              34

<210> SEQ ID NO 10
<211> LENGTH: 28
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
gggatggaga cagacacact cctgctat                                     28

<210> SEQ ID NO 11
<211> LENGTH: 29
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggatggatt ttcaggtgca gattttcag                                    29

<210> SEQ ID NO 12
<211> LENGTH: 30

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
gggatgragt cacakacyca ggtcttyrta                                      30

<210> SEQ ID NO 13
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
gggatgaggk ccccwgctca gytyctkggr                                      30

<210> SEQ ID NO 14
<211> LENGTH: 27
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gggatgaagt tggctgttag gctgttg                                         27

<210> SEQ ID NO 15
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
ctaacactca ttcctgttga agctc                                           25

<210> SEQ ID NO 16
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 16
acatcactcc gt                                                         12

<210> SEQ ID NO 17
<211> LENGTH: 50
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 17
acggagtgat gtccgtcgac gtatctctgc gttgatactt cagcgtagct                50

<210> SEQ ID NO 18
<211> LENGTH: 26
<212> TYPE: DNA
```

```
<213> ORGANISM: Artificial Sequence
<220> FEATURE:
<223> OTHER INFORMATION: Description of Artificial Sequence: Synthetic
      primer

<400> SEQUENCE: 18
gtatcaacgc agagatacgt cgacgg                                          26

<210> SEQ ID NO 19
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 19
agctacgctg aagtatcaac gcagag                                          26

<210> SEQ ID NO 20
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
gtacggagta ctccaaaaat gttg                                            24

<210> SEQ ID NO 21
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
tcttcaggct gcaggctgat gatc                                            24

<210> SEQ ID NO 22
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aaatcttcag gctgcaggct gttg                                            24

<210> SEQ ID NO 23
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
ctgttgatct tgagagaata ttgtg                                           25

<210> SEQ ID NO 24
<211> LENGTH: 357
<212> TYPE: DNA
<213> ORGANISM: Artificial Sequence
```

<220> FEATURE:
<223> OTHER INFORMATION: Description of Artificial Sequence: Synthetic
      polynucleotide

<400> SEQUENCE: 24
caggtccagc tgcagcagtc tggacctgaa ctggtgaagc ctggggcttc agtgaagatg    60
tcctgcaagg cttctggcta caccttcaca aactactata tacactgggt gaagcagagg   120
cctggacagg gacttgagtg gattggatgg atttatcctg gagatggtag tcctaagttc   180
aatgagaggt tcaagggcaa gaccacactg actgcagaca gtcctcaaa cacagcctac    240 atgttgctca gcagcctgac ctctgaagac tctgcgatct atttctgtgc aactgggccc   300
actgatggcg actactttga ctactggggc cagggcacca ctctcacagt ctcctca      357

<210> SEQ ID NO 25
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 25
gacatccaga tgactcagtc tccagcctcc ctatctgcat ctgtgggaga aactgtcacc    60
atcacatgtc gagcaagcgg gaatattcac aattttttag catggtatca gcagaaacag   120
ggaaaatctc ctcagttcct ggtctataat gaaaaaacct agcagatgg tgtgccatca    180 aggttcagtg gcagtggatc aggaacacaa tattctctca agatcaacag cctgcagcct   240
gaagattttg ggatttattt ctgtcaacag ttttggagta ctccgtatac gttcggaggg   300
gggaccaagc tggaaataaa a                                             321

<210> SEQ ID NO 26
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 26

Gln Val Gln Leu Gln Gln Ser Gly Pro Glu Leu Val Lys Pro Gly Ala
1               5                   10                  15

Ser Val Lys Met Ser Cys Lys Ala Ser Gly Tyr Thr Phe Thr Asn Tyr
            20                  25                  30

Tyr Ile His Trp Val Lys Gln Arg Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Lys Thr Thr Leu Thr Ala Asp Lys Ser Ser Asn Thr Ala Tyr
65                  70                  75                  80

Met Leu Leu Ser Ser Leu Thr Ser Glu Asp Ser Ala Ile Tyr Phe Cys
                85                  90                  95

Ala Thr Gly Pro Thr Asp Gly Asp Tyr Phe Asp Tyr Trp Gly Gln Gly
            100                 105                 110

Thr Thr Leu Thr Val Ser Ser
        115

<210> SEQ ID NO 27
<211> LENGTH: 107

```
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Gln Met Thr Gln Ser Pro Ala Ser Leu Ser Ala Ser Val Gly
1               5                   10                  15

Glu Thr Val Thr Ile Thr Cys Arg Ala Ser Gly Asn Ile His Asn Phe
            20                  25                  30

Leu Ala Trp Tyr Gln Gln Lys Gln Gly Lys Ser Pro Gln Phe Leu Val
        35                  40                  45

Tyr Asn Glu Lys Thr Leu Ala Asp Gly Val Pro Ser Arg Phe Ser Gly
    50                  55                  60

Ser Gly Ser Gly Thr Gln Tyr Ser Leu Lys Ile Asn Ser Leu Gln Pro
65                  70                  75                  80

Glu Asp Phe Gly Ile Tyr Phe Cys Gln Gln Phe Trp Ser Thr Pro Tyr
                85                  90                  95

Thr Phe Gly Gly Gly Thr Lys Leu Glu Ile Lys
            100                 105

<210> SEQ ID NO 28
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Asn Tyr Tyr Ile His
1               5

<210> SEQ ID NO 29
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Trp Ile Tyr Pro Gly Asp Gly Ser Pro Lys Phe Asn Glu Arg Phe Lys
1               5                   10                  15

Gly

<210> SEQ ID NO 30
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Gly Pro Thr Asp Gly Asp Tyr Phe Asp Tyr
1               5                   10

<210> SEQ ID NO 31
<211> LENGTH: 11
<212> TYPE: PRT
<213> ORGANISM: Artificial Sequence
<220> FEATURE:
```

<223> OTHER INFORMATION: Description of Artificial Sequence: Synthetic
      peptide

<400> SEQUENCE: 31

Arg Ala Ser Gly Asn Ile His Asn Phe Leu Ala
1               5                   10

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

Asn Glu Lys Thr Leu Ala Asp
1               5

<210> SEQ ID NO 33
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 33

Gln Gln Phe Trp Ser Thr Pro Tyr Thr
1               5

<210> SEQ ID NO 34
<211> LENGTH: 119
<212> TYPE: PRT
<213> ORGANISM: Homo sapiens

<400> SEQUENCE: 34

Gln Val Lys Leu Leu Glu Ser Gly Ala Glu Val Lys Lys Pro Gly Ala
1               5                   10                  15

Ser Val Lys Val Ser Cys Lys Ala Ser Gly Tyr Thr Phe Thr Gly His
                20                  25                  30

Tyr Met His Trp Val Arg Gln Ala Pro Gly Gln Gly Leu Glu Trp Ile
            35                  40                  45

Gly Trp Ile Ser Pro Asn Arg Gly Ala Thr Arg Phe Ala Gln Lys Phe
        50                  55                  60

Gln Gly Arg Val Thr Met Thr Ser Asp Thr Ser Ile Asn Thr Val Tyr
65                  70                  75                  80

Met Glu Leu Ser Gly Leu Arg Phe Asp Asp Thr Ala Val Tyr Tyr Cys
                85                  90                  95

Ala Thr Thr Arg Thr Ala Tyr Tyr Gly Met Asp Val Trp Gly Gln Gly
            100                 105                 110

Thr Thr Val Thr Val Ser Ser
        115

<210> SEQ ID NO 35
<211> LENGTH: 107
<212> TYPE: PRT
<213> ORGANISM: Homo sapiens

<400> SEQUENCE: 35

Asp Ile Gln Met Thr Gln Ser Pro Ser Ser Leu Ser Ala Ser Val Gly
1               5                   10                  15

```
Asp Arg Val Thr Ile Thr Cys Arg Ala Ser Gln Asn Ile Asp Asn Tyr
            20                  25                  30

Leu Asn Trp Tyr Gln Gln Pro Gly Lys Ala Pro Lys Phe Leu Ile
        35                  40                  45

Tyr Glu Ala Ser Ser Leu Arg Ser Gly Val Pro Ser Arg Phe Ser Gly
50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Gln Gln Ser Tyr Thr Thr Val Ile
                85                  90                  95

Thr Phe Gly Gly Gly Thr Lys Val Glu Ile Lys
            100                 105

<210> SEQ ID NO 36
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Lys Gln Ala Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Arg Thr Thr Leu Thr Ala Asp Lys Ser Thr Asn Thr Ala Tyr
65                  70                  75                  80

Met Leu Leu Ser Ser Leu Arg Ser Asp Asp Thr Ala Val Tyr Phe Cys
                85                  90                  95

Ala Thr Gly Pro Thr Asp Gly Asp Tyr Phe Asp Tyr Trp Gly Gln Gly
            100                 105                 110

Thr Thr Val Thr Val Ser Ser
        115

<210> SEQ ID NO 37
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Lys Gln Ala Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Arg Thr Thr Leu Thr Ala Asp Lys Ser Thr Asn Thr Ala Tyr
65                  70                  75                  80
```

```
Met Leu Leu Ser Ser Leu Arg Ser Glu Asp Thr Ala Val Tyr Phe Cys
             85                  90                  95

Ala Thr Gly Pro Thr Asp Gly Asp Tyr Phe Asp Tyr Trp Gly Gln Gly
            100                 105                 110

Thr Thr Val Thr Val Ser Ser
        115

<210> SEQ ID NO 38
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Phe
            20                  25                  30

Leu Ala Trp Tyr Gln Gln Lys Pro Gly Lys Ala Pro Lys Phe Leu Val
        35                  40                  45

Tyr Asn Glu Lys Thr Leu Ala Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Phe Cys Gln Gln Phe Trp Ser Thr Pro Tyr
                85                  90                  95

Thr Phe Gly Gly Gly Thr Lys Val Glu Ile Lys
            100                 105

<210> SEQ ID NO 39
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Arg Thr Thr Leu Thr Arg Asp Lys Ser Thr Asn Thr Ala Tyr
65                  70                  75                  80

Met Glu Leu Ser Ser Leu Arg Ser Asp Asp Thr Ala Val Tyr Phe Cys
                85                  90                  95

Ala Thr Gly Pro Thr Asp Gly Asp Tyr Phe Asp Tyr Trp Gly Gln Gly
            100                 105                 110

Thr Thr Val Thr Val Ser Ser
        115

<210> SEQ ID NO 40
<211> LENGTH: 119
```

```
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (31)..(35)
<223> OTHER INFORMATION: Any amino acid
<220> FEATURE:
<221> NAME/KEY: MOD_RES
<222> LOCATION: (50)..(66)
<223> OTHER INFORMATION: Any amino acid
<220> FEATURE:
<221> NAME/KEY: MOD_RES
<222> LOCATION: (99)..(108)
<223> OTHER INFORMATION: Any amino acid

<400> SEQUENCE: 40

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Xaa Xaa
            20                  25                  30

Xaa Xaa Xaa Trp Val Arg Gln Ala Pro Gly Gln Gly Leu Glu Trp Met
        35                  40                  45

Gly Xaa Xaa Xaa Xaa Xaa Xaa Xaa Xaa Xaa Xaa Xaa Xaa Xaa Xaa Xaa
    50                  55                  60

Xaa Xaa Arg Val Thr Met Thr Arg Asp Thr Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Xaa Xaa Xaa Xaa Xaa Xaa Xaa Xaa Xaa Trp Gly Gln Gly
            100                 105                 110

Thr Thr Val Thr Val Ser Ser
            115

<210> SEQ ID NO 41
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (24)..(34)
<223> OTHER INFORMATION: Any amino acid
<220> FEATURE:
<221> NAME/KEY: MOD_RES
<222> LOCATION: (50)..(56)
<223> OTHER INFORMATION: Any amino acid
<220> FEATURE:
<221> NAME/KEY: MOD_RES
<222> LOCATION: (89)..(97)
<223> OTHER INFORMATION: Any amino acid

<400> SEQUENCE: 41

Asp Ile Gln Met Thr Gln Ser Pro Ser Ser Leu Ser Ala Ser Val Gly
1               5                   10                  15

Asp Arg Val Thr Ile Thr Cys Xaa Xaa Xaa Xaa Xaa Xaa Xaa Xaa Xaa
            20                  25                  30

Xaa Xaa Trp Tyr Gln Gln Lys Pro Gly Lys Ala Pro Lys Leu Leu Ile
        35                  40                  45

Tyr Xaa Xaa Xaa Xaa Xaa Xaa Xaa Gly Val Pro Ser Arg Phe Ser Gly
    50                  55                  60
```

Ser Gly Ser Gly Thr Asp Phe Thr Leu Thr Ile Ser Ser Leu Gln Pro
65                  70                  75                  80

Glu Asp Phe Ala Thr Tyr Tyr Cys Xaa Xaa Xaa Xaa Xaa Xaa Xaa
                85                  90                  95

Xaa Phe Gly Gly Gly Thr Lys Val Glu Ile Lys
            100                 105

<210> SEQ ID NO 42
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 42

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Arg Thr Thr Met Thr Ala Asp Thr Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Pro Thr Asp Gly Asp Tyr Phe Asp Tyr Trp Gly Gln Gly
            100                 105                 110

Thr Thr Val Thr Val Ser Ser
        115

<210> SEQ ID NO 43
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Asn Tyr
            20                  25                  30

Tyr Ile His Trp Val Arg Gln Ala Pro Gly Gln Gly Leu Glu Trp Ile
        35                  40                  45

Gly Trp Ile Tyr Pro Gly Asp Gly Ser Pro Lys Phe Asn Glu Arg Phe
    50                  55                  60

Lys Gly Arg Thr Thr Leu Thr Ala Asp Lys Ser Thr Ser Thr Ala Tyr
65                  70                  75                  80

Met Glu Leu Ser Ser Leu Arg Ser Glu Asp Thr Ala Val Tyr Phe Cys
                85                  90                  95

Ala Arg Gly Pro Thr Asp Gly Asp Tyr Phe Asp Tyr Trp Gly Gln Gly
            100                 105                 110

Thr Thr Val Thr Val Ser Ser
        115

```
<210> SEQ ID NO 44
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Phe
            20                  25                  30

Leu Ala Trp Tyr Gln Gln Lys Pro Gly Lys Ala Pro Lys Leu Leu Ile
        35                  40                  45

Tyr Asn Glu Lys Thr Leu Ala Asp Gly Val Pro Ser Arg Phe Ser Gly
    50                  55                  60

Ser Gly Ser Gly Thr Asp Tyr Thr Leu Thr Ile Ser Ser Leu Gln Pro
65                  70                  75                  80

Glu Asp Phe Ala Thr Tyr Phe Cys Gln Gln Phe Trp Ser Thr Pro Tyr
                85                  90                  95

Thr Phe Gly Gly Gly Thr Lys Val Glu Ile Lys
            100                 105

<210> SEQ ID NO 45
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Arg Ala Ser Gly Asn Ile His Asn Phe
            20                  25                  30

Leu Ala Trp Tyr Gln Gln Lys Pro Gly Lys Ala Pro Lys Leu Leu Ile
        35                  40                  45

Tyr Asn Glu Lys Thr Leu Ala Asp Gly Val Pro Ser Arg Phe Ser Gly
    50                  55                  60

Ser Gly Ser Gly Thr Gln Tyr Thr Leu Thr Ile Ser Ser Leu Gln Pro
65                  70                  75                  80

Glu Asp Phe Ala Thr Tyr Phe Cys Gln Gln Phe Trp Ser Thr Pro Tyr
                85                  90                  95

Thr Phe Gly Gly Gly Thr Lys Val Glu Ile Lys
            100                 105

<210> SEQ ID NO 46
<211> LENGTH: 19
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Met Asp Trp Thr Trp Ser Ile Leu Phe Leu Val Ala Ala Pro Thr Gly
1               5                   10                  15

Ala His Ser
```

<210> SEQ ID NO 47
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 47
atggactgga cctggagcat cctttcttg gtggcagcac aacaggtgc ccactcc        57

<210> SEQ ID NO 48
<211> LENGTH: 57
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 48
atggactgga catggtccat cctgttcctg gtggccgctc caactggcgc acactct        57

<210> SEQ ID NO 49
<211> LENGTH: 22
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 49

Met Asp Met Arg Val Pro Ala Gln Leu Leu Gly Leu Leu Leu Leu Trp
1               5                   10                  15

Leu Arg Gly Ala Arg Cys
            20

<210> SEQ ID NO 50
<211> LENGTH: 66
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 50
atggacatga gggtccccgc tcagctcctg gggctcctgc tactctggct ccgaggtgcc        60
agatgt        66

<210> SEQ ID NO 51
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 51
atggactgga cctggagcat cctttcttg gtggcagcac aacaggtgc        50

<210> SEQ ID NO 52
<211> LENGTH: 50
<212> TYPE: DNA
<213> ORGANISM: Artificial Sequence
<220> FEATURE:
<223> OTHER INFORMATION: Description of Artificial Sequence: Synthetic -continued primer

<400> SEQUENCE: 52
ccagactgca ccagctgcac ctgggagtgg gcacctgttg gtgctgccac                50

<210> SEQ ID NO 53
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
gtgcagctgg tgcagtctgg ggctgaggtg aagaagcctg gggcctcagt                50

<210> SEQ ID NO 54
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
gtgtatccag aagccttgca ggagaccttc actgaggccc caggcttctt                50

<210> SEQ ID NO 55
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tgcaaggctt ctggatacac cttcaccaac tactatatac actgggtgaa                50

<210> SEQ ID NO 56
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
atccactcaa gcccttgtcc aggggcctgc ttcacccagt gtatatagta                50

<210> SEQ ID NO 57
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 57
ggacaagggc ttgagtggat aggatggatt tatcctggag atggtagtcc                50

<210> SEQ ID NO 58
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 58
gtcctgccct tgaacctctc attgaactta ggactaccat ctccaggata            50

<210> SEQ ID NO 59
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 59
gagaggttca agggcaggac caccctgacc gcagacaagt ccacgaacac            50

<210> SEQ ID NO 60
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 60
gatctcaggc tgctcagcaa catgtaggct gtgttcgtgg acttgtctgc            50

<210> SEQ ID NO 61
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 61
ttgctgagca gcctgagatc tgacgacacg gccgtgtatt tctgtgcgac            50

<210> SEQ ID NO 62
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 62
tagtcaaagt agtcgccatc agtgggccct gtcgcacaga aatacacggc            50

<210> SEQ ID NO 63
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 63
gatggcgact actttgacta ctggggccaa gggaccacgg tcaccgtctc            50

<210> SEQ ID NO 64
<211> LENGTH: 48
<212> TYPE: DNA
<213> ORGANISM: Artificial Sequence
<220> FEATURE:
<223> OTHER INFORMATION: Description of Artificial Sequence: Synthetic
      primer
```

```
<400> SEQUENCE: 64
gaccgatggg cccttggtgg aggctgaaga gacggtgacc gtggtccc              48

<210> SEQ ID NO 65
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 65
gccaccatgg acatgagggt ccccgctcag ctcctggggc tcctgctact ctggctccga   60
ggtgccagat                                                         70

<210> SEQ ID NO 66
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 66
tcctacagat gcagacaggg aggatggaga ctgggtcatc tggatgtcac atctggcacc   60
tcggagccag                                                         70

<210> SEQ ID NO 67
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 67
ccctgtctgc atctgtagga gacagagtca ccatcacttg ccgagcaagc gggaatattc   60
acaatttttt                                                         70

<210> SEQ ID NO 68
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 68
gaacttaggg gctttccctg gtttctgttg ataccatgct aaaaaattgt gaatattccc   60
gcttgctcgg                                                         70

<210> SEQ ID NO 69
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 69
cagggaaagc ccctaagttc ctggtctata atgaaaaaac cttagcagat ggggtcccat   60
caaggttcag                                                         70
```

<210> SEQ ID NO 70
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 70
gttgcagact gctgatggtg agagtatatt gtgtcccaga tccactgcca ctgaaccttg    60
atgggacccc                                                          70

<210> SEQ ID NO 71
<211> LENGTH: 70
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 71
caccatcagc agtctgcaac ctgaagattt tgcgacctac ttctgtcaac agttttggag    60
tactccgtat                                                          70

<210> SEQ ID NO 72
<211> LENGTH: 63
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 72
tttgatctcc accttggtcc ctccgccgaa cgtatacgga gtactccaaa actgttgaca    60
gaa                                                                 63

<210> SEQ ID NO 73
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 73
gacagatggt gcagccacag ttcgtttgat ctccaccttg gtccctcc                48

<210> SEQ ID NO 74
<211> LENGTH: 50
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 74
gcgaattcgt cgacgccacc atggactgga cctggagcat ccttttcttg              50

<210> SEQ ID NO 75
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 75
cgcgctagct gaagagacgg tgaccgtggt ccc          33

<210> SEQ ID NO 76
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 76
gcggtcgacg ccaccatgga catgagggtc ccc          33

<210> SEQ ID NO 77
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 77
gacagatggt gcagccacag ttcgtttgat ctccaccttg gtccctcc          48

<210> SEQ ID NO 78
<211> LENGTH: 438
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 78
gaattcgtcg acgccaccat ggactggaca tggtccatcc tgttcctggt ggccgctcca          60
actggcgcac actctcaggt gcagctggtg cagagtggcg ctgaggtgaa gaaacccgga         120
gcatcagtga aggtgtcctg caaagccagc ggatacacct tcaccaacta ctatattcat         180
tgggtgaggc aggctcctgg acagggactg gagtggatcg gatggatcta cccagggac         240
ggttcccta agttcaacga aaggtttaaa ggccggacca cactgaccag ggataagtca         300
accaatacag cttacatgga actgtccagc ctgcgctctg acgatacagc agtgtatttc         360
tgtgccactg ggccaaccga cggcgactac tttgattatt ggggccaggg aactaccgtg         420
accgtgtcta gtgctagc                                                      438

<210> SEQ ID NO 79
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 79
cgcgtcgacg ccaccatgga ctggacatgg tccatcctg          39

<210> SEQ ID NO 80
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 80
atgaccgccg atacctcaac ctccacagct tacatggaa                39

<210> SEQ ID NO 81
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 81
ggttgaggta tcggcggtca ttgtggtccg                30

<210> SEQ ID NO 82
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 82
gaggatacag cagtgtattt ctgtgcccgg gggccaacc                39

<210> SEQ ID NO 83
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 83
ggcacagaaa tacactgctg tatcctcaga gcgcag                36

<210> SEQ ID NO 84
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 84
cgcgctagca ctagacacgg tcacggtagt tcc                33

<210> SEQ ID NO 85
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 85
cgcgtcgacg ccaccatgga ctggacatgg tccatcctg                39

<210> SEQ ID NO 86
<211> LENGTH: 43
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 86
ttgacttatc ggcggtcagt gtggtccggc ctttaaacct ttc                43

<210> SEQ ID NO 87
<211> LENGTH: 42
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 87
acactgaccg ccgataagtc aacctccaca gcttacatgg aa                 42

<210> SEQ ID NO 88
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 88
cgcgctagca ctagacacgg tcacggtagt tcc                           33

<210> SEQ ID NO 89
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 89
cgcgtcgacg ccaccatgga catgagggtc cccgctcag                     39

<210> SEQ ID NO 90
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 90
cagcagctta ggggctttcc ctggtttctg                               30

<210> SEQ ID NO 91
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 91
gggaaagccc ctaagctgct gatctataat gaaaaa                        36

<210> SEQ ID NO 92
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 92
tgtcccagat ccactgccac tgaaccttga                                          30

<210> SEQ ID NO 93
<211> LENGTH: 36
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 93
agtggcagtg gatctgggac agactatact ctcacc                                   36

<210> SEQ ID NO 94
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 94
cgccgtacgt ttgatctcca ccttggtccc tcc                                      33

<210> SEQ ID NO 95
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 95
cgcgtcgacg ccaccatgga catgagggtc cccgctcag                                39

<210> SEQ ID NO 96
<211> LENGTH: 40
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 96
ggtgagagta tactgtgtcc cagatccact gccactgaac                               40

<210> SEQ ID NO 97
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 97
ggatctggga cacagtatac tctcaccatc agcagtctg                                39

<210> SEQ ID NO 98
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 98
cgccgtacgt ttgatctcca ccttggtccc tcc                                    33

<210> SEQ ID NO 99
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 99
cgcgctagca ccaagggccc atcggtcttc ccc                                    33

<210> SEQ ID NO 100
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 100
cgcgatatct catttacccg gagacaggga gag                                    33

<210> SEQ ID NO 101
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 101
cgccgtacgg tggctgcacc atctgtcttc atc                                    33

<210> SEQ ID NO 102
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 102
cgcgatatcc taacactctc ccctgttgaa gct                                    33

<210> SEQ ID NO 103
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 103
cgaactgtgg ctgcaccatc tgtc                                              24

<210> SEQ ID NO 104
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 104
cgcgcggccg cctaacactc tcccctgttg aagctctt                               38

<210> SEQ ID NO 105
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 105
ttgctgagca gcctgagatc tgaggacacg gcc                               33

<210> SEQ ID NO 106
<211> LENGTH: 30
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 106
agatctcagg ctgctcagca acatgtaggc                                  30

<210> SEQ ID NO 107
<211> LENGTH: 39
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 107
gcggaattcg tcgacgccac catgcgatgg agctggatc                        39

<210> SEQ ID NO 108
<211> LENGTH: 48
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 108
gaccgatggg cccttggtgg aggctgagga gactgtgaga gtggtgcc              48

<210> SEQ ID NO 109
<211> LENGTH: 41
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 109
gcctccacca agggcccatc ggtcttcccc ctggcgccct g                     41

<210> SEQ ID NO 110
<211> LENGTH: 35
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 110
cgcgcggccg ctcatttacc cggagacagg gagag                            35

<210> SEQ ID NO 111
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 111
gcggtcgacg ccaccatgag tgtgctcact cag                               33

<210> SEQ ID NO 112
<211> LENGTH: 49
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 112
gacagatggt gcagccacag ttcgttttat ttccagcttg gtcccccct              49

<210> SEQ ID NO 113
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 113
cgaactgtgg ctgcaccatc tgtc                                         24

<210> SEQ ID NO 114
<211> LENGTH: 38
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 114
cgcgcggccg cctaacactc tcccctgttg aagctctt                          38

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Gln His His Gly Val Thr Lys Cys Asn Ile Thr Cys Ser Lys Met
1               5                   10                  15

<210> SEQ ID NO 116
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Val Thr Lys Cys Asn Ile Thr Cys Ser Lys Met Thr Ser Lys
1               5                   10                  15

```
<210> SEQ ID NO 117
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Lys Cys Asn Ile Thr Cys Ser Lys Met Thr Ser Lys Ile Pro Val
1               5                   10                  15

<210> SEQ ID NO 118
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 118

Ile Thr Cys Ser Lys Met Thr Ser Lys Ile Pro Val Ala Leu Leu
1               5                   10                  15

<210> SEQ ID NO 119
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 119

Ser Lys Met Thr Ser Lys Ile Pro Val Ala Leu Leu Ile His Tyr
1               5                   10                  15

<210> SEQ ID NO 120
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 120

Thr Ser Lys Ile Pro Val Ala Leu Leu Ile His Tyr Gln Gln Asn
1               5                   10                  15

<210> SEQ ID NO 121
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 121

Ile Pro Val Ala Leu Leu Ile His Tyr Gln Gln Asn Gln Ala Ser
1               5                   10                  15

<210> SEQ ID NO 122
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 122

Ala Leu Leu Ile His Tyr Gln Gln Asn Gln Ala Ser Cys Gly Lys
1               5                   10                  15

<210> SEQ ID NO 123
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 123

Ile His Tyr Gln Gln Asn Gln Ala Ser Cys Gly Lys Arg Ala Ile
1               5                   10                  15

<210> SEQ ID NO 124
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 124

Gln Gln Asn Gln Ala Ser Cys Gly Lys Arg Ala Ile Ile Leu Glu
1               5                   10                  15

<210> SEQ ID NO 125
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 125

Gln Ala Ser Cys Gly Lys Arg Ala Ile Ile Leu Glu Thr Arg Gln
1               5                   10                  15

<210> SEQ ID NO 126
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 126

Cys Gly Lys Arg Ala Ile Ile Leu Glu Thr Arg Gln His Arg Leu
1               5                   10                  15

<210> SEQ ID NO 127
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 127

Arg Ala Ile Ile Leu Glu Thr Arg Gln His Arg Leu Phe Cys Ala
1               5                   10                  15

<210> SEQ ID NO 128
<211> LENGTH: 15

```
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 128

Ile Leu Glu Thr Arg Gln His Arg Leu Phe Cys Ala Asp Pro Lys
1               5                   10                  15

<210> SEQ ID NO 129
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Thr Arg Gln His Arg Leu Phe Cys Ala Asp Pro Lys Glu Gln Trp
1               5                   10                  15

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

His Arg Leu Phe Cys Ala Asp Pro Lys Glu Gln Trp Val Lys Asp
1               5                   10                  15

<210> SEQ ID NO 131
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Phe Cys Ala Asp Pro Lys Glu Gln Trp Val Lys Asp Ala Met Gln
1               5                   10                  15

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Asp Pro Lys Glu Gln Trp Val Lys Asp Ala Met Gln His Leu Asp
1               5                   10                  15

<210> SEQ ID NO 133
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Glu Gln Trp Val Lys Asp Ala Met Gln His Leu Asp Arg Gln Ala
```

```
<210> SEQ ID NO 134
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Val Lys Asp Ala Met Gln His Leu Asp Arg Gln Ala Ala Ala Leu
1               5                   10                  15

<210> SEQ ID NO 135
<211> LENGTH: 16
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Ala Met Gln His Leu Asp Arg Gln Ala Ala Ala Leu Thr Arg Asn Gly
1               5                   10                  15
```